US012746276B2

(12) United States Patent
Bolognani et al.

(10) Patent No.: US 12,746,276 B2
(45) **Date of Patent: *Sep. 29, 2026**

(54) MANUFACTURE, FORMULATION AND DOSING OF APRAGLUTIDE

(71) Applicant: VectivBio AG, Basel (CH)

(72) Inventors: Federico Bolognani, Biel-Benken (CH); Gleb Feldman, Oxford (GB); Jean-Marie Receveur, Copenhagen (DK); Torsten Weiss, Ishoej (DK)

(73) Assignee: VectivBio AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 19/039,081

(22) Filed: Jan. 28, 2025

(65) Prior Publication Data

US 2025/0186557 A1 Jun. 12, 2025

Related U.S. Application Data

(63) Continuation of application No. 18/929,208, filed on Oct. 28, 2024, which is a continuation of application No. 17/462,908, filed on Aug. 31, 2021, now Pat. No. 12,458,685, which is a continuation of application No. PCT/US2021/036655, filed on Jun. 9, 2021.

(60) Provisional application No. 63/157,083, filed on Mar. 5, 2021, provisional application No. 63/074,119, filed on Sep. 3, 2020, provisional application No. 63/036,507, filed on Jun. 9, 2020.

(51) Int. Cl.
*A61K 38/26* (2006.01)
*A61P 13/12* (2006.01)

(52) U.S. Cl.
CPC .............. *A61K 38/26* (2013.01); *A61P 13/12* (2018.01)

(58) Field of Classification Search
CPC ........ A61K 38/26; A61P 13/12; C07K 14/605
See application file for complete search history.

(56) References Cited

U.S. PATENT DOCUMENTS

| | | | | |
|---|---|---|---|---|
| 7,056,886 | B2 | 6/2006 | Isaacs | |
| 7,847,061 | B2 | 12/2010 | Sanguinetti et al. | |
| 8,580,918 | B2 | 11/2013 | Alagarsamy et al. | |
| 8,580,919 | B2 | 11/2013 | Bossard et al. | |
| 8,589,918 | B1 | 11/2013 | Sapuntzakis et al. | |
| 9,060,992 | B2 | 6/2015 | Sanguinetti et al. | |
| 9,545,434 | B2 | 1/2017 | Sanguinetti et al. | |
| 9,580,487 | B2 | 2/2017 | Larsen et al. | |
| 9,782,455 | B2 | 10/2017 | Wellings | |
| 10,253,080 | B2 | 4/2019 | Just et al. | |
| 11,766,470 | B2 * | 9/2023 | Bolognani | C07K 14/605 514/7.2 |
| 2009/0093408 | A1 | 4/2009 | Bridon et al. | |
| 2016/0158156 | A1 | 6/2016 | Fabio et al. | |
| 2020/0113975 | A1 | 4/2020 | Meenan et al. | |
| 2020/0254065 | A1 | 8/2020 | Hershkovitz | |
| 2020/0262888 | A1 | 8/2020 | Choi et al. | |
| 2022/0000985 | A1 | 1/2022 | Bolognani et al. | |
| 2022/0062384 | A1 | 3/2022 | Bolognani et al. | |
| 2023/0173033 | A1 | 6/2023 | Bolognani et al. | |
| 2023/0241179 | A1 | 8/2023 | Bolognani et al. | |
| 2024/0252595 | A1 | 8/2024 | Bolognani et al. | |
| 2024/0325500 | A1 | 10/2024 | Bolognani et al. | |
| 2025/0049893 | A1 | 2/2025 | Bolognani et al. | |

FOREIGN PATENT DOCUMENTS

| | | | |
|---|---|---|---|
| CN | 111329995 | A | 6/2020 |
| CN | 111518192 | A | 8/2020 |
| CN | 112057607 | A | 12/2020 |
| JP | 2003519195 | A | 6/2003 |
| JP | 2013508398 | A | 3/2013 |
| WO | WO-0149314 | A2 | 7/2001 |
| WO | WO-2005082404 | A2 | 9/2005 |
| WO | WO-2005082404 | A3 | 12/2005 |
| WO | WO-2006117565 | A2 | 11/2006 |
| WO | WO-2011050174 | A1 | 4/2011 |
| WO | WO-2012116792 | A1 | 9/2012 |
| WO | WO-2021252659 | A1 | 12/2021 |

OTHER PUBLICATIONS

Arakawa .T. et al., "Biotechnology Applications of Amino Acids in Protein Purification and Formulations," Amino Acids, 2007, 33: 587-605 (2007).
Berge, S. M., et al., "Pharmaceutical salts", Journal of Pharmaceutical Sciences (1977); 66(1): 1-19.
Bolognani, et al., The pharmacokinetic and pharmacodynamic relationship between apraglutide and citrulline: a randomized, placebo-controlled, double-blind study in healthy volunteers, Clinical Nutrition ESPEN, Dec. 2020, pp. 413-414.
Coin, Research Square, Monitoring solid phase peptide synthesis, Oct. 2007, 3 pages.
Deng, et al., Synthesis and comparative properties of two amide-generating resin linkers for use in solid phase peptide synthesis, Journal of Peptide Science, Oct. 2010, pp. 545-550.
Dionex, Thermo Scientific, Determination of Trifluoracetic Acid (TFA) in Peptides, application note 115, Thermo Scientific, 2002, 6 pages.
Eliasson, et al., Apraglutide, a Novel Long-Acting Glucagon-Like Peptide-2 Analog, in the Treatment of Patients with Short Bowel Syndrome: An Open-Label Phase 2 Trial, Gastroenterology, May 2020, p. S-741-S742.
Eliasson, et al., Effect of Apraglutide, a Novel Long-Acting Glucagon-Like Peptide-2 Analog, on Patients with Short Bowel Syndrome and Intestinal Insufficiency: Preliminary Results from an Open-Label Study, Gastroenterology, May 2019, p. S-691-S692.
Hargrove, et al., Pharmacological characterization of apraglutide, a novel long-acting peptidic glucagon-like peptide-2 agonist, for the treatment of short bowel syndrome, Journal of Pharmacology and Experimental Therapeutics, May 2020, pp. 193-203.
Izutsu, Journal of Pharmaceutical Science and Technology, Japan, 2012, pp. 353-358, vol. 72, No. 6.

(Continued)

*Primary Examiner* — Sudhakar Katakam
(74) *Attorney, Agent, or Firm* — Fenwick & West LLP; Heidi Erlacher; Eric A. Owens

(57) ABSTRACT

The present disclosure relates to methods of making, formulating and administering GLP-2 analogs.

32 Claims, 31 Drawing Sheets

Specification includes a Sequence Listing.

(56) References Cited

OTHER PUBLICATIONS

Jeppesen et al., Impaired meal stimulated glucagon-like peptide 2 response in ileal resected short bowel patients with intestinal failure, Gut, Oct. 1999, pp. 559-563.
Remington, Chapter 45: Oral solid dosage forms. In Remington: The Science and Practice of Pharmacy, 22nd, Ed., Jan. 2012, p. 947 (54 pages total).
Senderoff, et al., Consideration of conformational transitions and racemization during process development of recombinant glucagon-like peptide-1, Journal of pharmaceutical sciences, Feb. 1998, pp. 183-189.
Slim, et al. Novel Long-Acting GLP-2 Analogue, FE 203799 (Apraglutide), Enhances Adaptation and Linear Intestinal Growth in a Neonatal Piglet Model of Short Bowel Syndrome with Total Resection of the Ileum, Journal of Parenteral and Enteral Nutrition, Sep. 2019, pp. 891-898.
U.S. Appl. No. 18/929,208, filed Oct. 28, 2024, by Bolognani et al.
Wisniewski, et al. Synthesis and Pharmacological Characterization of Novel Glucagon-like Peptide-2 (GLP-2) Analogues with Low Systemic Clearance, Journal Medicinal Chemistry, Apr. 2016, pp. 3129-3139.
U.S. Appl. No. 19/095,349, filed Mar. 31, 2025, by Bolognani et al.

* cited by examiner

| **AA Pos.** | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|---|---|---|---|---|---|---|---|---|---|---|---|---|---|---|---|---|---|---|---|
| Native GLP-2 | H | A | D | G | S | F | S | D | E | M | N | T | I | L | D | N | L | A | A | R | D | F | I | N | W | L | I | Q | T | K | I | T | D | OH | | | | | |
| Teduglutide | H | G | D | G | S | F | S | D | E | M | N | T | I | L | D | N | L | A | A | R | D | F | I | N | W | L | I | Q | T | K | I | T | D | OH | | | | | |
| Glepaglutide | H | G | E | G | T | F | S | S | E | L | A | T | I | L | D | A | L | A | A | R | D | F | I | A | W | L | I | A | T | K | I | T | D | K | K | K | K | K | K $NH_2$ |
| **Apraglutide** | H | G | D | G | S | F | S | D | E | Nle | D-Phe | T | I | L | D | L | L | A | A | R | D | F | I | N | W | L | I | Q | T | K | I | T | D | $NH_2$ | | | | | |

Gly2 eliminates enzymatic cleavage by DPP-IV enzyme

Nle10, which does not contain sulfur, in place of Met10, eliminates formation of impurities which may form during chemical synthesis due to oxidation and alkylation of the sulfur atom of methionine.

Replacement of two asparagines, Asn11 by D-Phe11 and Asn16 by Leu16, causes a significant change in plasma protein binding and corresponding remarkable decrease in total clearance.

Change in C-terminus functionality from carboxylic acid to amide slows down the absorption from the SC injection site into the circulation increasing the terminal half-life. The lower charge due to the amide group is thought to result in a more limited solubility of the peptide and the formation of a transient "depot"

FIG. 1

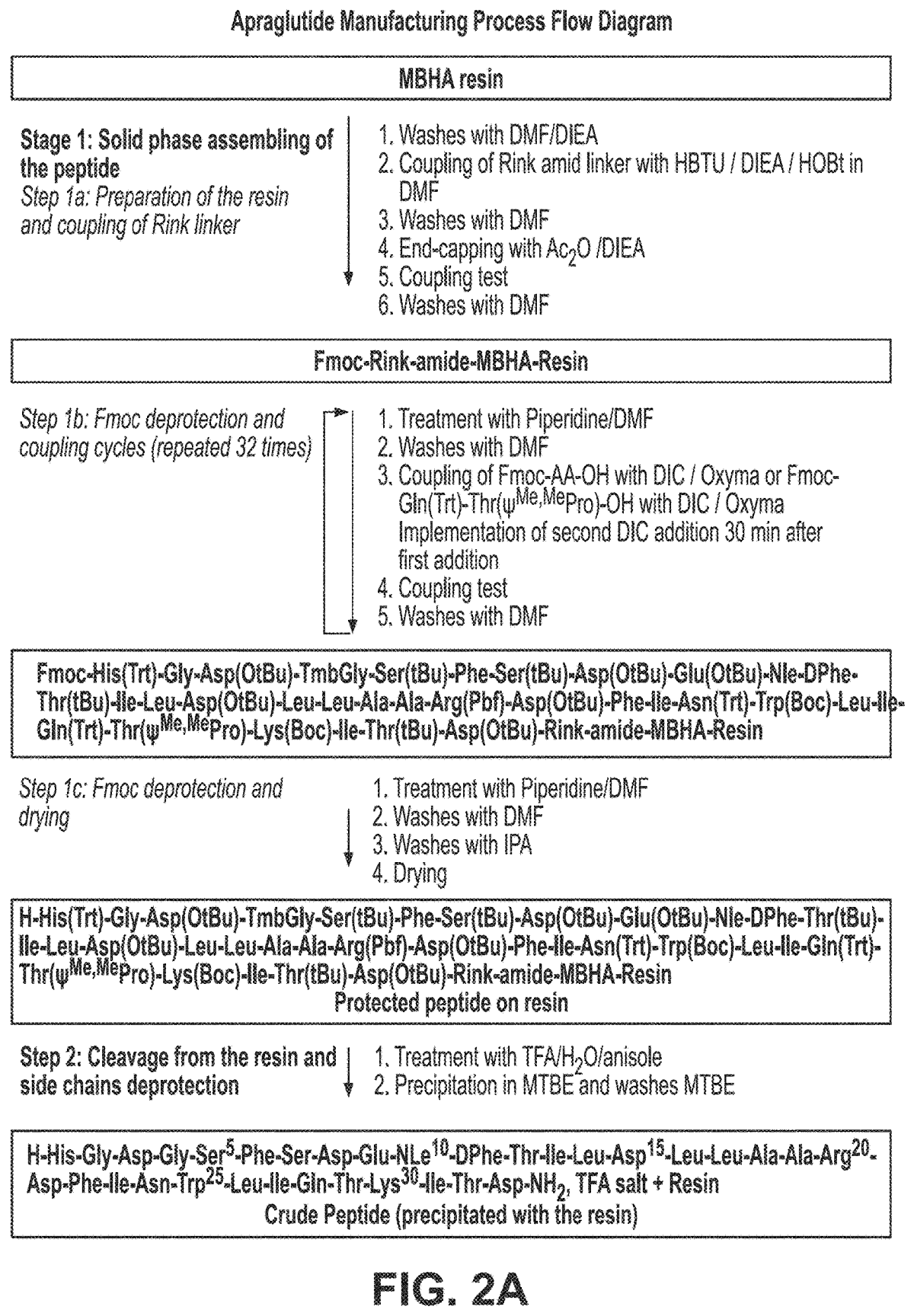

Apraglutide Manufacturing Process Flow Diagram

MBHA resin

Stage 1: Solid phase assembling of the peptide
*Step 1a: Preparation of the resin and coupling of Rink linker*

1. Washes with DMF/DIEA
2. Coupling of Rink amid linker with HBTU / DIEA / HOBt in DMF
3. Washes with DMF
4. End-capping with $Ac_2O$ /DIEA
5. Coupling test
6. Washes with DMF

Fmoc-Rink-amide-MBHA-Resin

*Step 1b: Fmoc deprotection and coupling cycles (repeated 32 times)*

1. Treatment with Piperidine/DMF
2. Washes with DMF
3. Coupling of Fmoc-AA-OH with DIC / Oxyma or Fmoc-Gln(Trt)-Thr($\psi^{Me,Me}$Pro)-OH with DIC / Oxyma Implementation of second DIC addition 30 min after first addition
4. Coupling test
5. Washes with DMF

Fmoc-His(Trt)-Gly-Asp(OtBu)-TmbGly-Ser(tBu)-Phe-Ser(tBu)-Asp(OtBu)-Glu(OtBu)-Nle-DPhe-Thr(tBu)-Ile-Leu-Asp(OtBu)-Leu-Leu-Ala-Ala-Arg(Pbf)-Asp(OtBu)-Phe-Ile-Asn(Trt)-Trp(Boc)-Leu-Ile-Gln(Trt)-Thr($\psi^{Me,Me}$Pro)-Lys(Boc)-Ile-Thr(tBu)-Asp(OtBu)-Rink-amide-MBHA-Resin

*Step 1c: Fmoc deprotection and drying*

1. Treatment with Piperidine/DMF
2. Washes with DMF
3. Washes with IPA
4. Drying

H-His(Trt)-Gly-Asp(OtBu)-TmbGly-Ser(tBu)-Phe-Ser(tBu)-Asp(OtBu)-Glu(OtBu)-Nle-DPhe-Thr(tBu)-Ile-Leu-Asp(OtBu)-Leu-Leu-Ala-Ala-Arg(Pbf)-Asp(OtBu)-Phe-Ile-Asn(Trt)-Trp(Boc)-Leu-Ile-Gln(Trt)-Thr($\psi^{Me,Me}$Pro)-Lys(Boc)-Ile-Thr(tBu)-Asp(OtBu)-Rink-amide-MBHA-Resin
Protected peptide on resin

Step 2: Cleavage from the resin and side chains deprotection

1. Treatment with TFA/$H_2O$/anisole
2. Precipitation in MTBE and washes MTBE

H-His-Gly-Asp-Gly-Ser$^{5}$-Phe-Ser-Asp-Glu-NLe$^{10}$-DPhe-Thr-Ile-Leu-Asp$^{15}$-Leu-Leu-Ala-Ala-Arg$^{20}$-Asp-Phe-Ile-Asn-Trp$^{25}$-Leu-Ile-Gln-Thr-Lys$^{30}$-Ile-Thr-Asp-$NH_2$, TFA salt + Resin
Crude Peptide (precipitated with the resin)

FIG. 2A

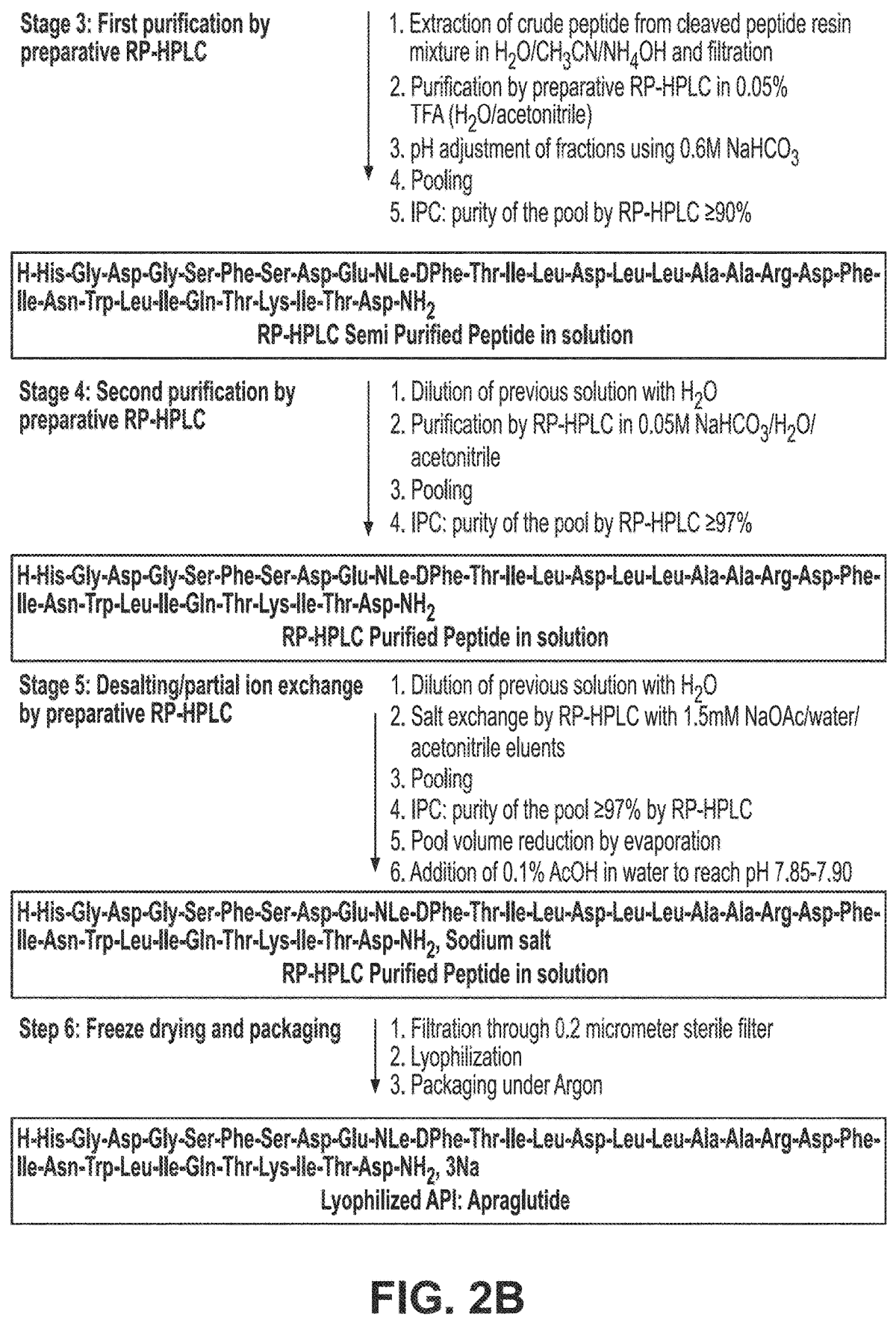

Stage 3: First purification by preparative RP-HPLC

1. Extraction of crude peptide from cleaved peptide resin mixture in $H_2O/CH_3CN/NH_4OH$ and filtration
2. Purification by preparative RP-HPLC in 0.05% TFA ($H_2O$/acetonitrile)
3. pH adjustment of fractions using 0.6M $NaHCO_3$
4. Pooling
5. IPC: purity of the pool by RP-HPLC ≥90%

H-His-Gly-Asp-Gly-Ser-Phe-Ser-Asp-Glu-NLe-DPhe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-$NH_2$
RP-HPLC Semi Purified Peptide in solution

Stage 4: Second purification by preparative RP-HPLC

1. Dilution of previous solution with $H_2O$
2. Purification by RP-HPLC in 0.05M $NaHCO_3/H_2O$/acetonitrile
3. Pooling
4. IPC: purity of the pool by RP-HPLC ≥97%

H-His-Gly-Asp-Gly-Ser-Phe-Ser-Asp-Glu-NLe-DPhe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-$NH_2$
RP-HPLC Purified Peptide in solution

Stage 5: Desalting/partial ion exchange by preparative RP-HPLC

1. Dilution of previous solution with $H_2O$
2. Salt exchange by RP-HPLC with 1.5mM NaOAc/water/acetonitrile eluents
3. Pooling
4. IPC: purity of the pool ≥97% by RP-HPLC
5. Pool volume reduction by evaporation
6. Addition of 0.1% AcOH in water to reach pH 7.85-7.90

H-His-Gly-Asp-Gly-Ser-Phe-Ser-Asp-Glu-NLe-DPhe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-$NH_2$, Sodium salt
RP-HPLC Purified Peptide in solution

Step 6: Freeze drying and packaging

1. Filtration through 0.2 micrometer sterile filter
2. Lyophilization
3. Packaging under Argon

H-His-Gly-Asp-Gly-Ser-Phe-Ser-Asp-Glu-NLe-DPhe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-$NH_2$, 3Na
Lyophilized API: Apraglutide

FIG. 2B

Flow Diagram of Apraglutide for Injection Manufacture

FIT = Filter integrity test

SEQUENCE LISTING

```
Sequence total quantity: 4
SEQ ID NO: 1           moltype = AA  length = 33
FEATURE                Location/Qualifiers
source                 1..33
                       mol_type = protein
                       organism = Homo sapiens
SEQUENCE: 1
HADGSFSDEM NTILDNLAAR DFINWLIQTK ITD                        33

SEQ ID NO: 2           moltype = AA  length = 33
FEATURE                Location/Qualifiers
REGION                 1..33
                       note = APRAGLUTIDE
SITE                   10
                       note = MISC_FEATURE - Nle
SITE                   11
                       note = MISC_FEATURE - D-Phe
source                 1..33
                       mol_type = protein
                       organism = synthetic construct
SEQUENCE: 2
HGDGSFSDEX FTILDLLAAR DFINWLIQTK ITD                        33
```

-continued

```
SEQ ID NO: 3            moltype = AA  length = 33
FEATURE                 Location/Qualifiers
REGION                  1..33
                        note = Teduglutide
source                  1..33
                        mol_type = protein
                        organism = synthetic construct
SEQUENCE: 3
HGDGSFSDEM NTILDNLAAR DFINWLIQTK ITD                               33

SEQ ID NO: 4            moltype = AA  length = 39
FEATURE                 Location/Qualifiers
REGION                  1..39
                        note = Glepaglutide
source                  1..39
                        mol_type = protein
                        organism = synthetic construct
SEQUENCE: 4
HGEGTFSSEL ATILDALAAR DFIAWLIATK ITDKKKKKK                         39
```

MANUFACTURE, FORMULATION AND DOSING OF APRAGLUTIDE

RELATED APPLICATIONS

This application is a Continuation of U.S. patent application Ser. No. 18/929,208, filed Oct. 28, 2024, which is a Continuation of U.S. patent application Ser. No. 17/462,908, filed Aug. 31, 2021, which is a Continuation of International Patent Application No. PCT/US2021/036655, filed Jun. 9, 2021, which claims priority to, and the benefit of, U.S. Provisional Application No. 63/036,507, filed Jun. 9, 2020, U.S. Provisional Application No. 63/074,119, filed Sep. 3, 2020, and U.S. Provisional Application No. 63/157,083, filed Mar. 5, 2021. The contents of each of the aforementioned patent applications are incorporated herein by reference in their entireties.

REFERENCE TO AN ELECTRONIC SEQUENCE LISTING

The contents of the electronic sequence listing (VECT_002_C08US_SeqList_ST26.xml; Size 6,266; and Date of Creation: Jan. 27, 2025) are herein incorporated by reference in their entireties.

TECHNICAL FIELD

The present disclosure relates to manufacture, formulation and dosing of apraglutide.

BACKGROUND

Glucagon-like peptide 2 (GLP-2) is a 33-amino-acid peptide released from the post-translational processing of proglucagon in the enteroendocrine L cells of the intestine.

We contemplate using apraglutide to treat intestinal disorders or dysfunction. In one embodiment we contemplate treatment of short bowel syndrome. Short bowel syndrome is a malabsorptive condition characterized by extreme reduction in functional intestinal length most commonly as a result of surgical resection due to mesenteric ischemia or Inflammatory Bowel Disease (IBD) although other etiologies are also present. SBS with intestinal failure (SBS-IF) is defined as the reduction of gut function below the minimum necessary for the absorption of macronutrients and/or fluids and electrolytes, such that intravenous supplementation is required to maintain health and/or growth. In patients with SBS-IF parenteral support (PS) delivered through a central venous catheter is needed to maintain an adequate fluid, energy, electrolytes, trace elements, vitamins, and nutrient balance. There is spectrum of SBS-IF patients from those with stoma and no colon-in-continuity (CIC) requiring large PS volumes to those with CIC which require lower PS volumes. As a consequence of this spectrum, decreased dependency on PS can be demonstrated in a variety of outcomes depending on anatomy, including PS volume reduction, days off PS, or achieving enteral autonomy. After surgical resection, the remaining intestine goes through a process called intestinal adaptation by which it increases its absorptive capacity to compensate for its reduced length. It has been demonstrated that this process of intestinal adaptation can be enhanced by administering glucagon-like peptide 2 (GLP-2) or more stable analogues with extended half-lives such as teduglutide and apraglutide. Because of the physiological role of the colon, patients with CIC can manage fluid balance much better than patients with no functional colon and have lower parenteral support volumes at baseline compared with stoma patients. PS is defined as any intravenous infusion that contains fluids and electrolytes and may or may not include parenteral nutrition (PN). Parenteral nutrition is defined as PS that includes protein, carbohydrate, fat, vitamins and/or trace elements. Patients with chronic intestinal failure due to benign disease have a high probability of long-term survival on PS.

GLP-2 has attracted considerable attention as a therapeutic agent for intestinal injury since its identification as a potent stimulator of mucosal epithelial proliferation. Preliminary trials in patients with short bowel syndrome have produced improvements in intestinal absorption of both fluids and nutrients. GLP-2 induces significant growth of the small intestinal mucosal epithelium. It also slows intestinal transit. Naturally occurring GLP-2 is, however, not a suitable drug candidate, as it is rapidly degraded by peptidases (e.g. DPP IV). As a result, GLP-2 has a very short half-life (t1/2=10 min. in humans) and rapid clearance (CL).

A method is needed to generate a high yielding and substantially pure GLP-2 analog peptide with improved pharmacokinetic properties. Further, there is a need for a GLP-2 analog peptide composition that is substantially pure e.g. substantially free from impurities. The present disclosure is directed to satisfying this need.

SUMMARY OF THE DISCLOSURE

In one aspect, a novel synthesis of a GLP-2 analog of high purity is disclosed. In another aspect, a novel sodium salt of a GLP-2 analog is disclosed. The method may comprise performing solid phase peptide synthesis (SPPS) on a resin, cleaving the synthesized GLP-2 analog peptide off the resin and deprotecting the side chains of the peptide by treating the resin with a solution comprising trifluoroacetic acid (TFA), water, and anisole, performing two purifications using reversed-phase high performance liquid chromatography (RP-HPLC), and freeze-drying and packaging the purified peptide powder comprising the substantially pure GLP-2 analog peptide. In some embodiments, the apraglutide has a purity of no less than 95%. In some embodiments, the apraglutide has a purity of no less than 97%.

Another aspect of the present disclosure is directed to the GLP-2 analog peptide having a purity of at least 97%. In some embodiments, the GLP-2 analog peptide, such as apraglutide, comprises less than 1% of a Des-$Gly^4$ apraglutide impurity; and/or less than 3% of the sum of $Aspartimide^3$ apraglutide, $Asp^{33}$-OH apraglutide and Des-$Ser^7$ apraglutide impurities; and/or less than 1% of a [$Trp^{25}$, 2-(2,4,6-trimethoxyphenyl)] apraglutide impurity.

Another aspect of the present disclosure is directed to the GLP-2 analog peptide having a purity of at least 97%. In some embodiments, the GLP-2 analog peptide, such as apraglutide, comprises less than or equal to 1% of a Des-$Gly^4$ apraglutide impurity; and/or less than or equal to 3% of the sum of $Aspartimide^3$ apraglutide, $Asp^{33}$-OH apraglutide and Des-$Ser^7$ apraglutide impurities; and/or less than or equal to 1% of a [$Trp^{25}$, 2-(2,4,6-trimethoxyphenyl)] apraglutide impurity.

Another aspect of the present disclosure is directed to the GLP-2 analog peptide having a purity of at least 97%. In some embodiments, the GLP-2 analog peptide, such as apraglutide, comprises less than 1% of the sum of Des-$Gly^4$ apraglutide and $Aspartimide^3$ apraglutide impurities, less than 1% of D-$Aspartimide^3$ apraglutide impurity, less than 1% of $Asp^{33}$-OH apraglutide impurity, less than 1% of Des-Ser[7] apraglutide impurities, and/or less than 1% of a [Trp[25], 2-(2,4,6-trimethoxyphenyl)] apraglutide impurity.

Another aspect of the present disclosure is directed to the GLP-2 analog peptide having a purity of at least 97%. In some embodiments, the GLP-2 analog peptide, such as apraglutide, comprises less than or equal to 1% of the sum of Des-Gly[4] apraglutide and Aspartimide[3] apraglutide impurities, less than or equal to 1% of D-Aspartimide[3] apraglutide impurity, less than or equal to 1% of Asp[33]-OH apraglutide impurity, less than or equal to 1% of Des-Ser[7] apraglutide impurities, and/or less than or equal to 1% of a [Trp[25], 2-(2,4,6-trimethoxyphenyl)] apraglutide impurity.

The Inventors have Recognized that:

i) replacement of Fmoc-protected amino acids: Fmoc-Gln(Trt)-OH, Fmoc-Thr(tBu)-OH and Fmoc-Gly-OH with Fmoc-Gln(Trt)-Thr($\psi^{Me,Me}$pro)-OH and Fmoc-Tmb-Gly-OH during Fmoc deprotection and coupling cycles improves coupling efficiency and reduces aspartimide formation;

ii) the use of oxyma instead of HOBt as the coupling additive during Fmoc deprotection and coupling cycles minimizes peptide oxidation and [Trp[25], 2-(2,4,6-trimethoxyphenyl)] apraglutide impurity formation; and iii) during sodium salt conversion by preparative RP-HPLC, the use of acetonitrile (ACN) for the mobile phase composition, the introduction of a pH adjustment step, and the removal of a titration step, improves apraglutide sodium salt conversion and purified apraglutide quality. In another aspect, a novel formulation and salt of apraglutide is disclosed.

According to one embodiment, the GLP-2 analog peptide of the present disclosure has the chemical structure:

In another aspect, a novel method of dosing an effective amount of apraglutide to patients in need thereof is disclosed. In some embodiments, the effective amount comprises between 1 and 10 mg of the apraglutide or a pharmaceutically acceptable salt thereof. In a preferred embodiment, apraglutide or a pharmaceutically acceptable salt thereof is dosed at 2.5 mg once weekly in patients that weigh less than 50 kg. In another preferred embodiment, apraglutide or a pharmaceutically acceptable salt thereof is dosed at 5.0 mg once weekly in patients that weigh 50 kg or more. In some embodiments, the method comprises administering apraglutide or pharmaceutically acceptable salt thereof intravenously. In other embodiments, the method comprises administering apraglutide or pharmaceutically acceptable salt thereof subcutaneously.

In some embodiments, the method comprises administering the compound or pharmaceutically acceptable salt thereof at a frequency between twice daily and twice monthly, preferably once weekly.

There is a need for a GLP-2 analog with a longer half-life, such as apraglutide, that can be dosed less than once daily, preferably once weekly.

BRIEF DESCRIPTION OF THE DRAWINGS

FIG. 1 shows the peptide sequence and structure for an exemplary GLP-2 agonist (apraglutide) that can be used in the methods of the present disclosure. Sequences shown in FIG. 1 correspond to SEQ ID NOs: 1-4.

FIG. 2A is a flow diagram schematic of steps 1-2 in a first aspect of the present disclosure directed to an improved method of making a GLP-2 analog peptide, such as apraglutide (hereafter referred to as Process B).

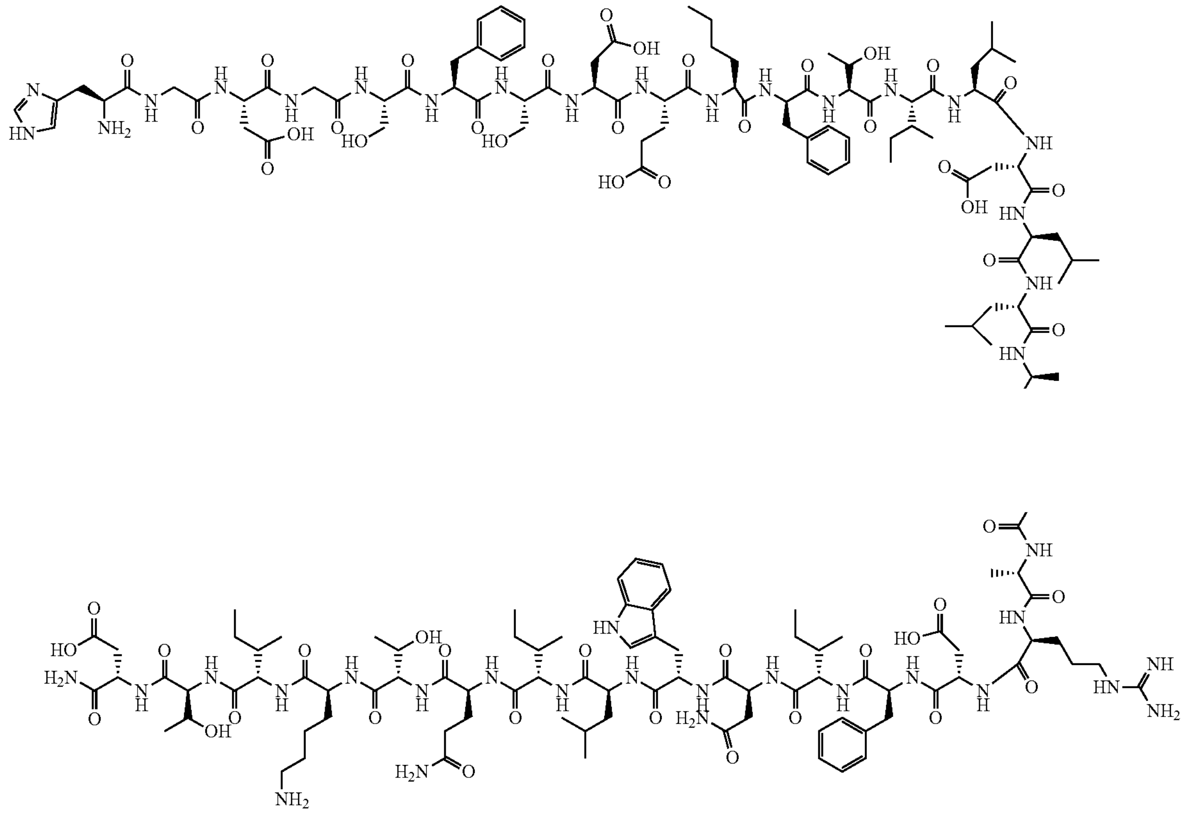

FIG. 2B is a flow diagram schematic of steps 3-6 in a first aspect of the present disclosure directed to an improved method of making a GLP-2 analog peptide, such as apraglutide (hereafter referred to as Process B).

Figure 3:
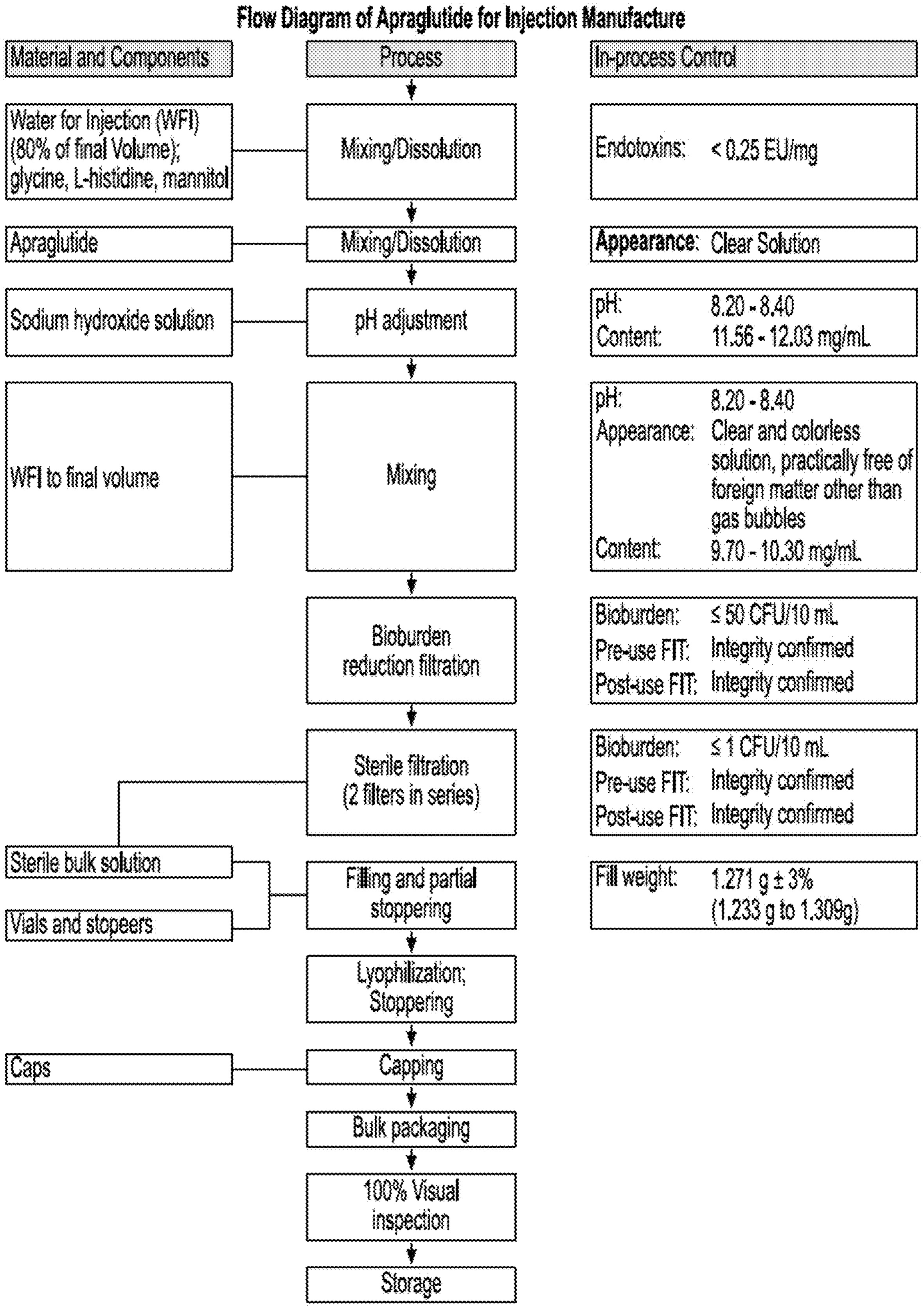

FIG. 3 is flow diagram schematic of a manufacturing process of the present disclosure directed to the production of a pharmaceutical composition comprising apraglutide.

Figure 4:
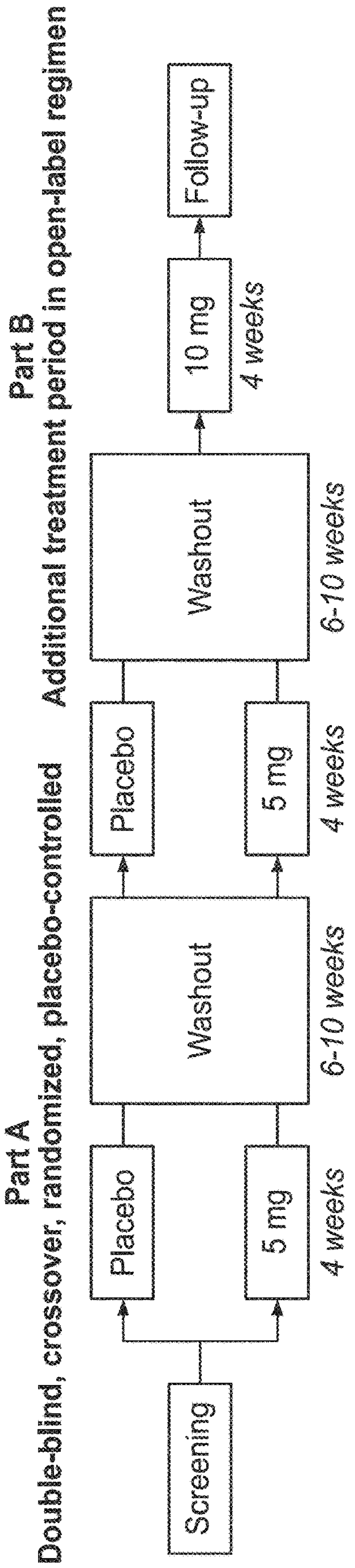

FIG. 4 is a diagram schematic of the trial design of the present disclosure.

Figure 5:
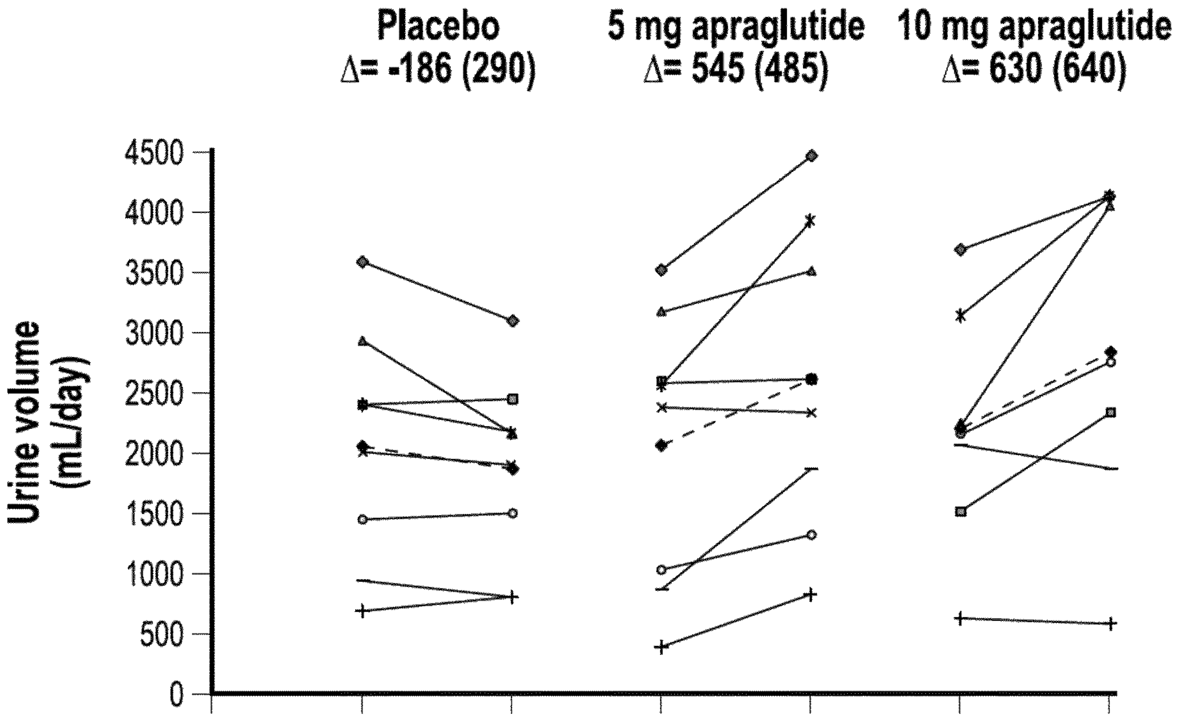

FIG. 5 is a graph showing individual and mean changes from baseline to end of treatment in urine volume output (mL/day). Dashed line denotes the mean, A denotes the mean change from baseline (standard deviation). The difference in grayscale shows individual patients.

Figure 6:
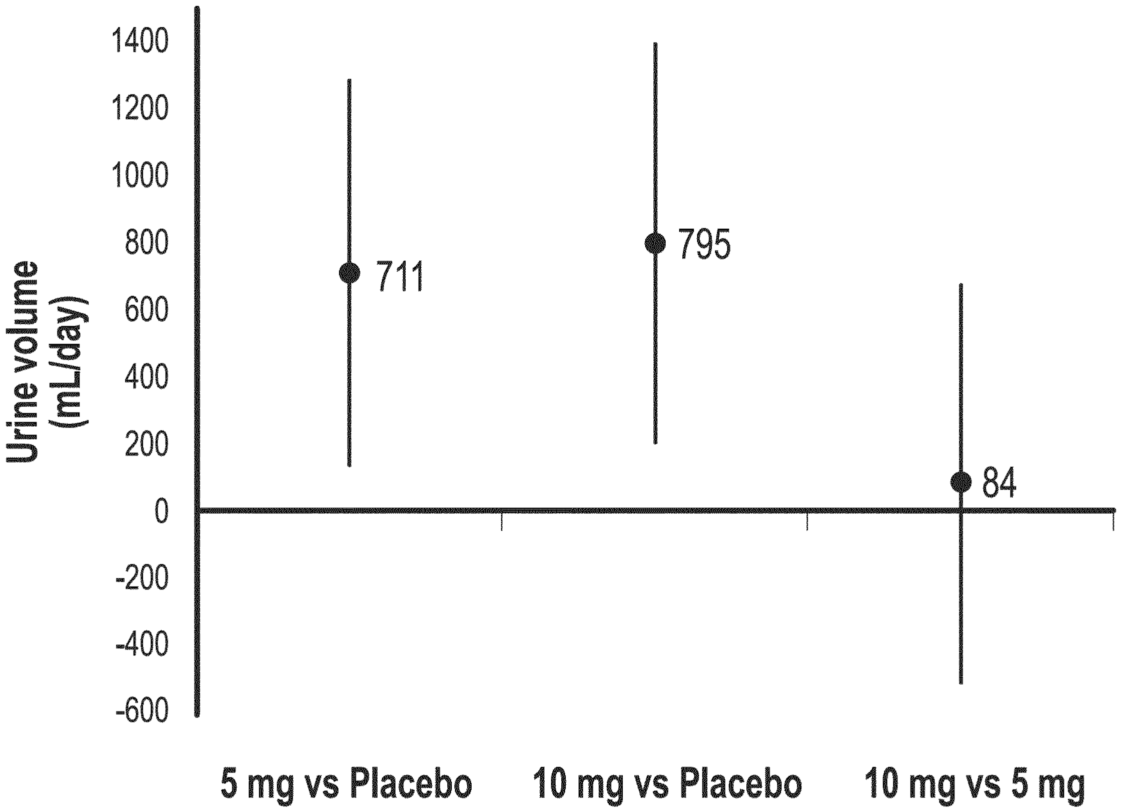

FIG. 6 is a graph showing the changes from baseline in urine volume output (mL/day) where the adjusted mean (points) and 95% CI (black lines) are from analysis Part A+B.

Figure 7:
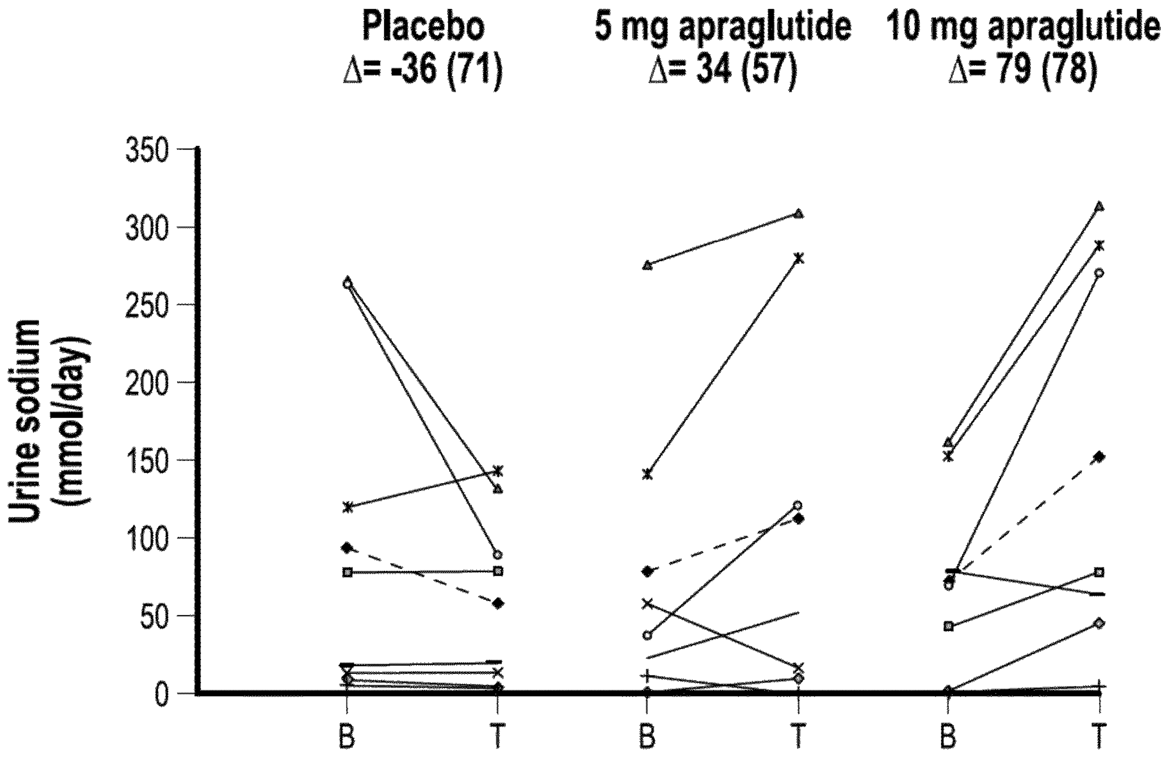

FIG. 7 is a graph showing individual and mean changes from baseline to end of treatment in urine sodium excretion (mmol/day). Dashed line denotes the mean, B denotes the baseline, T denotes treatment, A denotes the mean change from baseline (standard deviation). The difference in grayscale shows individual patients.

Figure 8:
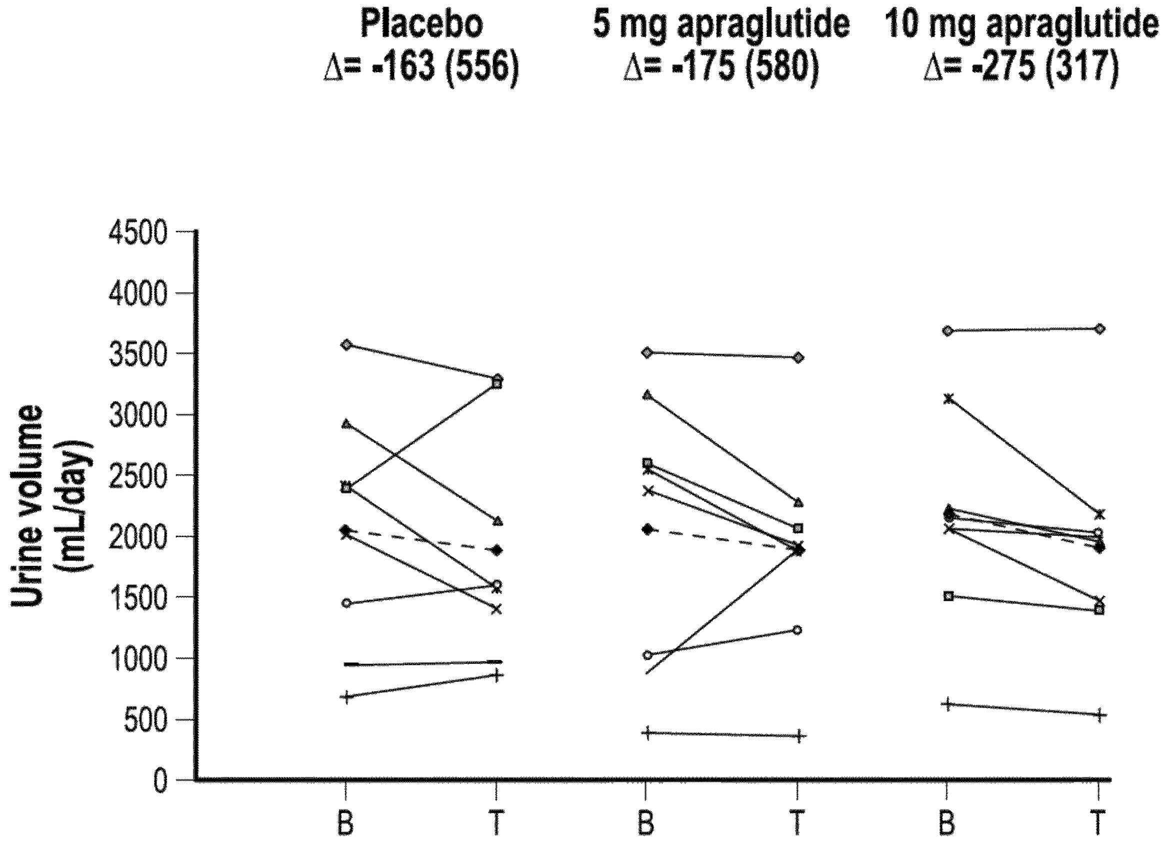

FIG. 8 is a graph showing individual and mean changes from baseline to immediately after first injection in urine volume output. Dashed line denotes the mean, B denotes the baseline, T denotes treatment, Δ denotes the mean change from baseline (standard deviation). The difference in grayscale shows individual patients.

Figure 9:
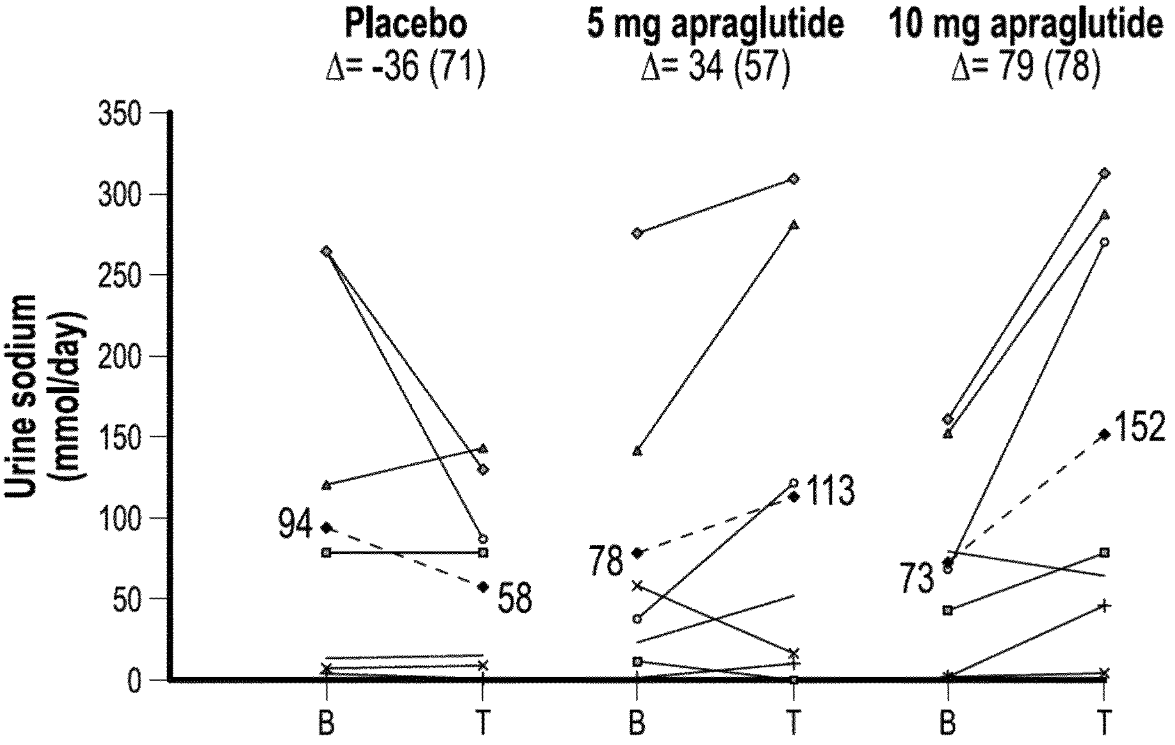

FIG. 9 is a graph showing individual and mean changes from baseline to immediately after first treatment in urine sodium excretion. Dashed line denotes the mean, B denotes the baseline, T denotes treatment, Δ denotes the mean change from baseline (standard deviation). The difference in grayscale shows individual patients.

Figure 10A:
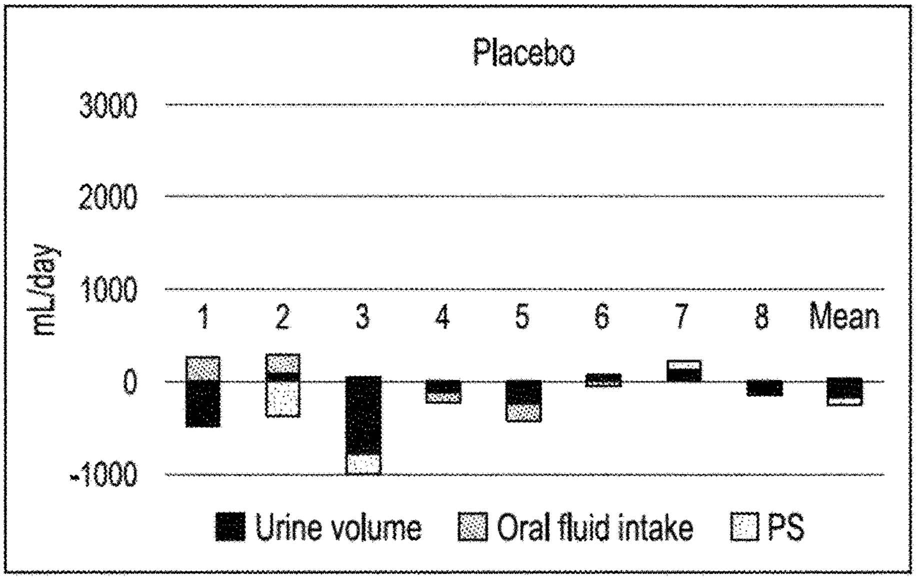

FIG. 10A is a graph showing individual changes and mean change in fluid composite effect in patients receiving placebo treatment. Fluid composite effect, defined as the sum of increase urine production (day 27-29), reduction in PS volume and reduction in spontaneous oral fluid intake (day 20-22).

Figure 10B:
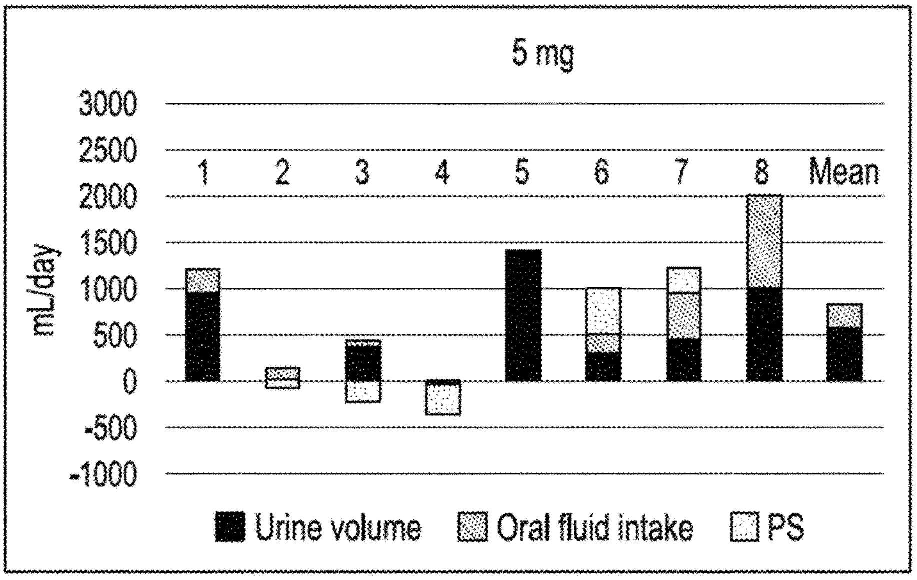

FIG. 10B is a graph showing individual changes and mean change in fluid composite effect in patients receiving 5 mg apraglutide. Fluid composite effect, defined as the sum of increase urine production (day 27-29), reduction in PS volume and reduction in spontaneous oral fluid intake (day 20-22).

Figure 10C:
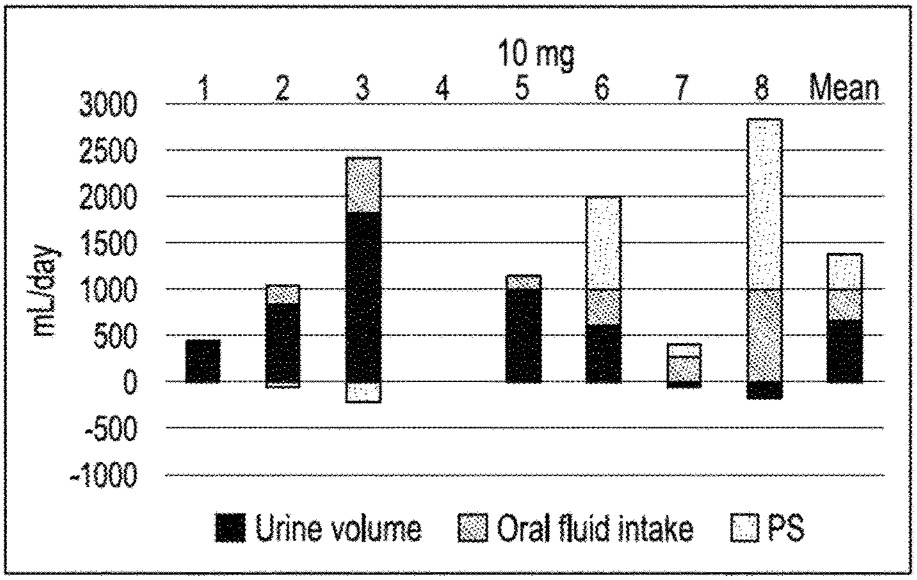

FIG. 10C is a graph showing individual changes and mean change in fluid composite effect in patients receiving 10 mg apraglutide. Fluid composite effect, defined as the sum of increase urine production (day 27-29), reduction in PS volume and reduction in spontaneous oral fluid intake (day 20-22).

Figure 11:
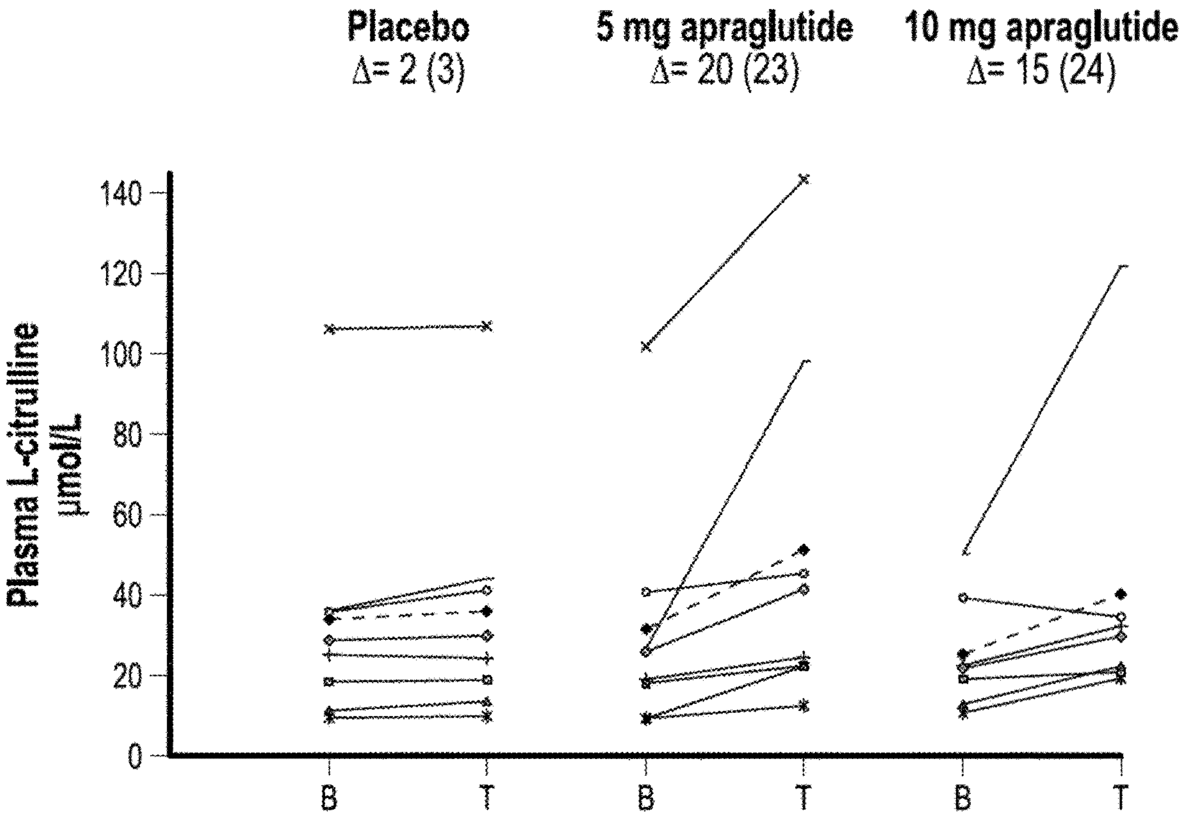

FIG. 11 is a graph showing individual and mean changes from baseline to end of treatment in absolute concentrations of plasma L-citrulline. Dashed line denotes the mean, B denotes the baseline, T denotes treatment, Δ denotes the mean change from baseline (standard deviation). The difference in grayscale shows individual patients.

Figure 12:
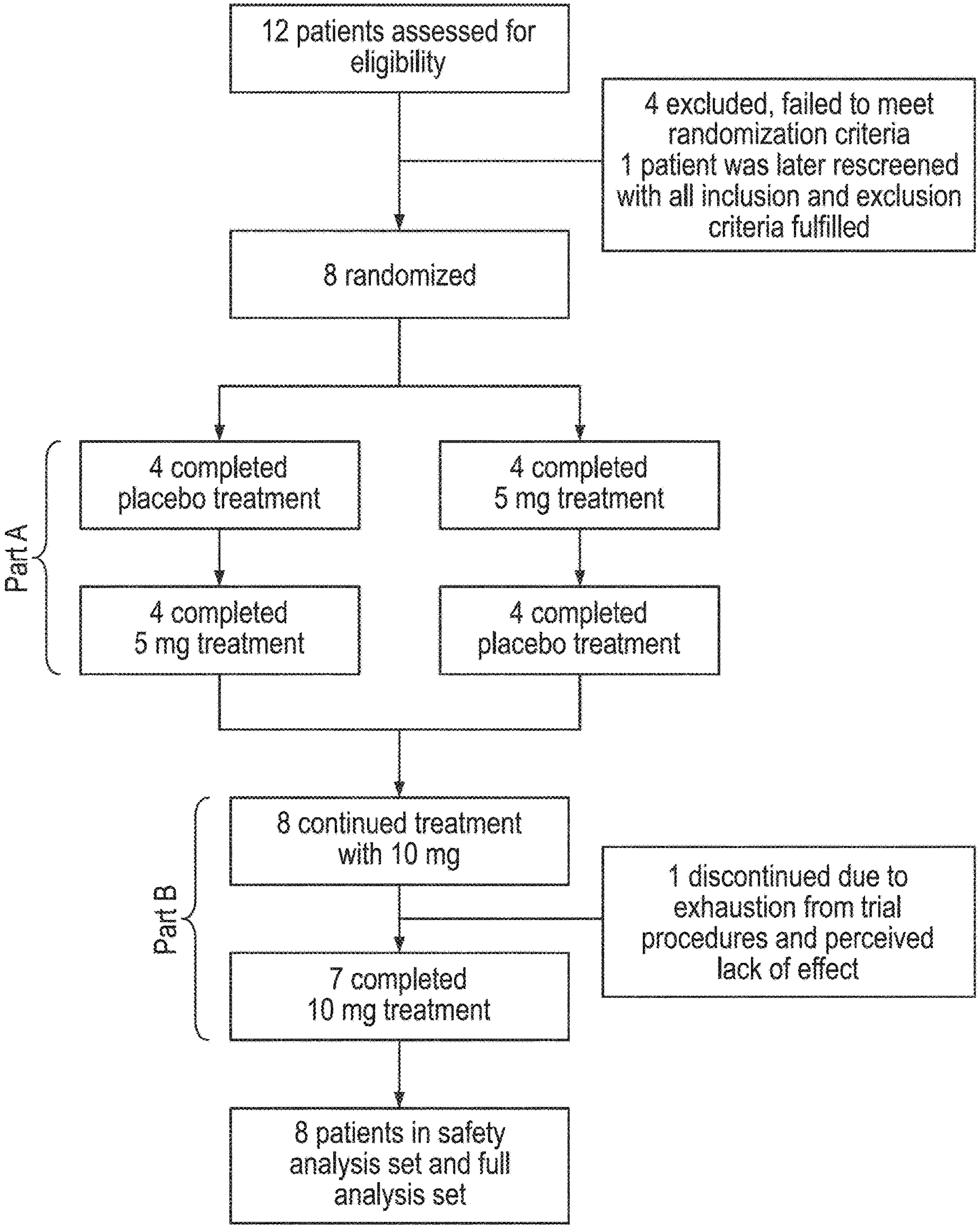

FIG. 12 is a diagram schematic of the Consolidated Standards of Reporting Trials (CONSORT).

Figure 13:
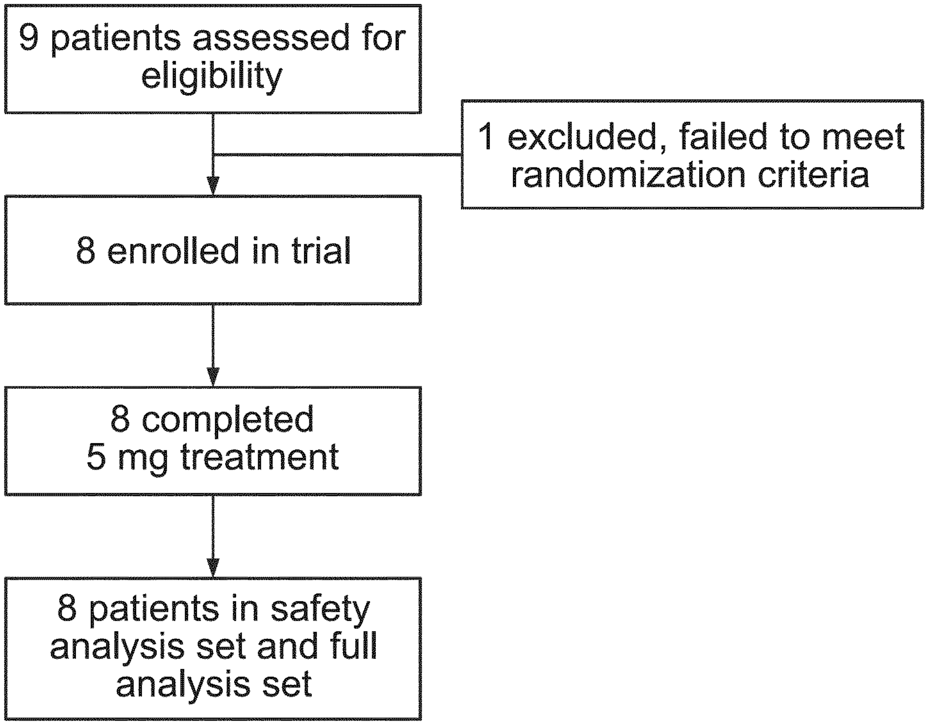

FIG. 13 is a diagram schematic of the Consolidated Standards of Reporting Trials (CONSORT).

Figure 14:
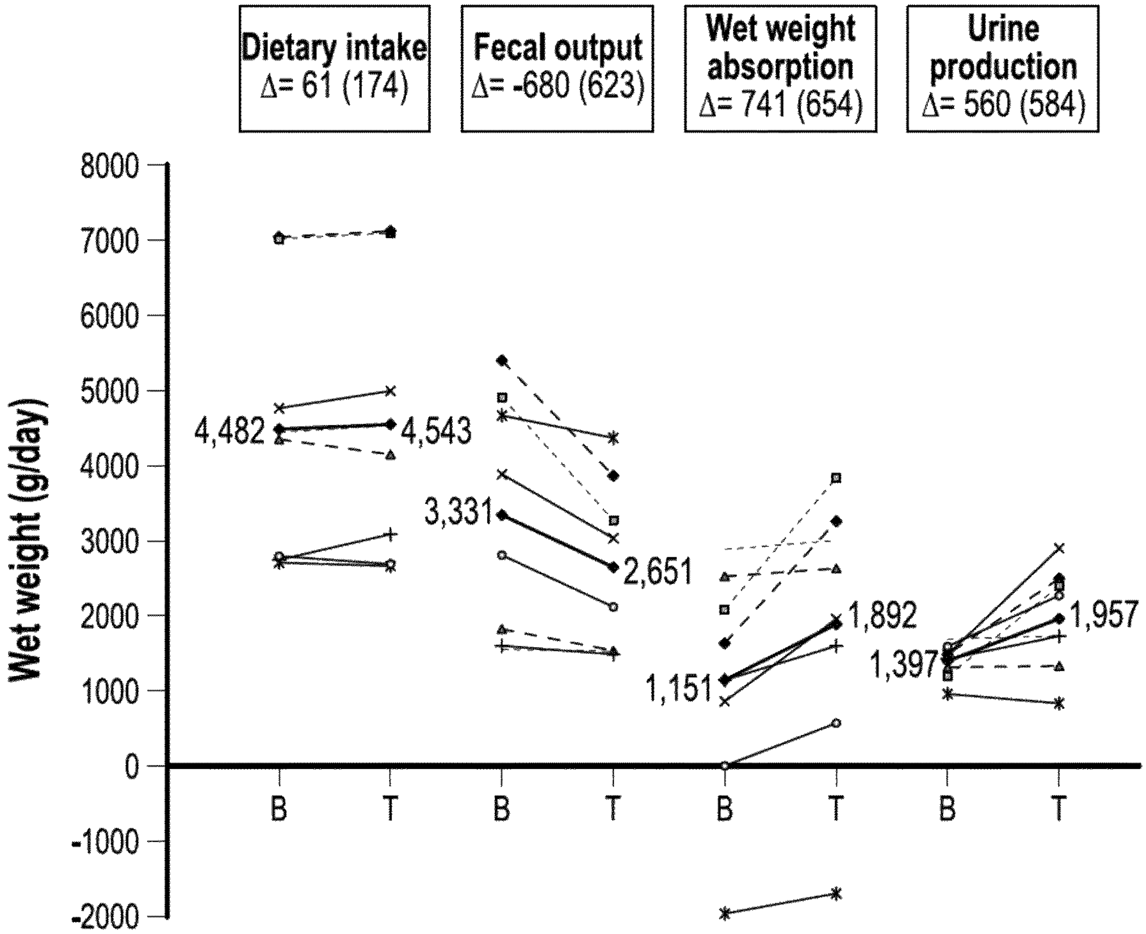

FIG. 14 is a graph showing individual and mean changes from baseline to end of treatment in wet weight dietary intake, fecal output, intestinal absorption and urine production. Bold line denotes the mean, B denotes the baseline, T denotes treatment, Δ denotes the mean change from baseline (standard deviation). Dashed lines show patients with SBS-II. Difference in grayscale shows individual patients.

Figure 15:
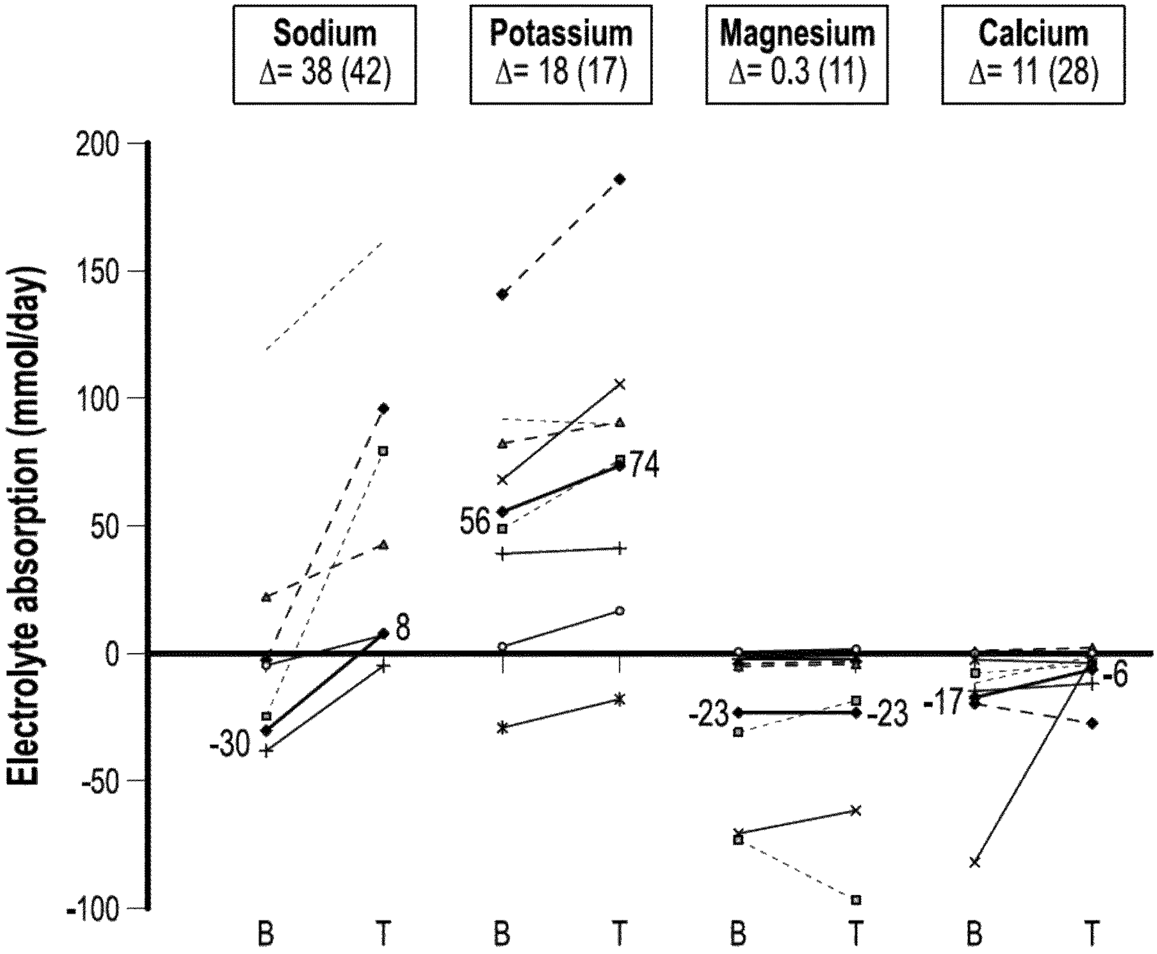

FIG. 15 is a graph showing individual and mean changes from baseline to end of treatment absorption of potassium, sodium, magnesium and calcium. Bold line denotes the mean, B denotes the baseline, T denotes treatment, Δ denotes the mean change from baseline (standard deviation). Dashed lines show patients with SBS-II. Difference in grayscale shows individual patients.

Figure 16:
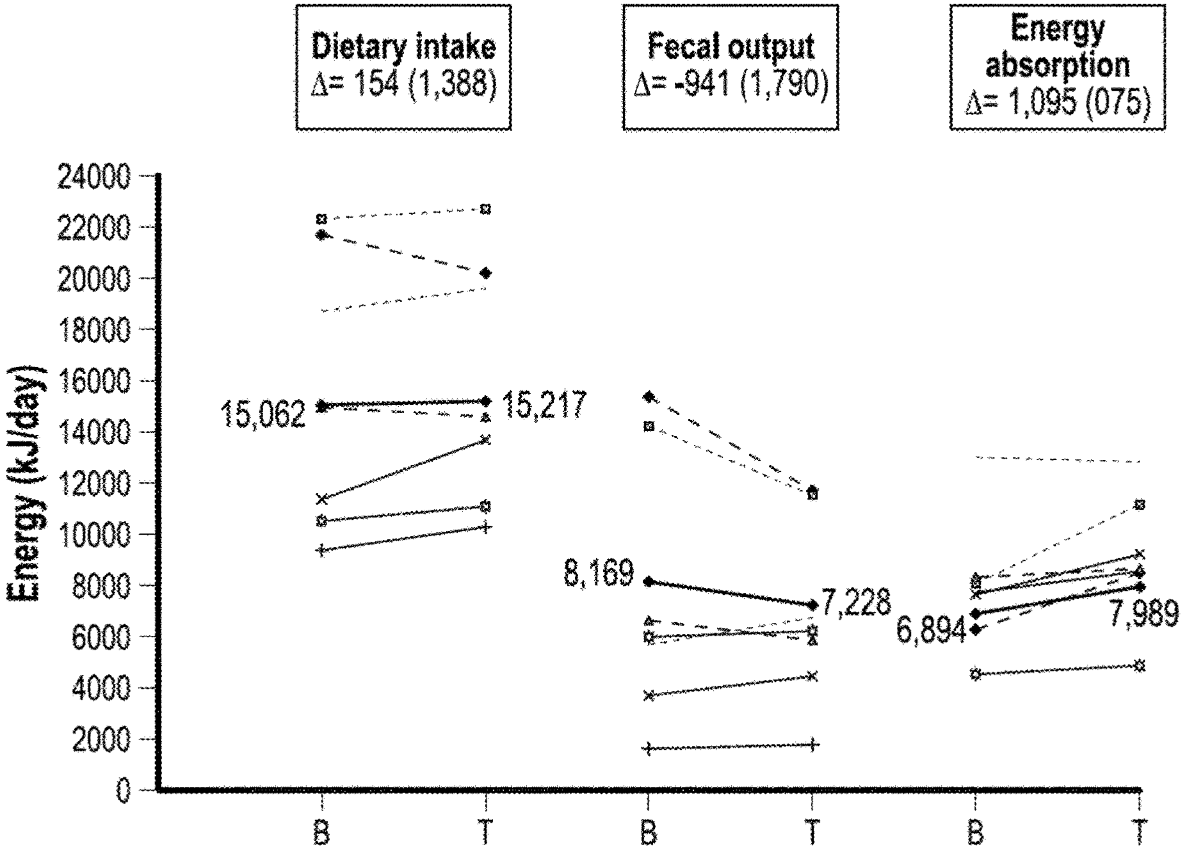

FIG. 16 is a graph showing individual and mean changes from baseline to end of treatment in the energy dietary intake, fecal output and absorption. Bold line denotes the mean, B denotes the baseline, T denotes treatment, Δ denotes the mean change from baseline (standard deviation). Dashed lines show patients with SBS-II. Difference in grayscale shows individual patients.

Figure 17:
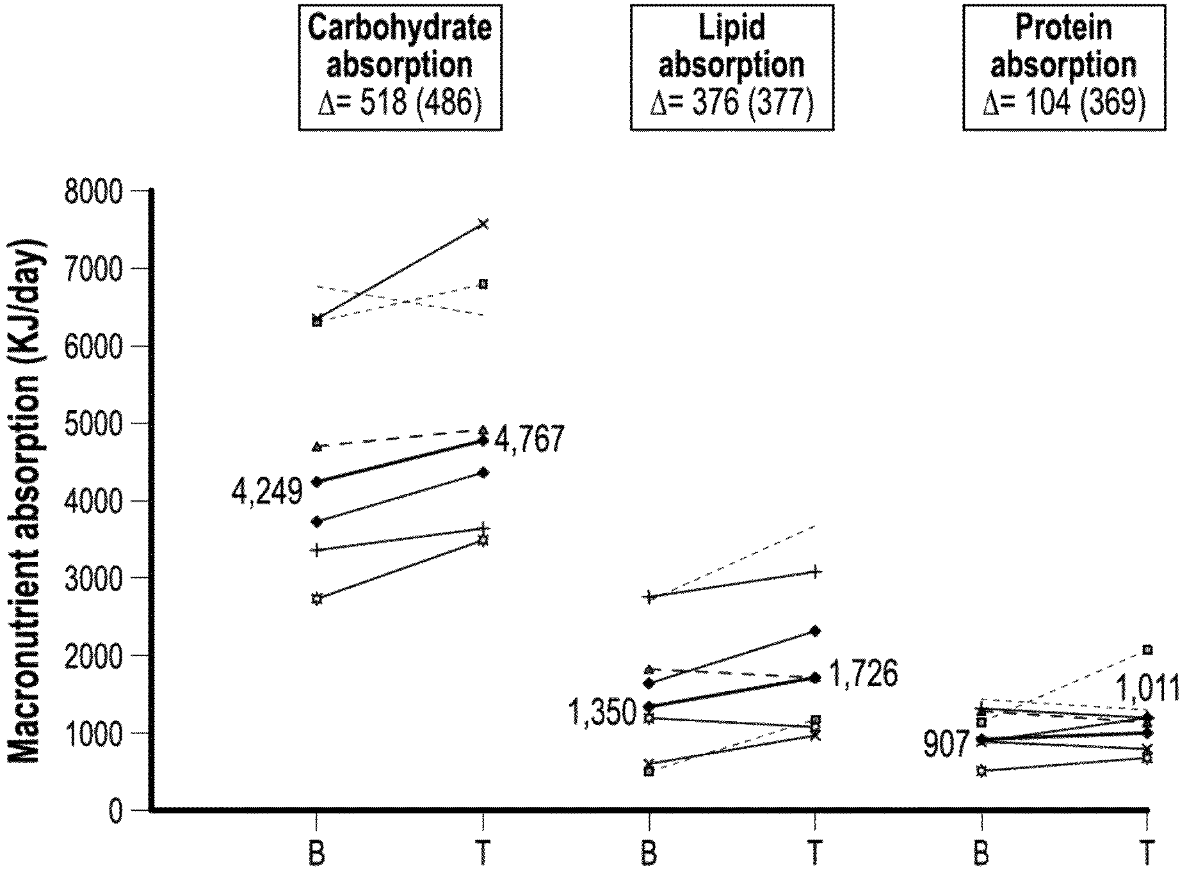

FIG. 17 is a graph showing individual and mean changes from baseline to end of treatment in absorption of macronutrients. Bold line denotes the mean, B denotes the baseline, T denotes treatment, Δ denotes the mean change from baseline (standard deviation). Dashed lines show patients with SBS-II. Difference in grayscale shows individual patients.

Figure 18:
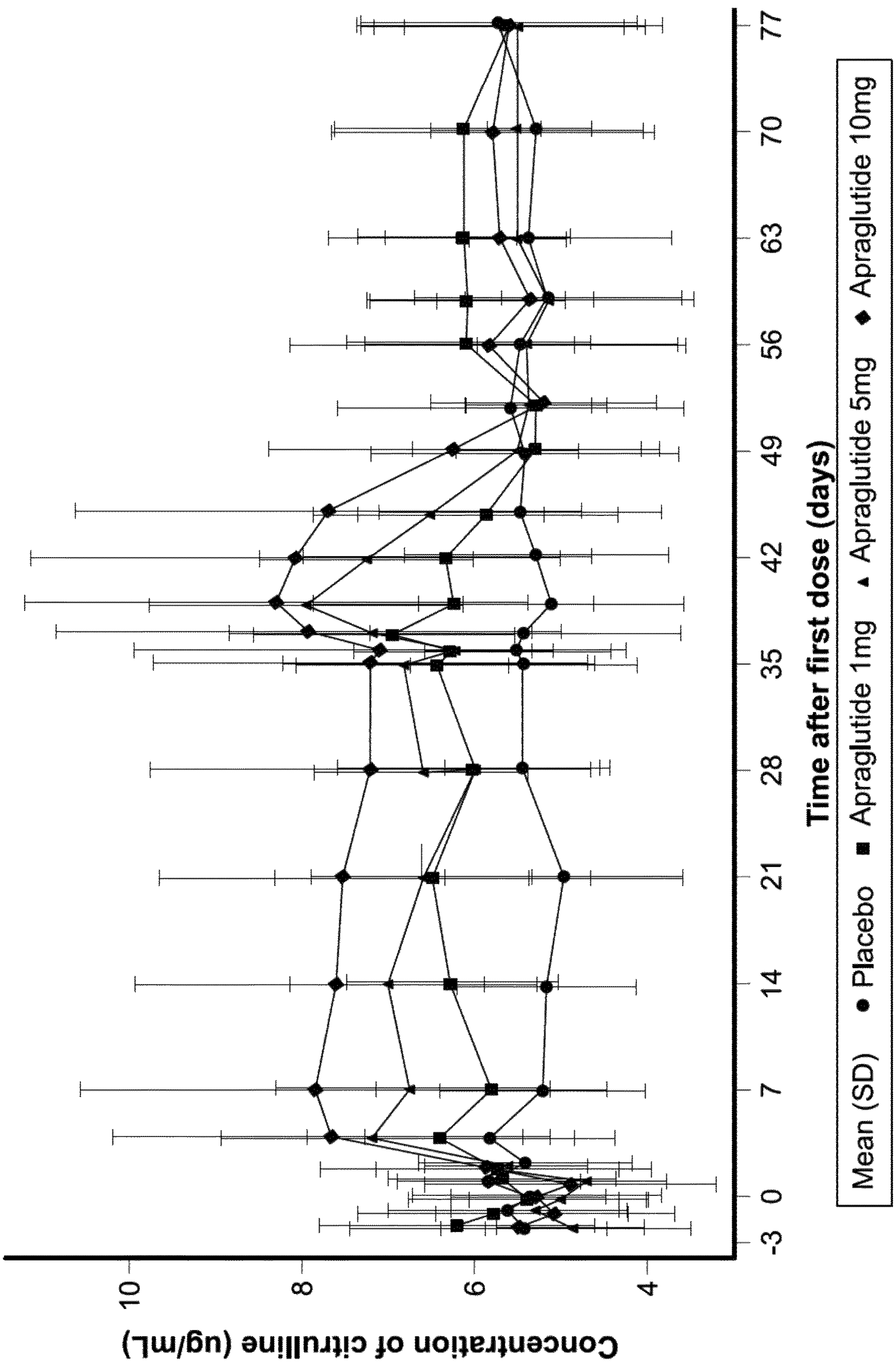

FIG. 18 is a graph showing plasma citrulline concentrations (ug/mL) as a function of time (days) after the first dose of apraglutide. SD=standard deviation; SC=subcutaneous. Data are arithmetic means (±SD). Weekly SC administrations of 1, 5 or 10 mg apraglutide were scheduled on days 1, 8, 15, 22, 29 and 36.

Figure 19:
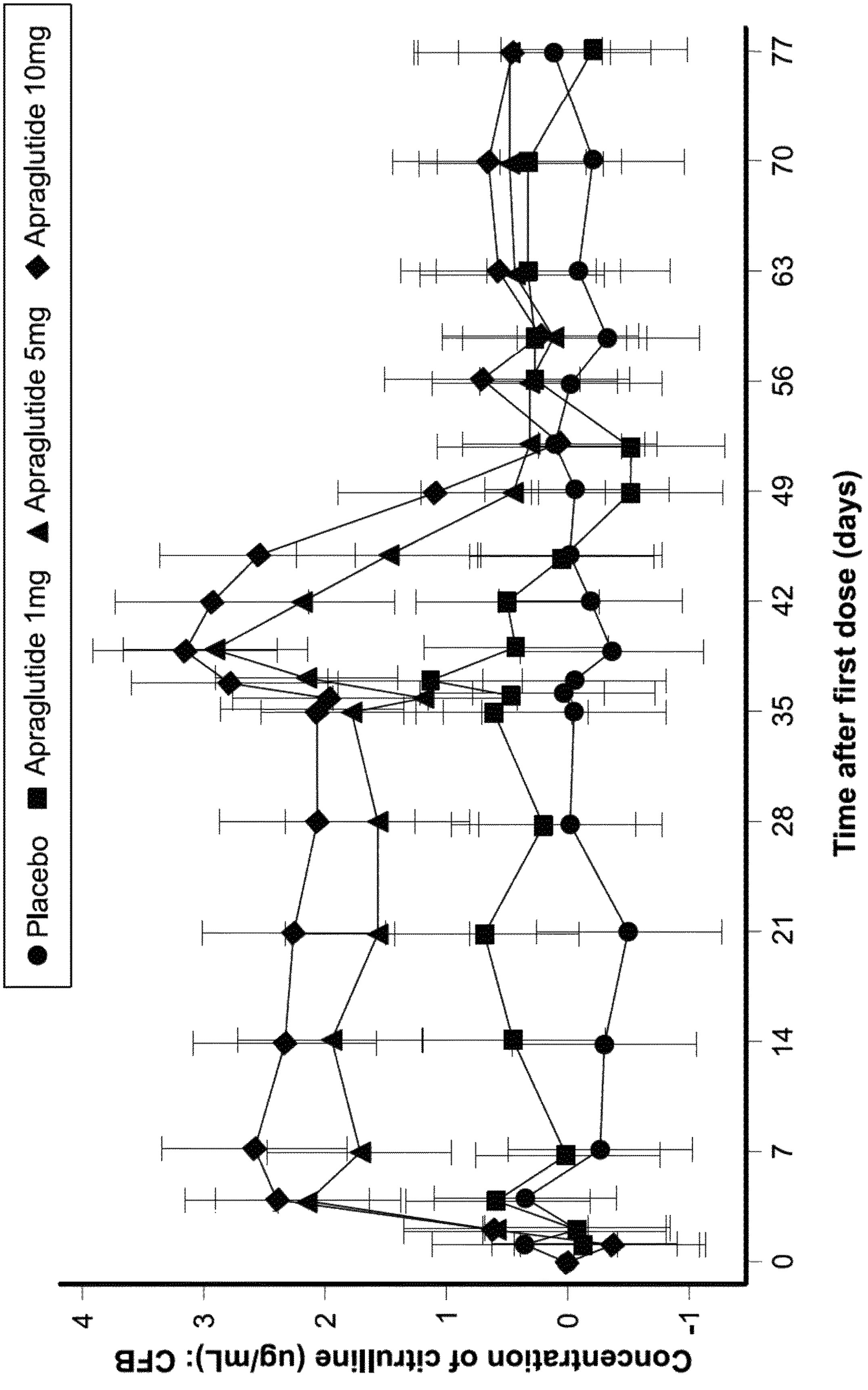

FIG. 19 is a graph showing the corresponding least square (LS) mean plot for change from baseline for plasma citrulline concentrations (ug/mL) as a function of time (days) after the first dose of apraglutide. CI=confidence interval; SC=subcutaneous. Data are estimated least square means (95% CI). Weekly SC administrations of 1, 5 or 10 mg apraglutide were scheduled on days 1, 8, 15, 22, 29 and 36.

Figure 20A:
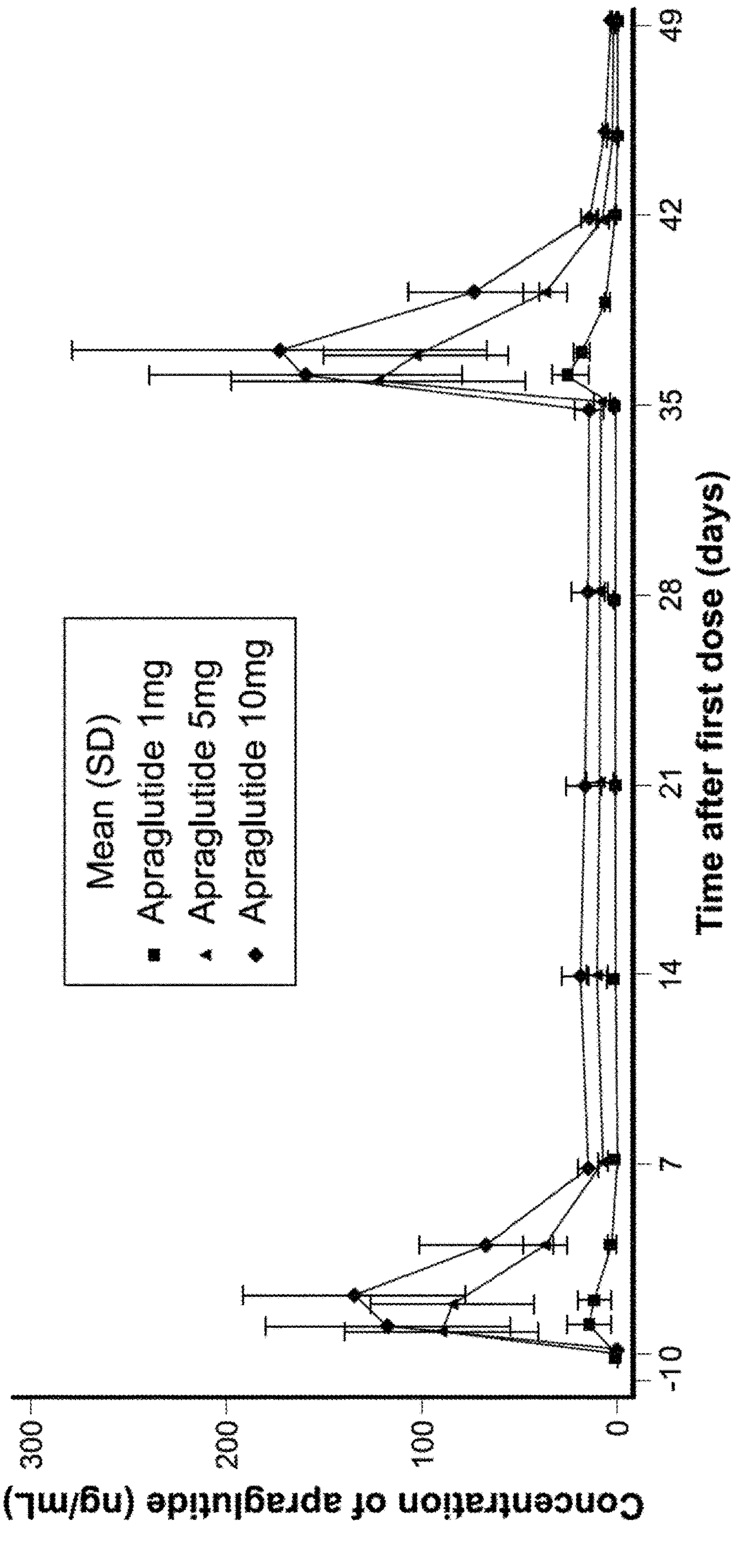

FIG. 20A is a graph showing plasma apraglutide concentration (ng/mL) as a function of time (days) after the first dose of apraglutide. SC=subcutaneous; SD=standard deviation. Weekly SC administrations of 1, 5 or 10 mg apraglutide were scheduled on day 1, 8, 15, 22, 29 and 36. Values below the limit of quantification (<1 ng/mL) were set to 0. Data per dose level are presented as arithmetic means±SD on a linear scale.

Figure 20B:
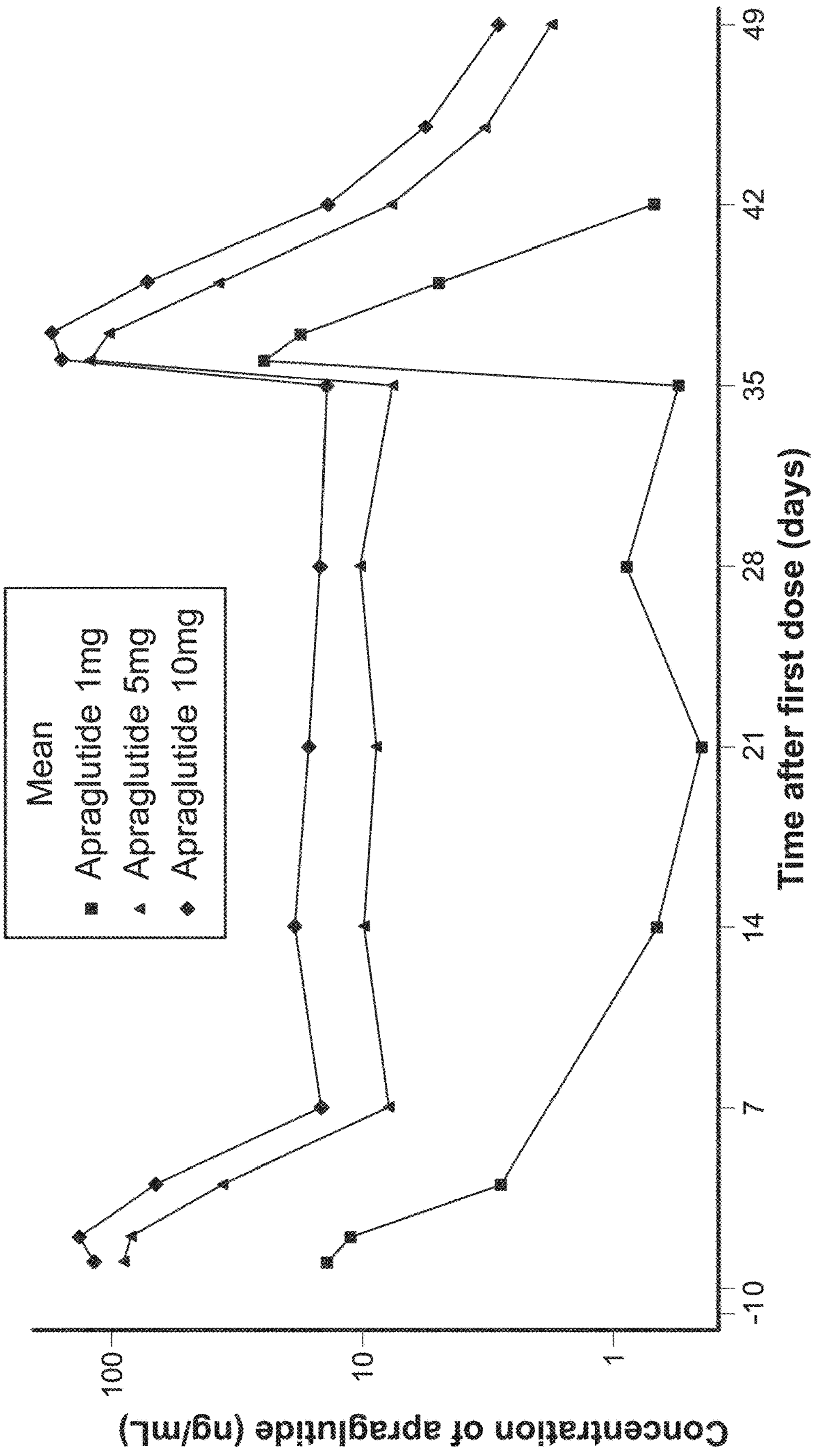

FIG. 20B is a graph showing plasma apraglutide concentration (ng/mL) as a function of time (days) after the first dose of apraglutide. SC=subcutaneous; SD=standard deviation. Weekly SC administrations of 1, 5 or 10 mg apraglutide were scheduled on day 1, 8, 15, 22, 29 and 36. Values below the limit of quantification (<1 ng/mL) were set to 0. Data per dose level are presented as arithmetic means±SD on a log scale.

Figure 21:
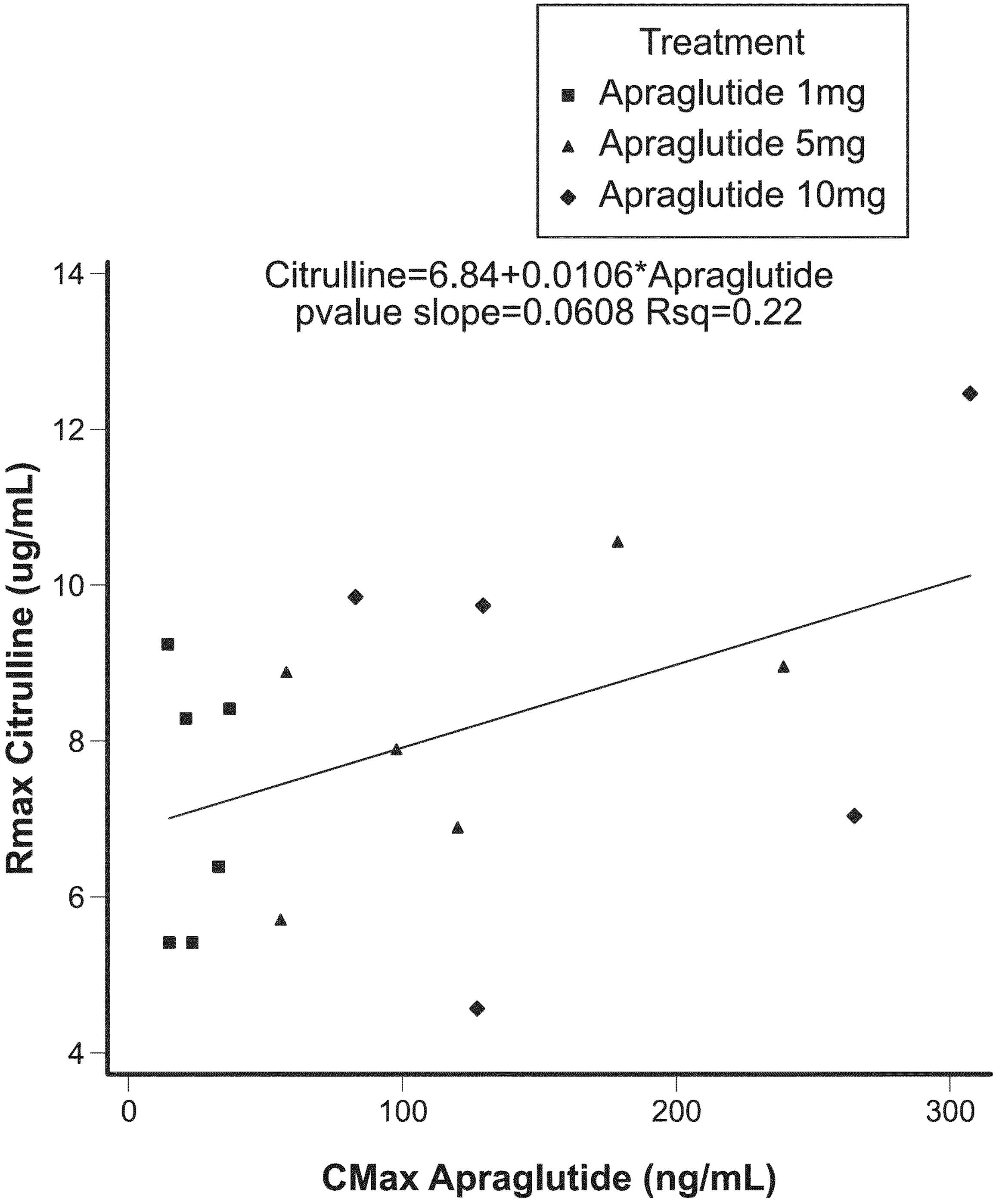

FIG. 21 is a graph showing individual Apraglutide $C_{max}$ values and corresponding citrulline $R_{max}$ values (ug/mL) by dose level in Week 6. $C_{max}$ Apraglutide (ng/mL); $C_{max}$=maximum concentration; $R_{max}$=maximum response. For the regression, the regression line, the equation, p-value of the slope and the R squared value are displayed.

Figure 22:
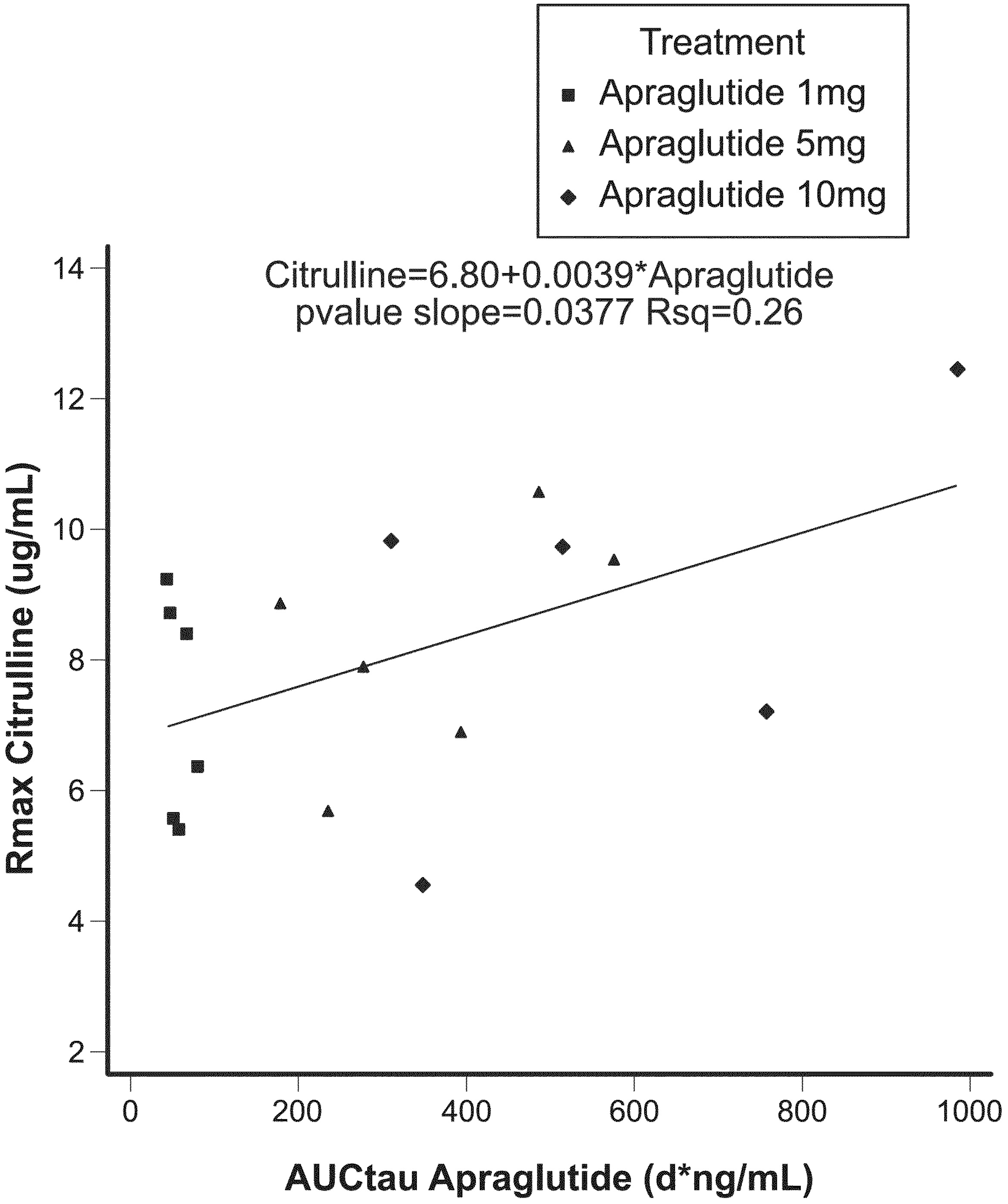

FIG. 22 is a graph showing individual Apraglutide $AUC_{tau}$ values and corresponding citrulline $R_{max}$ values (ug/mL) by dose level in Week 6. $AUC_{tau}$=area under the plasma concentration-time curve to the end of the treatment period of the corresponding dosing; $R_{max}$=maximum response. For the regression, the regression line, the equation, p-value of the slope and the R squared value are displayed.

Figure 23:
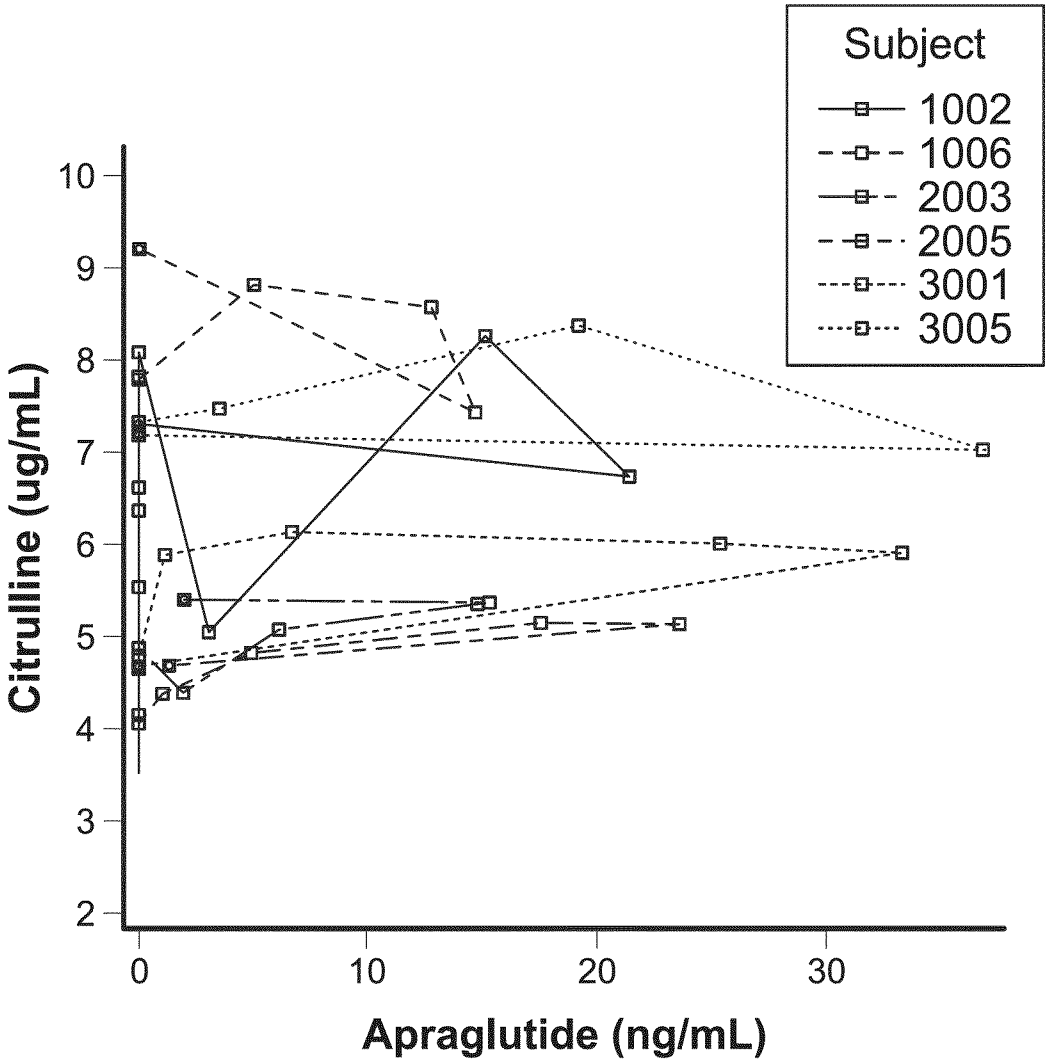

FIG. 23 is a correlation plot of individual apraglutide $AUC_{tau}$ values and corresponding citrulline $R_{max}$ values by dose level in Week 6. The black dot represents the assessment prior to the last dose and the line connects the subsequent assessments up to 2 weeks after the last dose.

Figure 24:
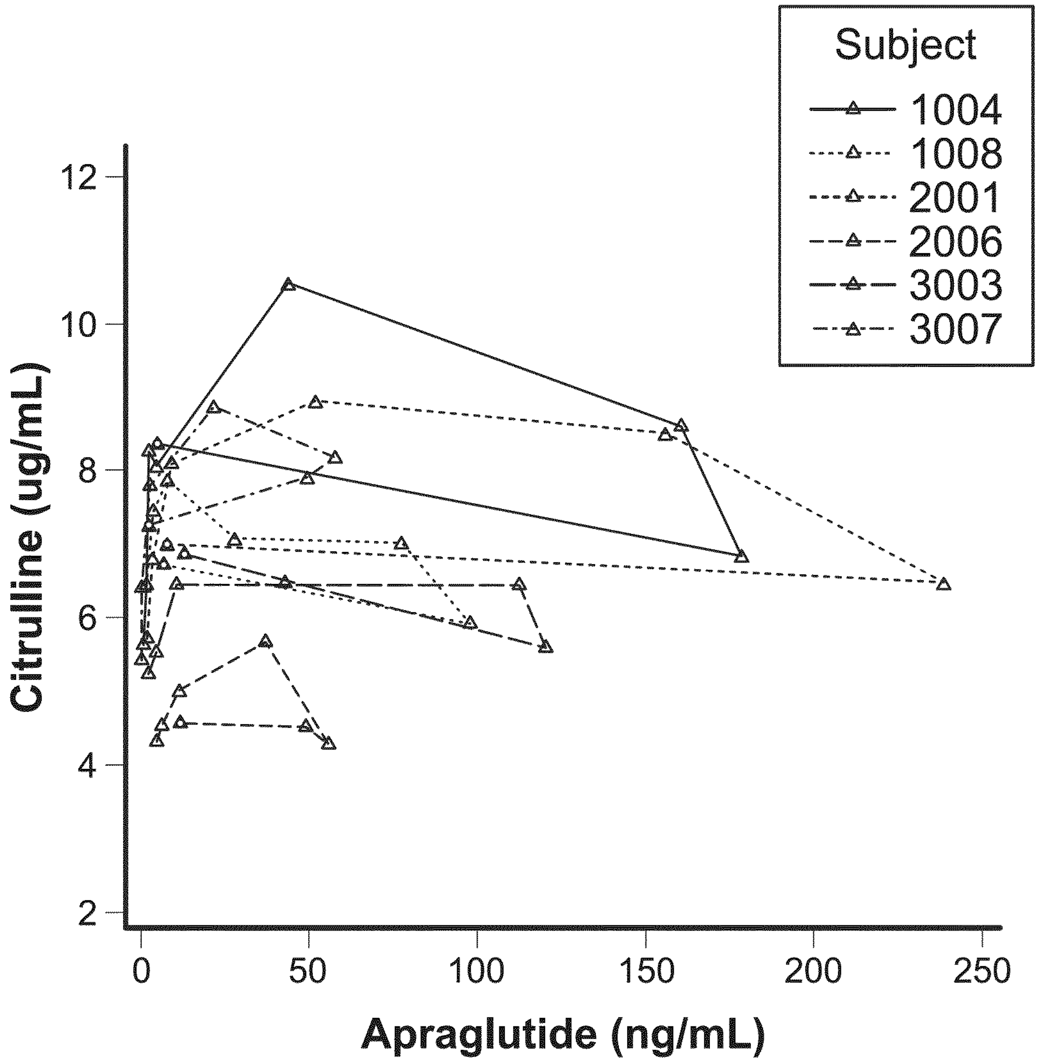

FIG. 24 is a correlation plot of all apraglutide concentrations and corresponding citrulline concentrations for each subject dosed with 1 mg in Week 6. The black dot represents the assessment prior to the last dose and the line connects the subsequent assessments up to 2 weeks after the last dose.

Figure 25:
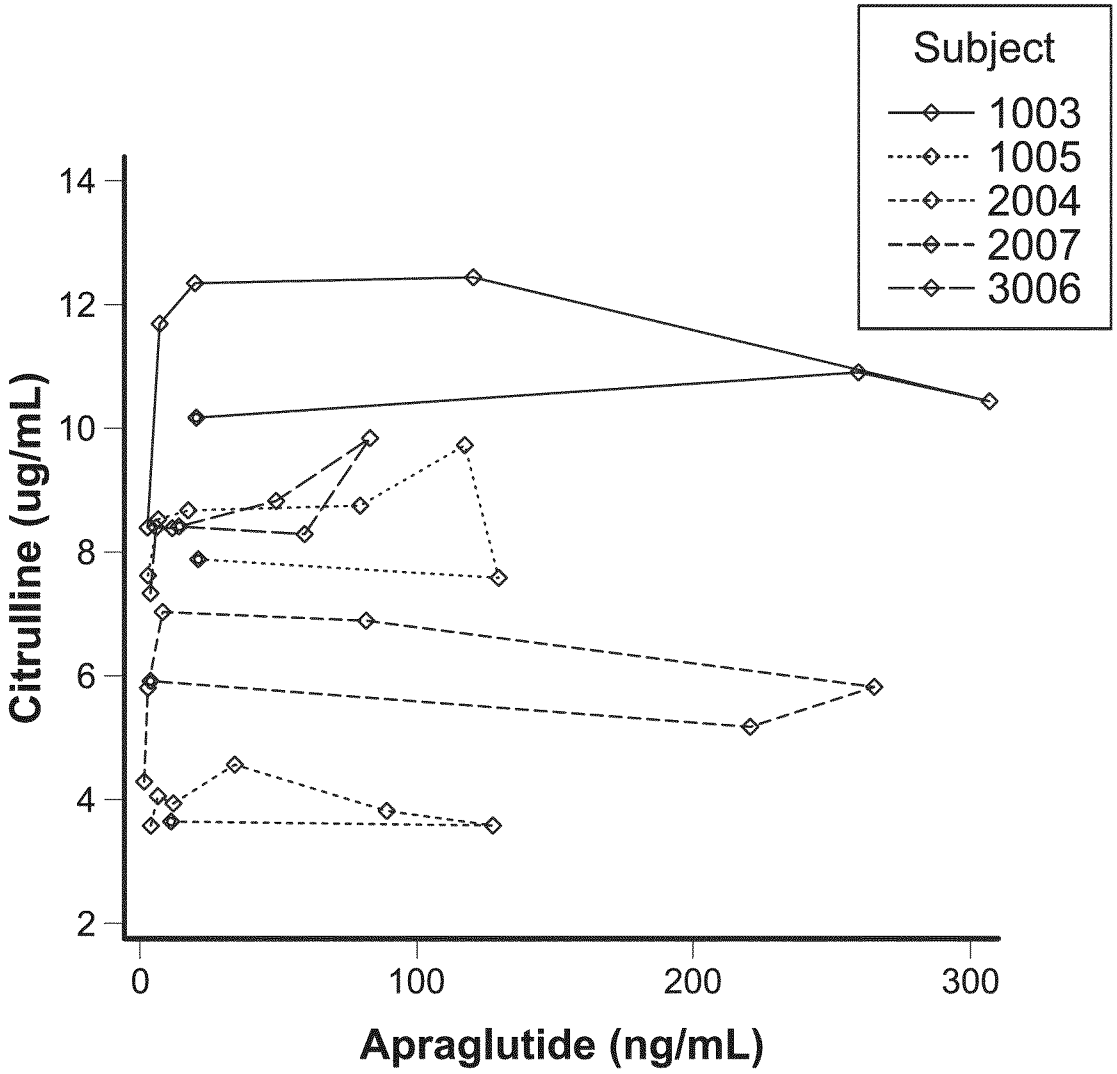

FIG. 25 is a correlation plot of all apraglutide concentrations and corresponding citrulline concentrations for each subject dosed with 5 mg in Week 6. The black dot represents the assessment prior to the last dose and the line connects the subsequent assessments up to 2 weeks after the last dose.

Figure 26A:
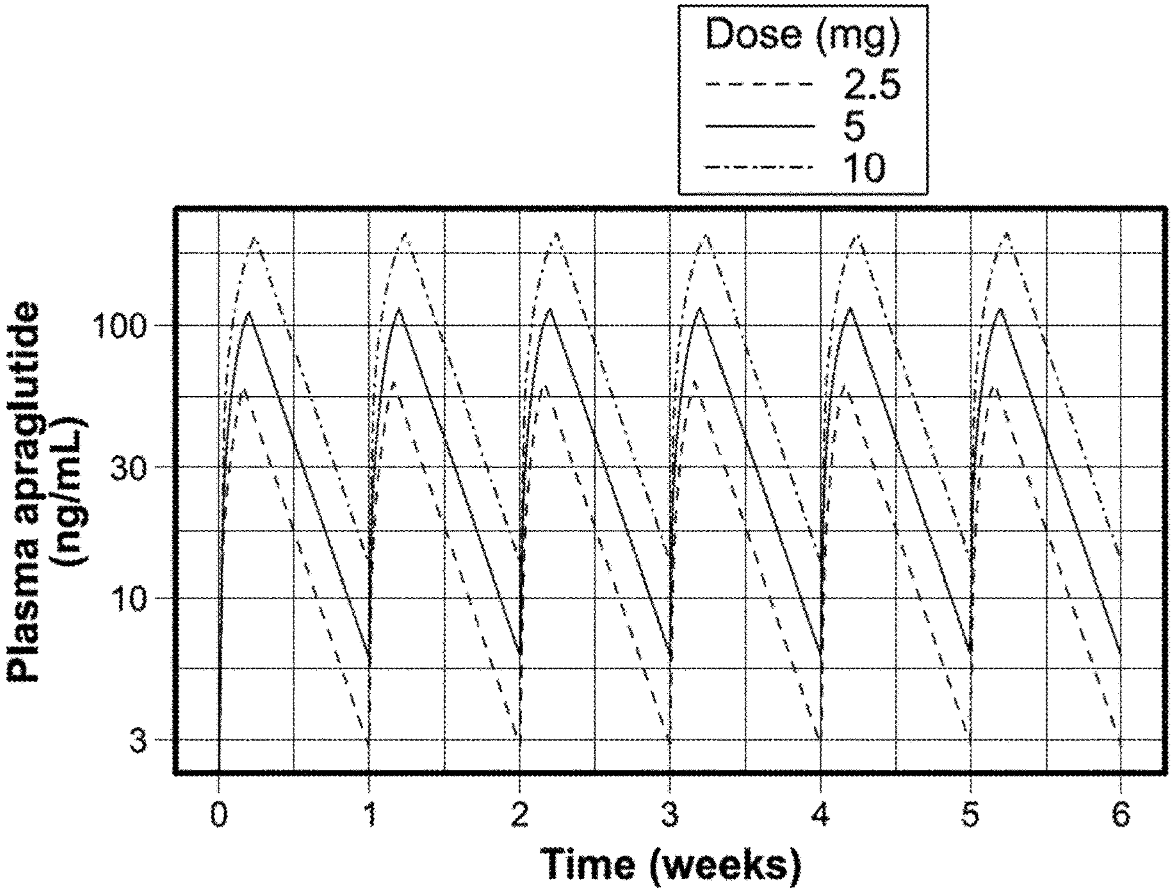

FIG. 26A is a graph showing predicted plasma apraglutide concentrations (ng/mL) for a 70 kg individual receiving weekly subcutaneous apraglutide 2.5, 5, or 10 mg.

Figure 26B:
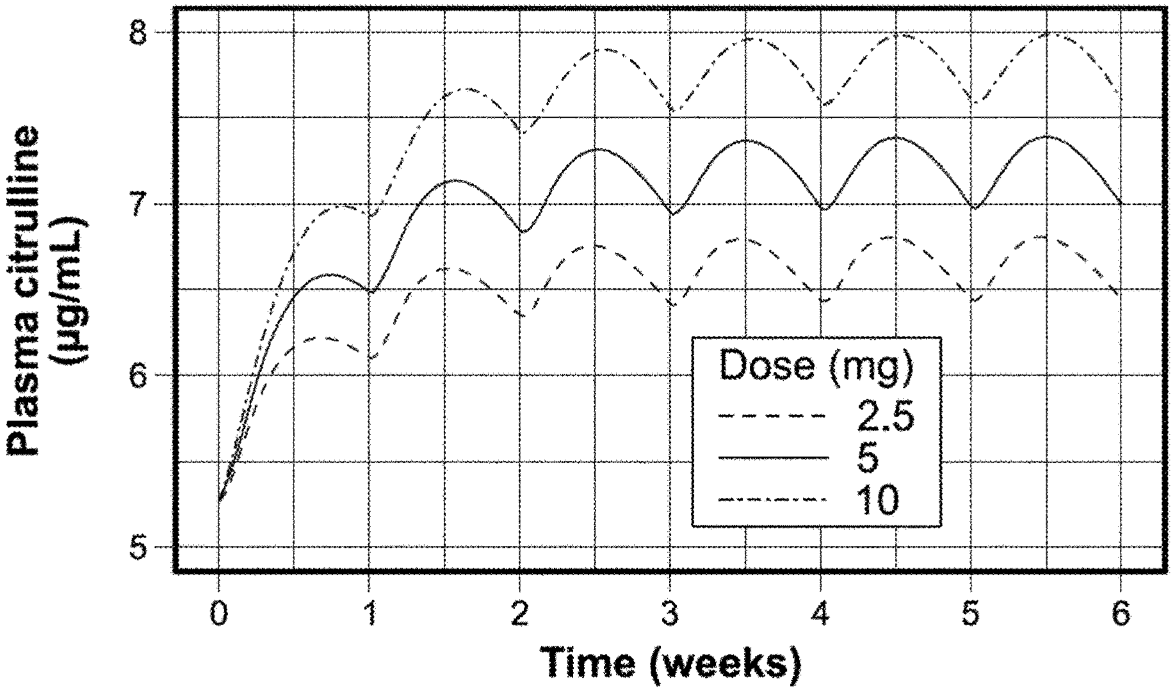

FIG. 26B is a graph showing predicted plasma citrulline concentrations (ug/mL) for a 70 kg individual receiving weekly subcutaneous apraglutide 2.5, 5, or 10 mg.

Figure 27:
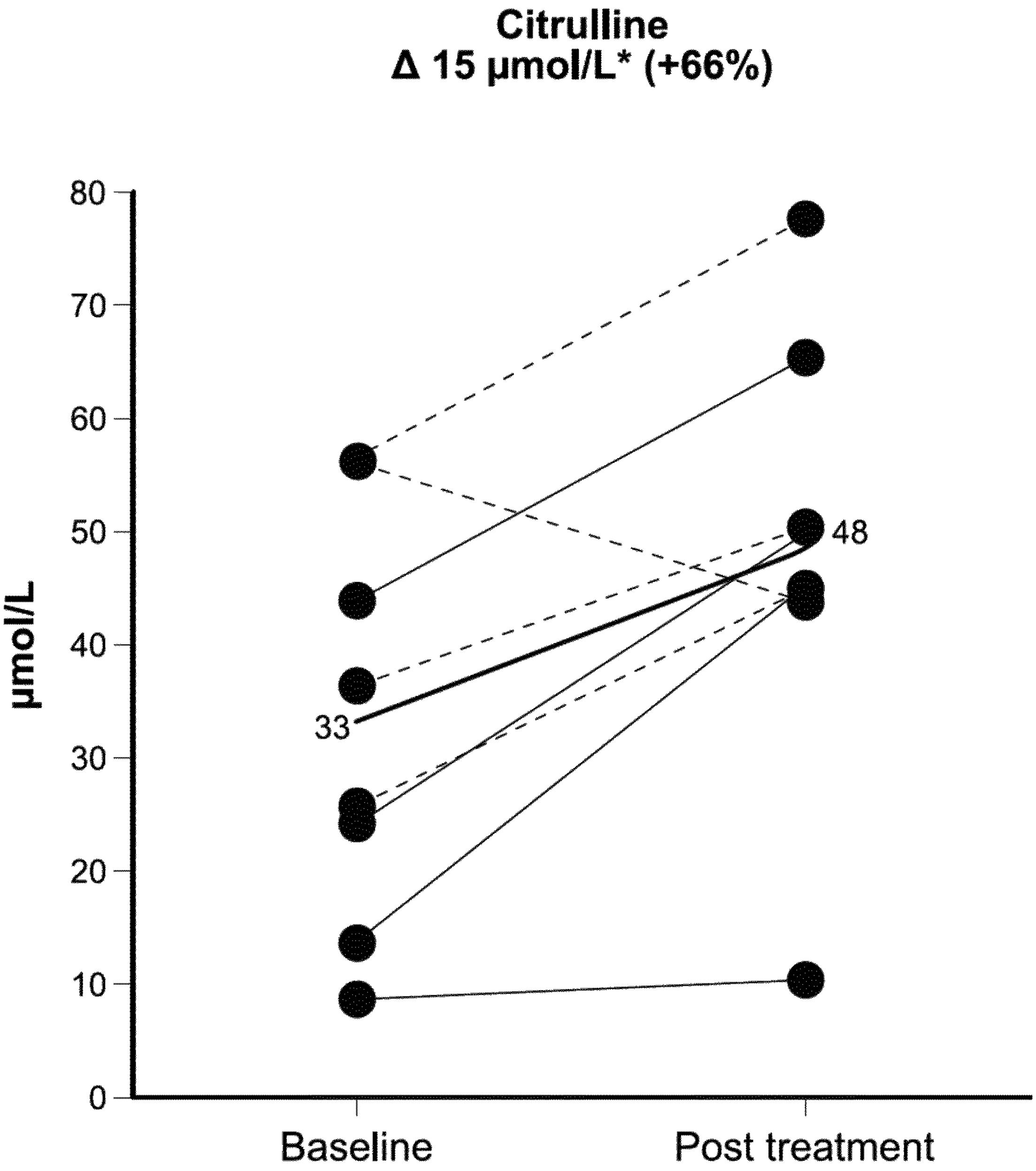

FIG. 27 is a graph showing individual and mean changes from baseline to post treatment in concentrations of plasma L-citrulline. Mean change from baseline was analyzed using a paired t-test. *$p<0.05$ Solid black line represents mean change, colored lines represent individual patients. Dotted line=SBS-II (intestinal insufficiency), solid line=SBS-IF (intestinal failure). A denotes the mean change from baseline.

Figure 28:
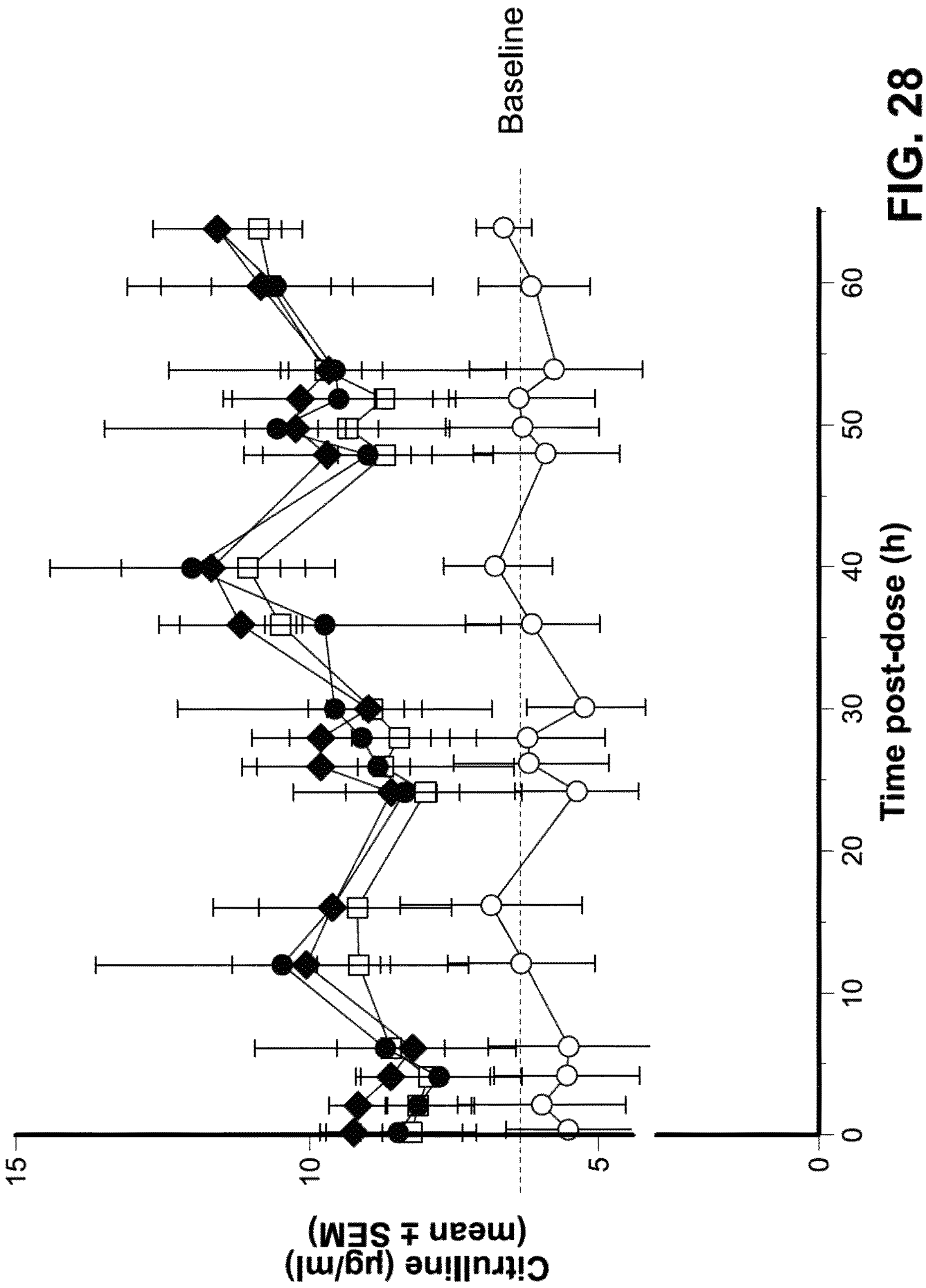

FIG. 28 is a graph showing citrulline plasma concentrations (ug/mL) following three weekly doses of apraglutide. Mean±standard error of the mean (SEM) are shown.

Figure 29:
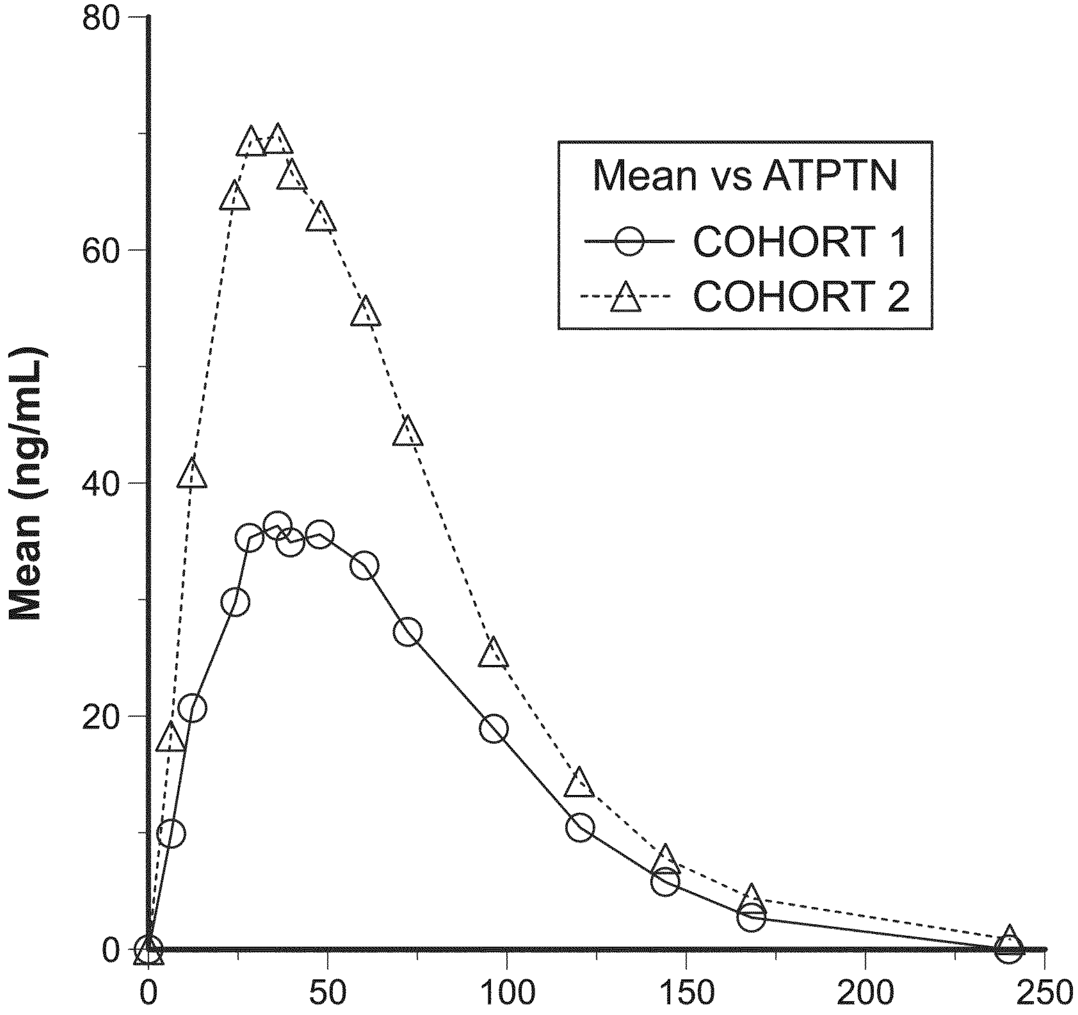

FIG. 29 is a graph showing plasma apraglutide concentration (ng/mL) as a function of time (hours) after the single subcutaneous 5 mg dose of apraglutide.

DETAILED DESCRIPTION

Short bowel syndrome (SBS) is a disabling malabsorptive disorder caused by extensive surgical bowel resection. Patients with extensive intestinal resections may suffer from disturbances in the gastrointestinal neuroendocrine feedback that regulate fluid and nutrient absorption. Disturbances include an impaired postprandial secretion of GLP-2, normally produced by L-cells in the terminal ileum and colon. Lack of GLP-2 might result in an accelerated gastrointestinal emptying, gastrointestinal hypersecretion, diminished intestinal blood flow, disturbed immunological and barrier function, and impaired mucosal growth. The consequent lack of intestinal adaptation contribute to the pathophysiological features of SBS, including frequent diarrheas or stoma emptyings, malnutrition, dehydration, electrolyte imbalances and weight loss. SBS is also associated with significant morbidity and mortality, and an impaired quality of life. In patients with SBS and intestinal failure (SBS-IF), parenteral support (PS), comprising any combination of intravenous fluids and/or parenteral nutrition, is required to maintain health and/or growth.

Long-term PS provision may result in serious complications such as catheter-related blood stream infections (CRBSI) and intestinal failure-associated liver disease (IF-ALD). In contrast to patients with SBS-IF, patients with SBS intestinal insufficiency (SBS-II) manage without PS due to their ability to compensate for their malabsorption by hyperphagia, metabolic adjustments and/or by pharmacological treatments. However, patients with SBS-II may be at risk of fluid and electrolyte imbalances which necessitate repeated hospital admissions for PS administration. Collectively, patients with SBS have an impaired quality of life, significant morbidity and mortality, and are health care expensive. Globally, SBS-IF is a neglected organ failure with limited treatment possibilities. Thus, identifying new treatments could improve disease awareness, morbidity and mortality, alleviate debilitating symptoms, and reduce patient treatment burden.

After surgical resection, the remnant bowel may undergo structural and functional changes to increase its absorptive capacity (commonly referred to as intestinal adaptation). The secretion of neuroendocrine peptides throughout the gastrointestinal tract contribute to this adaptation. The pathophysiological traits of SBS are often caused by disturbance in the neuroendocrine feedback mechanisms and lack of intestinal adaptation. This includes an impaired postprandial secretion of glucagon-like peptide-2 (GLP-2) which is produced by intestinal L-cells predominantly located in the terminal ileum and proximal colon.

Native GLP-2 has a short circulating half-life due to cleavage by dipeptidyl peptidase-IV (DPP4). Apraglutide is a next generation synthetically manufactured GLP-2 analogue with a molecular structure designed to provide long-lasting constant exposure and an increased half-life to at least 30 hours as compared with human GLP-2 and other GLP-2 analogues. Apraglutide differs from human GLP-2 by four amino acid substitutions and was identified through chemistry structure-activity relationship studies of lipophilic amino acid substitutions in positions 11 and 16 of [Gly2] hGLP-2 (1-33). In animal models, apraglutide promoted increase in intestinal length and weight, villus height and crypt depth. Pharmacokinetic (PK) and pharmacodynamic studies in animals have suggested that apraglutide may have a low clearance, long elimination half-life and a high plasma protein binding compared with other GLP-2 analogues. Therefore, apraglutide may be a candidate for a once weekly dosing regimen. Apraglutide treatment can potentially help patients to regain enteral autonomy or reduce PS requirements, improve symptoms of malabsorption, alleviate organ failures secondary to II and IF, and prevent patients with SBS-II from deteriorating into a situation of intermittent or chronic IF.

As used herein, the term "amino acid" includes both naturally occurring amino acids and non-naturally occurring amino acids. Unless otherwise stated, an amino acid is an L-amino acid. Unless otherwise stated, amino acid sequences are presented from the N-terminus to the C-terminus.

As used herein, the term "control," when used alone or in reference to a quantity or level, may refer to the level observed in a subject before administration of a treatment (e.g., an effective dose of a GLP-2 agonist), a level observed in a control subject or a population of subjects (including historically observed levels). When used in reference to a subject, a "control" may refer to the same subject before receiving a given treatment (e.g., an effective dose of a GLP-2 agonist), a similar subject who is not receiving any treatment for a given condition, or a similar subject who is receiving a treatment (e.g., surgery, wound care, and/or nutritional support) that does not comprise the given treatment (e.g., administration of an effective dose of a GLP-2 agonist).

As used herein, the term "GLP-2 agonist" refers collectively to an analog of a naturally occurring GLP-2 in a vertebrate, which elicits similar or comparable activity to the naturally occurring GLP-2, but is structurally altered, relative to a given vertebrate GLP-2, by at least one amino acid addition, deletion, substitution, modification, and/or by incorporation of one or more amino acid(s) with a blocking group. Such agonists preferably have an amino acid sequence at least 60%, at least 65%, at least 70%, at least 75%, at least 80%, at least 85%, at least 90%, or at least 95% identical to that of either GLP-2 or a fragment of GLP-2 having the same number of amino acid residues.

As used herein, the terms "patient" and "subject" are used interchangeably and refer to any subject for whom therapy is desired. In some embodiments, the subject is a mammal, e.g., a human or a non-human mammal. In some embodiments, the subject is a human being.

As used herein, the term "treatment" (also "treat" or "treating") refers to any administration of a therapeutic entity (e.g., a therapeutic compound or composition as described herein) that partially or completely reduces the need for parenteral support.

As used herein, the term "purity" is used to refer to purity as determined by chromatographic methods, more specifically by Ultra Performance Liquid Chromatography (UPLC) methods and/or High Performance Liquid Chromatography (HPLC) methods.

As used herein, the term "equivalent" of a substance (e.g. oxyma) is used to refer to a molar ratio of the substance, more specifically the number of moles of the substance that is to be reacted with one mole of another substance.

Any one of the embodiments and/or aspects described herein can be combined with any other embodiment and/or aspect described herein, and any number of embodiments and/or aspects can be combined.

GLP-2 agonists that can be used in methods of the present invention include, for example, those disclosed in International Patent Application No. W02006/117565 and U.S. Pat. No. 8,589,918, the entire contents of each which are herein incorporated by reference. The GLP-agonists apraglutide and related compounds (see, e.g., U.S. Pat. No. 8,589,918) have superior pharmacokinetic properties and are preferred for use in the present methods.

| SEQ ID NO: | Amino acid sequence |
|---|---|
| SEQ ID NO: 1 (GLP2) | His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp-OH |
| SEQ ID NO: 2 (Apraglutide) | **His-Gly-Asp-Gly-Ser-Phe-Ser-Asp-Glu-Nle-D-Phe-Thr-Ile-Leu-Asp-Leu-**Leu-Ala-Ala-Arg-Asp-Phe-Ile-Asn-Trp-Leu-Ile-Gln-Thr-Lys-Ile-Thr-Asp-$NH_2$ |

In preferred embodiments, the GLP-2 agonist is apraglutide, a peptide having the amino acid sequence of SEQ ID NO: 2, where Nle is norleucine and D-Phe is the D-amino acid phenylalanine.

Synthesis

Methods of preparing apraglutide have been described in the art and include solid phase peptide synthesis methods. See, for example, U.S. Pat. No. 8,580,918, which describes methods of preparing GLP-2 agonists including apraglutide. As opposed to previous apraglutide synthesis methods (e.g. the methods disclosed in U.S. Pat. No. 8,580,918) that were only able to achieve a purity of 93%, the present disclosure provides methods of making apraglutide that is substantially, e.g. ≥95% or ≥97%, pure, wherein the method still provides a high enough yield to be used in commercial manufacturing processes. In addition, U.S. Pat. No. 8,580,918 discloses the ammonium salt of apraglutide. Disclosed herein is the synthesis of a preferred salt of apraglutide, the sodium salt.

The apraglutide production process is based on solid phase peptide synthesis (SPPS) using Fmoc (9-fluorenylmethyloxycarbonyl) strategy. The amino acid sequence is built stepwise from C-terminus by successive cycles of Fmoc deprotection and coupling of the next Fmoc amino acid. The novel synthesis method of apraglutide has a number of improvements described below. Fmoc-Rink-amide-MBHA (MethylBenzHydril Amine)-Resin is used, with the link between the peptide and the resin performed via a Knorr linker. After Fmoc deprotection the Piperidine/DMF (N, N dimethylformamide) washes are done with use of Oxyma (Ethyl [hydroxyamino] cyanoacetate) in order to reduce levels of oxidation impurities. Two DIC (Diisopropylcarbodiimide) additions are implemented in order to decrease the coupling time. After each amino acid coupling reaction, completeness is controlled by a semi-quantitative Kaiser test based on revealing the unreacted amines. After assembly and the last Fmoc group deprotection, the peptide resin is washed with IPA (Isopropanol) and dried under vacuum. With use of novel synthesis process, the overall coupling time is reduced by around 25% compared to initial condition, with no impact on crude peptide HPLC (High Performance Liquid Chromatography) purity and process yield.

After completion of peptide synthesis, cleavage of peptide from resin is done by treatment with TFA (Trifluoroacetic acid)/$H_2O$/anisole mixture at room temperature, under nitrogen. Cleaved peptide is separated from resin by filtration and processed further in the improved downstream purification steps to produce sodium salt of apraglutide with HPLC purity ≥97%.

The improved version of apraglutide synthesis process (Process B; depicted in FIGS. 2A and 2B) comprises a primary purification by RP-HPLC (C18) chromatography in TFA-based mobile phases ($H_2O$/acetonitrile) to ≥90% purity with pH of fractions adjusted using sodium bicarbonate ($NaHCO_3$), followed by secondary purification by RP-HPLC (C18) in $NaHCO_3$ mobile phases ($H_2O$/acetonitrile) to ≥97% purity, and followed by desalting/buffer exchange by RP-HPLC (C18) in sodium acetate (NaOAc)/$H_2O$/acetonitrile mobile phases. The product-containing fractions are pooled and lyophilized to produce sodium salt of apraglutide with ≥97% purity. The improved versions of the apraglutide synthesis process described herein are able to provide highly pure apraglutide (e.g. ≥95% or ≥97% pure), while still maintaining yields that are suitable for large-scale commercial manufacture of apraglutide. As would be appreciated by the skilled artisan, methods of producing ultrapure compounds typically suffer from low yields, making their use in commercial manufacturing infeasible. Surprisingly, the apraglutide synthesis methods described herein not only provide highly pure apraglutide, but also exhibit yields that are suitable for use in commercial manufacturing contexts.

The present disclosure provides a method of making a GLP-2 analog peptide comprising:

a) performing solid phase peptide synthesis (SPPS) to synthesize the GLP-2 analog peptide on a resin;
b) cleaving the synthesized GLP-2 analog peptide off the resin and deprotecting the side chains of the synthesized GLP-2 analog peptide by treating the resin with a solution comprising trifluoroacetic acid (TFA), water, and anisole;

c) purifying the synthesized GLP-2 analog peptide using preparative reversed-phase high performance liquid chromatography (RP-HPLC);

d) further purifying the product from step (c) using a second preparative RP-HPLC to produce a purified peptide solution (and optionally a third preparative RP-HPLC where desalting and buffer exchange occurs);

e) freeze-drying the purified peptide solution to produce a purified peptide powder; and f) packaging the purified peptide powder under argon.

The present disclosure provides a method of making a GLP-2 analog peptide comprising: performing SPPS to synthesize the GLP-2 analog peptide on a resin, wherein the resin is 4-Methylbenzhydrylamine (MBHA) resin.

The present disclosure provides a method of making a GLP-2 analog peptide comprising: performing SPPS to synthesize the GLP-2 analog peptide on a resin, wherein the SPPS comprises washing the resin with a solution comprising DMF and oxyma.

The present disclosure provides a method of making a GLP-2 analog peptide comprising: performing SPPS to synthesize the GLP-2 analog peptide on a resin, wherein SPPS comprises a coupling step performed by contacting the resin with two amounts of a solution comprising DIC and oxyma, and wherein the amounts are contacted 30 minutes apart.

The present disclosure provides a method of making a GLP-2 analog peptide comprising: purifying the synthesized GLP-2 analog peptide by contacting the peptide with a solution comprising water, acetonitrile (ACN), and ammonium hydroxide ($NH_4OH$) for the extraction of the crude peptide from the cleaved peptide resin mixture and omitting the subsequent acidification step.

The present disclosure provides a method of making a GLP-2 analog peptide comprising: purifying the synthesized GLP-2 analog peptide by RP-HPLC using a solution comprising 0.05% TFA, water, and acetonitrile as the eluent and adjusting the pH of the purified peptide fractions to about pH 7.9 using 0.1% (acetic acid) AcOH in water.

The present disclosure provides a method of making a GLP-2 analog peptide comprising: purifying the synthesized GLP-2 analog peptide with a second purification by RP-HPLC using a solution comprising 0.05M sodium bicarbonate ($NaHCO_3$), water, and acetonitrile as the eluent.

The present disclosure provides a method of making a GLP-2 analog peptide comprising: performing an HPLC purification using a 1.5 mM NaOAc/$H_2O$/ACN solution as the mobile phase.

In some aspects of the methods of the present disclosure, step (a) comprises:

i) preparing a resin on which the SPPS will be performed;

ii) performing an initial Fmoc deprotection followed by a coupling reaction to add a first Fmoc-protected amino acid to the resin, thereby forming a protected peptide on the resin;

iii) performing an Fmoc deprotection reaction followed by a coupling reaction to append at least one Fmoc-protected amino acid to the protected peptide;

iv) repeating step iii until the GLP-2 analog peptide is synthesized on the resin, wherein a Fmoc-protected and side-chain protected GLP-2 analog peptide is linked to the resin, and wherein the peptide comprises the amino acid sequence: L-histidyl-glycyl-L-aspartyl-glycyl-L-seryl-L-phenylalanyl-L-seryl-L-aspartyl-L-glutamyl-L-norleucyl-D-phenylalanyl-L-threonyl-Lisoleucyl-L-leucyl-L-aspartyl-L-leucyl-L-leucyl-L-alanyl-L-alanyl-L-arginyl-L-aspartyl-L-phenylalanyl-L-isoleucyl-L-asparaginyl-Ltryptophanyl-L-leucyl-L-isoleucyl-L-glutaminyl-L-threonyl-L-lysyl-L-isoleucyl-L-threonyl-Laspartic acid amide.

v) performing an Fmoc deprotection reaction to produce a side-chain protected GLP-2 analog peptide linked to the resin; and vi) drying the side-chain protected GLP-2 analog peptide linked to the resin.

In some aspects of the methods of the present disclosure, step (a)(i) comprises:

(a1) washing the resin with a solution comprising dimethylformamide (DMF) and N,N-Diisopropylethylamine (DIEA) at 5 mL of solution per gram of resin under an $N_2$ atmosphere;

(b1) coupling a Rink amide linker to the resin in a solution comprising 2-(1H-benzotriazol-1-yl)-1,1,3,3-tetramethyluronium hexafluorophosphate, Hexafluorophosphate Benzotriazole Tetramethyl Uronium (HBTU), DIEA and Hydroxybenzotriazole (HOBt) in DMF;

(c1) washing the product formed in step (b1) with DMF (d1) performing a reduction reaction by contacting the resin with a solution comprising acetic anhydride ($Ac_2O$) and DIEA in DMF; and (e1) washing the product formed in step (d1) with DMF.

In some aspects of the methods of the present disclosure, the resin is Methylbenzhydrylamine resin.

In some aspects of the methods of the present disclosure, the product of steps (a)(i)(a1)-(a)(i)(e1) is a Fmoc-Rink-amide-MBHA resin.

In some aspects of the methods of the present disclosure, step (c1) and/or step (e1) comprises washing the product three times at a ratio of 5 milliliters of DMF to each gram of resin.

In some aspects of the methods of the present disclosure, a coupling test may be performed between steps (d1) and (e1).

In some aspects of the methods of the present disclosure, a Kaiser test is performed to determine whether completion of the coupling was achieved.

In some aspects of the methods of the present disclosure, the product upon completion of step (a)(i)(e1) is: Fmoc-His(Trt)-Gly-Asp(OtBu)-TmbGly-Ser(tBu)-Phe-Ser(tBu)-Asp(OtBu)-Glu(OtBu)-Nle-DPhe-Thr(tBu)-Ile-Leu-Asp(OtBu)-Leu-Leu-Ala-Ala-Arg(Pbf)-Asp(OtBu)-Phe-Ile-Asn(Trt)-Trp(Boc)-Leu-Ile-Gln(Trt)-Thr($\psi^{Me,Me}$pro)-Lys(Boc)-Ile-Thr(tBu)-Asp(OtBu)-Rink-amide-MBHA-Resin.

In some aspects of the methods of the present disclosure, performing an Fmoc deprotection reaction followed by a coupling reaction comprises:

(a2) treating the resin with a solution comprising piperidine in DMF;

(b2) washing the resin with DMF;

(c2) contacting the resin with at least one Fmoc-protected amino acid and a solution comprising diisopropylcarbodiimide (DIC) and ethyl cyanohydroxyiminoacetate (oxyma) in DMF, thereby coupling the at least one Fmoc-protected amino acid; and (d2) washing the product formed in step (c2) with DMF.

In some aspects of the methods of the present disclosure, the solution comprising piperidine in DMF is a 35% piperidine solution in DMF.

In some aspects of the methods of the present disclosure, treating the resin with the solution comprising piperidine in DMF is performed by a 3 minute wash of the resin with the solution comprising piperidine in DMF, followed by a second 3 minute wash of the resin with the solution comprising piperidine in DMF, followed by a 10 minute wash of the resin with the solution comprising piperidine in DMF.

In some aspects of the methods of the present disclosure, the solution comprising piperidine in DMF is a 20% piperidine solution in DMF.

In some aspects of the methods of the present disclosure, the treatment of the resin with the solution comprising piperidine in DMF is performed by a 15 minute wash of the resin with the solution comprising piperidine in DMF, followed by a second 15 minute wash of the resin with the solution comprising piperidine in DMF.

In some aspects of the methods of the present disclosure, the washes are performed at a ratio of 5 milliliters of solution comprising piperidine in DMF to each gram of resin.

In some aspects of the methods of the present disclosure, washing the resin in step (b2) comprises performing a first DMF wash at a ratio of 15 milliliters of DMF to each gram of resin, followed by a second DMF wash at a ratio of 5 milliliters of DMF to each gram of resin.

In some aspects of the methods of the present disclosure, washing the resin in step (b2) comprises:

i) washing the resin with DMF; and
ii) washing the resin with a solution comprising DMF and oxyma.

In some aspects of the methods of the present disclosure, the solution comprising DMF and oxyma comprises 2 equivalents of oxyma.

In some aspects of the methods of the present disclosure, performing an Fmoc deprotection reaction of residue $Asp^3$ comprises treating the resin with a solution comprising piperidine and Oxyma in DMF.

In some aspects of the methods of the present disclosure, the solution comprising piperidine and Oxyma in DMF is a 10% piperidine and 2% Oxyma solution in DMF.

In some aspects of the methods of the present disclosure, the solution comprising piperidine and Oxyma in DMF is a 5% piperidine and 1% Oxyma solution in DMF.

In some aspects of the methods of the present disclosure, the solution comprising piperidine and Oxyma in DMF is a 15% piperidine and 3% Oxyma solution in DMF.

In some aspects of the methods of the present disclosure, the solution comprising piperidine and Oxyma in DMF is a 20% piperidine and 4% Oxyma solution in DMF.

In some aspects of the methods of the present disclosure, the solution comprising piperidine and Oxyma in DMF is a 25% piperidine and 5% Oxyma solution in DMF.

In some aspects of the methods of the present disclosure, the solution comprising piperidine and Oxyma in DMF is a 30% piperidine and 6% Oxyma solution in DMF.

In some aspects of the methods of the present disclosure, the treatment of the resin with the solution comprising piperidine and Oxyma in DMF is performed by a 15 minute wash of the resin with the solution comprising piperidine and Oxyma in DMF, followed by a second 30 minute wash of the resin with the solution comprising piperidine and Oxyma in DMF.

In some aspects of the methods of the present disclosure, step (c2) comprises:

i) contacting the resin with at least one Fmoc-protected amino acid and a solution comprising DIC and oxyma in DMF; and
ii) contacting the resin with a second amount of a solution comprising DIC.

In some aspects of the methods of the present disclosure, the resin is contacted with the second amount of a solution comprising DIC for about 10, 15, 20, 25, 30, 35, 40, 45, or 50 minutes after contacting the resin with the at least one Fmoc-protected amino acid.

In some aspects, the at least one protected amino acid is a di-peptide comprising Boc-His(Trt)-Gly-OH.

In some aspects, the at least one protected amino acid is a di-peptide comprising Fmoc-His(Trt)-Gly-OH.

In some aspects, the dipeptide is preactivated for 10 minutes, 30 minutes, 45 minutes, 60 minutes, 2 hours, 3 hours, or 4 hours before coupling the dipeptide.

In some aspects, the dipeptide is preactivated at 5° C.±2° C., 10° C.±2° C., 15° C.±2° C., 20° C.±2° C., 25° C.±2° C., 30° C.±2° C., or 35° C.±2° C. before coupling the dipeptide.

In some aspects, the dipeptide is preactivated in a solution comprising Boc-His (Trt)-Gly-OH/Oxyma/DIC 2.5 mmol/2.5 mmol/2.5 mmol in 7 mL DMF before coupling the dipeptide.

In some aspects of the methods of the present disclosure, step (c2) comprises:

i) contacting the resin with at least one Fmoc-protected amino acid and a solution comprising DIC and oxyma in DMF; and
ii) contacting the resin with a second amount of a solution comprising DIC and oxyma.

In some aspects of the methods of the present disclosure, the second amount of a solution comprising DIC and oxyma is contacted with the resin about 30 minutes after contacting the resin with the at least one Fmoc-protected amino acid.

In some aspects of the methods of the present disclosure, in step (c2), the at least one Fmoc-protected amino acid is provided at a concentration of 1, 2, 3, 4, or 5 equivalents.

In some aspects of the methods of the present disclosure, in step (c2), the DIC is provided at a concentration of 1, 2, 3, 4, or 5 equivalents and the oxyma is provided at a concentration of 1, 2, 3, 4, or 5 equivalents.

In some aspects of the methods of the present disclosure, in step (c2), the at least one Fmoc-protected amino acid is Fmoc-Gln(Trt)-Thr($\psi^{Me,Me}$pro)-OH.

In some aspects of the methods of the present disclosure, in step (c2), Fmoc-Gln(Trt)-Thr($\psi^{Me,Me}$pro)-OH is provided at a concentration of 1, 1.5, 2, 2.5, 3, 3.5, 4, 4.5, or 5 equivalents.

In some aspects of the methods of the present disclosure, the method further comprises between step (b2) and step (c2), performing a test for residual piperidine by measuring the amount of piperidine.

In some aspects of the methods of the present disclosure, if the amount of piperidine measured is greater than 10, 100, 200, 300, 400, 500, 600, 700, 800, 900, or 1000 ppm, the resin is washed again with DMF and/or a solution comprising DMF and oxyma.

In some aspects of the methods of the present disclosure, a coupling test is performed between step (c) and step (d).

In some aspects of the methods of the present disclosure, the coupling test is a ninhydrin assay.

In some aspects of the methods of the present disclosure, step a(v) comprises:

(a3) treating the resin with a solution comprising piperidine in DMF;
(b3) washing the resin with DMF;
(c3) washing the resin with isopropanol.

In some aspects of the methods of the present disclosure, washing the resin in step (b3) comprises:

i) washing the resin with DMF; and
ii) washing the resin with a solution comprising DMF and oxyma.

In some aspects of the methods of the present disclosure, washing the resin with isopropanol in step (c3) comprises washing the resin five times with isopropanol, wherein each wash is performed at a ratio of 5 milliliters of isopropanol for each gram of resin.

In some aspects of the methods of the present disclosure, the product upon completion of step (a)(v) is a protected peptide on resin comprising: H-His(Trt)-Gly-Asp(OtBu)-TmbGly-Ser(tBu)-Phe-Ser(tBu)-Asp(OtBu)-Glu(OtBu)-Nle-DPhe-Thr(tBu)-Ile-Leu-Asp(OtBu)-Leu-Leu-Ala-Ala-Arg(Pbf)-Asp(OtBu)-Phe-Ile-Asn(Trt)- Trp(Boc)-Leu-Ile-Gln(Trt)-Thr($\psi^{Me,Me}$pro)-Lys(Boc)-Ile-Thr(tBu)-Asp(OtBu)-Rink-amide-MBHA-Resin.

In some aspects of the methods of the present disclosure, the solution comprising TFA, water and anisole is a solution comprising TFA, water and anisole at a ratio of 95:2.5:2.5, TFA:water:anisole.

In some aspects of the methods of the present disclosure, the solution comprising TFA, water and anisole is a solution comprising TFA, water and anisole at a ratio of 90:5:5, TFA:water:anisole.

In some aspects of the methods of the present disclosure, the solution comprising TFA, water and anisole is a solution comprising TFA, water and anisole at a ratio of 80:10:10, TFA:water:anisole.

In some aspects of the methods of the present disclosure, the solution comprising TFA, water and anisole is a solution comprising TFA, water and anisole at a ratio of 70:15:15, TFA:water:anisole.

In some aspects of the methods of the present disclosure, step (b) further comprises precipitating and washing the cleaved and deprotected GLP-2 analog peptide using tert-butyl methyl ether (MTBE).

In some aspects of the methods of the present disclosure, the product upon completion of step (b) is: H-His-Gly-Asp-Gly-Ser$^{5}$-Phe-Ser-Asp-Glu-NLe$^{10}$-DPhe-Thr-Ile-Leu-Asp$^{15}$-Leu-Leu-Ala-Ala-Arg$^{20}$-Asp-Phe-Ile-Asn-Trp$^{25}$-Leu-Ile-Gln-Thr-Lys$^{30}$-Ile-Thr-Asp-$NH_2$.

In some aspects of the methods of the present disclosure, step (c) comprises:

(i) contacting the product of step (b) with a solution comprising water, acetonitrile and $NH_4OH$;

(ii) purifying the synthesized GLP-2 analog peptide using preparative reversed-phase high performance liquid chromatography (RP-HPLC).

In some aspects, the solution of step (c) (i) comprising water and acetonitrile comprises a mixture of $H_2O$/ACN in an 80:20 ratio in ammonia buffer.

In some aspects, the solution of step (c) (i) comprising water and acetonitrile comprises a mixture of $H_2O$/ACN in a 70:30 ratio in ammonia buffer.

In some aspects, the solution of step (c) (i) comprising water and acetonitrile comprises a mixture of $H_2O$/ACN in a 90:10 ratio, 80:20 ratio, 70:30 ratio, 60:40 ratio, 50:50 ratio, or 40:60 ratio in ammonia buffer.

In some aspects, the solution of step (c) (i) comprising water and acetonitrile is adjusted to target pH 7, pH 8, pH 9, pH 10, or pH 11.

In some aspects, the solution of step (c) (i) comprising water and acetonitrile is adjusted to target pH≥7.

In some aspects, the solution of step (c) (i) comprising water and acetonitrile is adjusted to target pH 8.0±0.1.

In some aspects, the solution of step (c) (i) comprising water and acetonitrile is adjusted to target pH 8.0±0.1, ±0.2, ±0.3, ±0.4, ±0.5, ±0.6, ±0.7, ±0.8, or ±0.9.

In some aspects, the solution of step (c) (i) comprising water and acetonitrile is adjusted to about pH 10.

In some aspects of the methods of the present disclosure, the pH is adjusted using 25% acetic acid.

In some aspects of the methods of the present disclosure, the pH is adjusted using 25% $NH_4OH$ in $H_2O$.

In some aspects, the solution of step (c) (i) is maintained at 0° C., 10° C., 20° C., 30° C., 40° C., 50° C., 60° C., 70° C., or 80° C.

In some aspects, the solution of step (c) (i) is maintained at 50° C.

In some aspects, the solution of step (c) (i) is maintained at Room Temperature ° C.

In some aspects, the solution of step (c) (i) is maintained for 10 minutes, 20 minutes, 30 minutes, 40 minutes, 50 minutes, 55 minutes, 60 minutes, 65 minutes, 70 minutes, 75 minutes, 80 minutes, 90 minutes, 100 minutes, 110 minutes, 2 hours, 3 hours, 4 hours, 5 hours, 10 hours, 20 hours, 24 hours, 30 hours, 40 hours, 50 hours, 60 hours, or 72 hours at a temperature disclosed herein.

In some aspects, the solution of step (c) (i) is maintained for 65 minutes at a temperature disclosed herein.

In some aspects, the solution of step (c) (i) is maintained for 24 hours at a temperature disclosed herein.

In some aspects, the solution of step (c) (i) is maintained for 65 minutes at 50° C.

In some aspects, the solution of step (c) (i) is maintained for 24 hours at Room Temperature ° C.

In some aspects of the methods of the present disclosure, the RP-HPLC is performed using a C18 column.

In some aspects of the methods of the present disclosure, the RP-HPLC is performed using a solution comprising $NaHCO_3$, water and acetonitrile as the eluent.

In some aspects of the methods of the present disclosure, the solution comprising $NaHCO_3$, water and acetonitrile comprises 0.01M, 0.05M, 0.1M, 0.2M, 0.3M, 0.4M, or 0.5M $NaHCO_3$.

In some aspects of the methods of the present disclosure, the RP-HPLC is performed using a solution comprising TFA, water and acetonitrile as the eluent.

In some aspects of the methods of the present disclosure, the solution comprising TFA, water and acetonitrile comprises 0.01%, 0.05%, 0.1%, 0.2%, 0.3%, 0.4%, or 0.5% TFA.

In some aspects of the methods of the present disclosure, the RP-HPLC comprises adjusting the pH of purified peptide fractions.

In some aspects of the methods of the present disclosure, in step (d), the synthesized GLP-2 analog peptide is converted to its sodium cation form.

In some aspects of the methods of the present disclosure, step (d) comprises adjusting the pH of the purified peptide solution to about pH 7.9 using 0.01%, 0.05%, 0.1%, 0.2%, 0.5%, 1%, or 2% AcOH in water.

In some aspects of the methods of the present disclosure, step (d) comprises adjusting the pH of the purified peptide solution to about pH 7.9 using 0.1% AcOH in water.

In some aspects of the methods of the present disclosure, the product from step (c) is purified using HPLC, producing a further purified peptide solution.

In some aspects of the methods of the present disclosure, the HPLC is performed using a solution comprising AcOH, water and acetonitrile.

In some aspects of the methods of the present disclosure, the solution comprising AcOH, water and acetonitrile is a 0.01%, 0.05%, 0.1%, 0.5%, 1%, 2%, 3%, 4%, or 5% AcOH solution.

In some aspects of the methods of the present disclosure, the HPLC is performed using a solution comprising sodium acetate (NaOAc), water and acetonitrile.

In some aspects of the methods of the present disclosure, the solution comprising NaOAc, water and acetonitrile is a 0.1 mM, 0.5 mM, 1 mM, 1.5 mM, 2 mM, 2.5 mM, or 3 mM NaOAc solution.

In some aspects of the methods of the present disclosure, following HPLC purification, the pH of the further purified peptide solution is adjusted to about pH 7.9 using 0.1% AcOH in water.

In some aspects of the methods of the present disclosure, following HPLC purification, the pH of the further purified peptide solution is adjusted to about pH 5, about pH 6, about pH 6.5, about pH 7, about pH 7.5, about pH 7.9, about pH 8, about pH 8.5, or about pH 9 using 0.1% AcOH in water.

In some aspects, the starting materials presented in Table 1 can be used in the methods of the present disclosure. In some aspects, the starting materials presented in Table 1 can have a purity that is presented in the "Purity" column of Table 1:

TABLE 1

| Abbreviation | Material | Purity |
|---|---|---|
| Fmoc-Rink Amide-Linker | 4-[(2,4-Dimethoxyphenyl) (Fmoc- amino) methyl]-phenoxyacetic acid | ≥97% |
| Fmoc-Ala-OH, $H_2O$ | $N^{\alpha}$-Fmoc-alanine monohydrate | ≥98%<br>≤0.2% D-enantiomer |
| Fmoc-Arg(Pbf)-OH | $N^{\alpha}$-Fmoc-$N^{\omega}$-(2,2,4,6,7-pentamethyldihydrobenzofuran-5- sulfonyl)-arginine | ≥98%<br>≤0.2% D-enantiomer |
| Fmoc-Asn(Trt)-OH | $N^{\alpha}$-Fmoc-$N^{\gamma}$-trityl-asparagine | ≥99%<br>≤0.2% D-enantiomer |
| Fmoc-Asp(OtBu)-OH | $N^{\alpha}$-Fmoc-aspartic acid β-tertbutyl ester | ≥98%<br>≤0.2% D-enantiomer |
| Fmoc-Glu(OtBu)-OH•$H_2O$ | $N^{\alpha}$-Fmoc-glutamic acid γ-tertbutyl ester | ≥98%<br>≤0.2% D-enantiomer |
| Fmoc-Gly-OH | $N^{\alpha}$-Fmoc-glycine | ≥99% |
| Fmoc-Gly(Tmb)-OH | $N^{\alpha}$-Fmoc-$N^{\alpha}$-(2,4,6-trimethox benzyl)glycine | ≥98% |
| Fmoc-His(Trt)-OH | $N^{\alpha}$-Fmoc-$N^{\tau}$-histidine | ≥98%<br>≤0.2% D-enantiomer |
| Fmoc-Ile-OH | $N^{\alpha}$-Fmoc-isoleucine | ≥98%<br>≤0.1% Fmoc-D-Ile-OH<br>≤0.1% Fmoc-L-Allo-Ile-OH<br>≤0.1% Fmoc-D-Allo-Ile-OH |
| Fmoc-Leu-OH | $N^{\alpha}$-Fmoc-leucine | ≥98%<br>≤0.2% D-enantiomer |
| Fmoc-Lys(Boc)-OH | $N^{\alpha}$-Fmoc-$N^{\varepsilon}$-tert-butoxycarbonyl- lysine | ≥98%<br>≤0.2% D-enantiomer |
| Fmoc-Nle-OH | $N^{\alpha}$-Fmoc-norleucine | ≥98%<br>≤0.5% D-enantiomer |

TABLE 1-continued

| Abbreviation | Material | Purity |
|---|---|---|
| Fmoc-Phe-OH | $N^{\alpha}$-Fmoc-phenylalanine | ≥99%<br>≤0.2% D-enantiomer |
| Fmoc-D-Phe-OH | $N^{\alpha}$-Fmoc-D-phenylalanine | ≥98%<br>≤0.5% L-enantiomer |
| Fmoc-Ser(tBu)-OH | $N^{\alpha}$-Fmoc-O-tert-butyl-serine | ≥98%<br>≤0.2% D-enantiomer |
| Fmoc-Thr(tBu)-OH | $N^{\alpha}$-Fmoc-O-tert-butyl-threonine | ≥98%<br>≤0.1% Fmoc-D-Thr(tBu)-OH<br>≤0.1% Fmoc-L-Allo-Thr(tBu)-OH<br>≤0.1% Fmoc-D-Allo-Thr(tBu)-OH |
| Fmoc-Trp(Boc)-OH | $N^{\alpha}$-Fmoc-$N^{in}$-tert-butoxycarbonyl-tryptophan | ≥98%<br>≤0.2% D-enantiomer |
| Fmoc-Gln(Trt)-Thr($\psi^{Me,Me}$Pro)-OH | $N^{\alpha}$-Fmoc-$N^{\delta}$-trityl-glutaminyl-2,2, 5-trimethyloxazolidine-4-carboxylic acid | ≥98%<br>≤0.5% D-enantiomer |

In some aspects of the methods of the present disclosure, the apraglutide has a purity of no less than 95%.

In some aspects of the methods of the present disclosure, the apraglutide has a purity of no less than 97%.

In some aspects, the concentrations and/or presence of Des-$Gly^4$ apraglutide, $Aspartimide^3$, $Asp^{33}$-OH, Des-$Ser^7$ apraglutide, and [$Trp^{25}$, 2-(2,4,6-trimethoxyphenyl)] can be determined using RP-HPLC. Table 2a shows the purity and major impurities in two variants of the above described synthesis. Table 2b shows the purity and yield in three variants of the apraglutide synthesis process described herein.

TABLE 2a

| Test | Process A ≥95% API purity specification | Process A ≥95% API test result | Process B (FIG. 2A and 2B) ≥97% API purity specification | Process B (FIG. 2A and 2B) ≥97% API test result |
|---|---|---|---|---|
| Purity | ≥95.0% | 95.6% | ≥97.0% | 97.9% |
| Sum of related impurities | ≤5.0% | 4.4% | ≤3.0% | 2.12% |
| Des-$Gly^4$ & $Aspartimide^3$ (two co-eluting impurities) | ≤1.0% | 0.42% | ≤1.0% | 0.53% |
| $Asp^{33}$ | ≤1.0% | 0.45% | ≤1.0% | 0.59% |
| Des-$Ser^7$ | ≤1.0% | 0.13% | ≤1.0% | 0.27% |
| $Trp^{25}$ 2-(2'4'6-trimethoxyphenyl) | ≤2.0% | 0.78% | ≤1.0% | <0.05% |
| D-$Asp^3$ | ≤2.0% | 0.22% | ≤1.0% | Not detected |
| API Content | ≥80.0% | 85.7% | ≥85.0% | 91.2% |

TABLE 2b

| | Process A Run #1 | Process A Run #2 | Process A Run #3 | Process B Run #1 | Process B Run #2 | Process C Run #1 |
|---|---|---|---|---|---|---|
| Chromatographic Purity | 92.3% | 91.5% | 95.3% | 97.9% | 96.3% | 98.5% |
| Yield | 15% | 22% | 17% | 20.7% | 20.5% | 22.4% |

In some embodiments, the purified peptide pool does not contain any unspecified impurity at a concentration greater than 0.01%, 0.05%, 0.1%, 0.5%, 1%, 1.5%, or 2%. In some embodiments, the purified peptide pool does not contain any unspecified impurity at a concentration greater than 1%.

In some embodiments, the purified peptide pool does not contain an impurity comprising Des-$Gly^4$ GLP-2 analog at a concentration greater than 0.01%, 0.05%, 0.1%, 0.5%, 1%, 1.5%, or 2%, 2.5%, 3%, 3.5%, 4%, or 5%. In some embodiments, the purified peptide pool does not contain Des-$Gly^4$ GLP-2 analog at a concentration greater than 3%.

In some embodiments, the purified peptide pool does not contain an impurity comprising: Sum of $Aspartimide^3$, $Asp^{33}$-OH and Des-$Ser^7$-GLP-2 analog impurities at a concentration greater than 0.01%, 0.05%, 0.1%, 0.5%, 1%, 1.5%, or 2%, 2.5%, 3%, 3.5%, 4%, or 5%. In some embodiments, the purified peptide pool does not contain Sum of $Aspartimide^3$, $Asp^{33}$-OH and Des-$Ser^7$-GLP-2 analog impurities at a concentration greater than 2%.

In some embodiments, the purified peptide pool does not contain an impurity comprising: [$Trp^{25}$, 2-(2,4,6-trimethoxyphenyl)] GLP-2 analog at a concentration greater than 0.01%, 0.05%, 0.1%, 0.5%, 1%, 1.5%, 2%, 2.5%, 3%, 3.5%, 4%, or 5%. In some embodiments, the purified peptide pool does not contain [$Trp^{25}$, 2-(2,4,6-trimethoxyphenyl)] GLP-2 analog impurity at a concentration greater than 2%.

In some embodiments, the purity of the GLP-2 analog peptide sodium salt as measured by RP-HPLC is greater than 95%, 97% or 99%. In some embodiments, the purity of purified peptide pool as measured by RP-HPLC is greater than 95%.

In some embodiments, the purity of the GLP-2 analog peptide sodium salt does not contain any unspecified impurity at a concentration greater than 0.01%, 0.05%, 0.1%, 0.5%, 1%, 1.5%, or 2%. In some embodiments, the GLP-2 analog peptide sodium salt does not contain any unspecified impurity at a concentration greater than 1%.

In some embodiments, the GLP-2 analog peptide sodium salt does not contain an impurity comprising Des-$Gly^4$ GLP-2 analog at a concentration greater than 0.01%, 0.05%, 0.1%, 0.5%, 1%, 1.5%, 2%, 2.5%, 3%, 3.5%, 4%, or 5%. In some embodiments, the GLP-2 analog peptide sodium salt does not contain Des-$Gly^4$ GLP-2 analog impurity at a concentration greater than 3%.

In some embodiments, the GLP-2 analog peptide sodium salt does not contain an impurity comprising: sum of $Aspartimide^3$, $Asp^{33}$-OH and Des-$Ser^7$-GLP-2 analog impurities at a concentration greater than 0.01%, 0.05%, 0.1%, 0.5%, 1%, 1.5%, 2%, 2.5%, 3%, 3.5%, 4%, or 5%. In some embodiments, the GLP-2 analog peptide sodium salt does not contain the sum of $Aspartimide^3$, $Asp^{33}$-OH and Des-$Ser^7$-GLP-2 analog impurities at a concentration greater than 2%.

In some embodiments, the GLP-2 analog peptide sodium salt does not contain an impurity comprising: [$Trp^{25}$, 2-(2, 4,6-trimethoxyphenyl)] GLP-2 analog at a concentration greater than 0.01%, 0.05%, 0.1%, 0.5%, 1%, 1.5%, 2%, 2.5%, 3%, 3.5%, 4%, or 5%. In some embodiments, the GLP-2 analog peptide sodium salt does not contain [$Trp^{25}$, 2-(2,4,6-trimethoxyphenyl)] GLP-2 analog impurity at a concentration greater than 2%.

In some aspects of the methods of the present disclosure, the method can further comprise an in-process control after the conversion of the peptide to the sodium salt form, wherein the in-process control is performed by RP-HPLC and the acceptance criteria is that the peptide has a purity of ≥95.0% and no more than the following impurities: Des-$Gly^4$ apraglutide is ≤3.0%, Sum of $Aspartimide^3$, $Asp^{33}$-OH and Des-$Ser^7$ apraglutide is ≤2.0%, [$Trp^{25}$, 2-(2,4,6-trimethoxyphenyl)] apraglutide is ≤2.0% and any other unspecified impurity is ≤1.0%.

Without wishing to be bound by theory, in some embodiments, the use of Fmoc-Gln(Trt)-Thr($\psi^{Me,Me}$Pro)-OH and Fmoc-Tmb-Gly-OH during Fmoc deprotection and coupling cycles improves coupling efficiency and reduces aspartimide formation.

Without wishing to be bound by theory, in some embodiments, the use of oxyma as the coupling additive during Fmoc deprotection and coupling cycles minimizes formation of oxidation and [$Trp^{25}$, 2-(2,4,6-trimethoxyphenyl)] GLP-2 analog impurities.

Without wishing to be bound by theory, in some embodiments, the use of ACN for the mobile phase composition during sodium salt conversion by preparative RP-HPLC improves GLP-2 analog peptide composition sodium salt conversion. In some embodiments, and the removal of a titration step during sodium salt conversion by preparative RP-HPLC improves GLP-2 analog peptide composition sodium salt conversion. In some embodiments, the introduction of pH adjustment during sodium salt conversion by preparative RP-HPLC improves GLP-2 analog peptide composition sodium salt conversion.

The Des-$Gly^4$ GLP-2 analog impurity comprises $Gly^4$ missing in the peptide. The $Aspartimide^3$ GLP-2 analog impurity comprises Aspartimide formation during $Asp^3$ coupling. The $Asp^{33}$-OH GLP-2 analog impurity comprises C-terminal amide hydrolysis of the peptide. The Des-$Ser^7$ GLP-2 analog impurity comprises $Ser^7$ missing in the peptide. The [$Trp^{25}$, 2-(2,4,6-trimethoxyphenyl)] GLP-2 analog impurity comprises Fmoc-Gly(Tmb)-OH formation during the cleavage process.

In some embodiments, the GLP-2 analog peptide composition does not contain any individual impurity at a concentration greater than 0.01%, 0.05%, 0.1%, 0.5%, 1%, 1.5%, 2%, 2.5%, 3%, 3.5%, or 4%. In some embodiments, the GLP-2 analog peptide composition does not contain any individual impurity at a concentration greater than 1.5%.

In some embodiments, the GLP-2 analog peptide composition does not contain an impurity comprising Des-$Gly^4$ GLP-2 analog at a concentration greater than 0.01%, 0.05%, 0.1%, 0.5%, 1%, 1.5%, 2%, 2.5%, 3%, 3.5%, 4%, or 5%. In some embodiments, the GLP-2 analog peptide composition does not contain a Des-$Gly^4$ GLP-2 analog impurity at a concentration greater than 3%.

In some embodiments, the GLP-2 analog peptide composition does not contain an impurity comprising β-$Asp^3$ GLP-2 analog at a concentration greater than 0.01%, 0.05%, 0.1%, 0.5%, 1%, 1.5%, 2%, 2.5%, 3%, 3.5%, 4%, or 5%. In some embodiments, the GLP-2 analog peptide composition does not contain a R-$Asp^3$ GLP-2 analog impurity at a concentration greater than 1.5%. In some embodiments, the GLP-2 analog peptide composition does not contain a (3-$Asp^3$ GLP-2 analog impurity at a concentration greater than 1%.

In some embodiments, the GLP-2 analog peptide composition does not contain an impurity comprising D-His GLP-2 analog at a concentration greater than 0.01%, 0.05%, 0.1%, 0.5%, 1%, 1.5%, 2%, 2.5%, 3%, 3.5%, 4%, or 5%. In some embodiments, the GLP-2 analog peptide composition does not contain a D-His GLP-2 analog impurity at a concentration greater than 1.5%. In some embodiments, the GLP-2 analog peptide composition does not contain a D-His GLP-2 analog impurity at a concentration greater than 1%.

In some embodiments, the GLP-2 analog peptide composition does not contain an impurity comprising the sum of Aspartimide[3], $Asp^{33}$-OH and Des-$Ser^7$-GLP-2 analog impurities at a concentration greater than 0.01%, 0.05%, 0.1%, 0.5%, 1%, 1.5%, 2%, 2.5%, 3%, 3.5%, 4%, or 5%. In some embodiments, the GLP-2 analog peptide composition does not contain the sum of Aspartimide[3], $Asp^{33}$-OH and Des-$Ser^7$-GLP-2 analog impurities at a concentration greater than 2%.

In some embodiments, the GLP-2 analog peptide composition does not contain an impurity comprising: [$Trp^{25}$, 2-(2,4,6-trimethoxyphenyl)] GLP-2 analog at a concentration greater than 0.01%, 0.05%, 0.1%, 0.5%, 1%, 1.5%, 2%, 2.5%, 3%, 3.5%, 4%, or 5%. In some embodiments, the GLP-2 analog peptide composition does not contain [$Trp^{25}$, 2-(2,4,6-trimethoxyphenyl)] GLP-2 analog impurity at a concentration greater than 2%.

In some embodiments, the GLP-2 analog peptide does not contain an impurity comprising: Des-$Gly^4$ GLP-2 analog, Aspartimide[3] GLP-2 analog, $Asp^{33}$-OH GLP-2 analog, Des-$Ser^7$ GLP-2 analog, or [$Trp^{21}$, 2-(2,4,6-trimethoxyphenyl)] GLP-2 analog at a concentration greater than 0.01%, 0.05%, 0.1%, 0.5%, 1%, 1.5%, or 2%, 2.5%, 3%, 3.5%, 4%, or 5%.

In some embodiments, the GLP-2 analog peptide does not contain an impurity comprising: Des-$Gly^4$ GLP-2 analog peptide, Aspartimide[3] GLP-2 analog peptide, $Asp^{33}$-OH GLP-2 analog peptide, Des-$Ser^7$ GLP-2 analog peptide, or [$Trp^{25}$, 2-(2,4,6-trimethoxyphenyl)] GLP-2 analog peptide at a concentration greater than 0.5%.

In some embodiments, the GLP-2 analog peptide composition does not contain a total amount of impurities at a concentration greater than 1%, 3%, 5%, or 7%. In some embodiments, the GLP-2 analog peptide composition does not contain a total amount of impurities at a concentration greater than 5%.

In some embodiments, the GLP-2 analog peptide composition does not contain an impurity comprising acetate at a concentration greater than 1%, 2%, 3%, 4%, or 5%. In some embodiments, the GLP-2 analog peptide composition does not contain acetate at a concentration greater than 5%.

In some embodiments, the GLP-2 analog peptide composition does not contain an impurity comprising trifluoroacetic acid at a concentration greater than 0.01%, 0.03%, 0.05%, 0.07%, 0.1%, 0.2%, 0.5%, or 1%. In some embodiments, the GLP-2 analog peptide composition does not contain trifluoroacetic acid at a concentration greater than 0.1%.

In some embodiments, the GLP-2 analog peptide composition contains an impurity comprising acetonitrile at less than 5,000, 4,000, 3,000, 2,000, 1,000, 500, 400, 300, 200, or 100 ppm. In some embodiments, the GLP-2 analog peptide composition contains acetonitrile at less than 450 ppm.

In some embodiments, the GLP-2 analog peptide composition does not contain an impurity comprising bacterial endotoxins at a concentration greater than 0.1, 0.5, 1, 2, 3, 4, 5, 6, 7, 8, 9, or 10 EU/mg. In some embodiments, the GLP-2 analog peptide composition does not contain bacterial endotoxins at a concentration greater than 5.0 EU/mg.

In some embodiments, the GLP-2 analog peptide composition does not contain an impurity comprising aerobic microbes at a concentration greater than 1, 10, 50, 100, 150, or 200 CFU/0.1 g. In some embodiments, the GLP-2 analog peptide composition does not contain aerobic microbes at a concentration greater than 100 CFU/0.1 g.

In some embodiments, the GLP-2 analog peptide composition does not contain an impurity comprising yeasts and mold at a combined concentration greater than 0.1, 1, 5, 10, 15, or 20 CFU/0.1 g. In some embodiments, the GLP-2 analog peptide composition does not contain yeasts and mold at a combined concentration greater than 10 CFU/0.1 g.

In some embodiments, the GLP-2 analog peptide composition does not contain impurities comprising acetate, trifluoroacetic acid, acetonitrile, bacterial endotoxins, aerobic microbes, yeasts, mold, or any combination thereof.

After synthesis, the apraglutide active pharmaceutical ingredient ("API") is lyophilized and thereafter formulated into a drug product.

Formulation

GLP-2 agonists of the present disclosure can use used alone as a pharmaceutical or in a pharmaceutical composition comprising one or more GLP-2 agonists as the active ingredient(s) and a pharmaceutically acceptable adjuvant, excipient, diluent, or carrier. Pharmaceutical compositions may also comprise other active ingredients.

Suitable pharmaceutically acceptable carriers include those typically used with peptide-based drugs. See, e.g., "Remington: The Science and Practice of Pharmacy," 22nd ed., Pharmaceutical Press, Philadelphia, PA, 2012, for general guidance on drug formulations. Non-limiting examples of suitable excipients include glycine, L-histidine, mannitol, and any combination thereof.

A preferred formulation uses Glycine as a buffering agent. L-Histidine is used in this formulation as a physically stabilizing agent. L-Histidine also serves as a buffer, maintaining the target pH. Mannitol is used in this formulation as a bulking agent in the lyophilization process step. Water for injection is the solvent of this formulation; the water for injection is removed during the lyophilization step. Sodium hydroxide is used for pH adjustment. pH is measured and may be adjusted to 8.30±0.10 with sodium hydroxide (NaOH) solution.

The present disclosure provides a robust and reproducible lyophilization cycle for the manufacture of the drug product. Using the same container closure intended to be used in the manufacture of the clinical batch, two scaled down development batches were filled. The lyophilization cycle was optimized for primary drying (primary drying cycle) to define the process to be implemented in clinical manufacturing of the drug product. The optimized lyophilization cycle resulted in a drug product with the expected quality attributes (i.e., assay, purity and impurity levels, reconstitution time and moisture content) and was deemed appropriate for a clinical batch of the drug product. A stability study conducted on the second scaled-down development batch demonstrated the drug product remained unchanged at the intended storage temperature (2 to 8° C.) for up to 3 months.

In some aspects, the composition of apraglutide for injection and reconstituted solution presented in Table 3 is an exemplary composition that may be produced using the methods of the present disclosure.

TABLE 3

| | | | Quantity | |
|---|---|---|---|---|
| Name of Ingredient | Reference | Function | Apraglutide for Injection (mg/mL) | Reconstituted Solution (mg/mL) |
| Apraglutide | In-house | Drug substance | 12.5[a] | 25 |
| Glycine | Ph. Eur/ USP | Buffering Agent | 1.88 | 3.75 |

TABLE 3-continued

| Name of Ingredient | Reference | Function | Quantity Apraglutide for Injection (mg/mL) | Reconstituted Solution (mg/mL) |
|---|---|---|---|---|
| L-Histidine | Ph. Eur/ USP | Stabilizing Agent | 3.88 | 7.75 |
| Mannitol | Ph. Eur/ USP | Bulking Agent | 57.5 | 115.0 |
| Sodium Hydroxide | Ph. Eur/ USP | pH adjustment | q.s. to pH 8.3 | — |
| Water for Injection (WFT)[b] | Ph. Eur/ USP | Solvent | 1.25 ml | — |
| Nitrogen[b] | NF | Inert Overlay | — | — |
| Sterile Water for Injection | Ph. Eur/ USP | Reconstitution diluent | — | 0.5 mL |

[a]The quantity of drug substance to be used is calculate based on the apraglutide content in the corresponding drug substance batch.
[b]Components used during the manufacture of the drug product that do not appear in the final product.

In some embodiments, the apraglutide composition may include excipients comprising glycine, L-histidine, mannitol, water for injection (WFI), sterile water for injection (sWFI), sodium hydroxide, sucrose, or any combination thereof.

In one aspect the present disclosure provides a pharmaceutical composition comprising apraglutide of the present disclosure, glycine, L-histidine and mannitol dissolved in water, wherein the concentration of the apraglutide is 25 mg/mL, the concentration of glycine is 3.75 mg/mL, the concentration of L-histidine is 7.75 mg/mL of water and the concentration of mannitol is 115.0 mg/mL. In some aspects, the volume of water can be 0.5 mL. In some aspects, the preceding pharmaceutical composition can further comprise sodium hydroxide in an amount such that the pH of the solution is about pH 8.3.

In some aspects, the osmolarity of a pharmaceutical composition of the present disclosure is between 290-780 mOsmol/kg. In some aspects, the osmolarity of a pharmaceutical composition of the present disclosure is about 780 mOsmol/kg. In some aspects, the osmolarity of a pharmaceutical composition of the present disclosure is about 780±160 mOsmol/kg.

The GLP-2 analog peptide composition for injection may be an aseptically manufactured lyophilized powder for solution for injection. It can be presented in a colorless glass vial suitable for a lyophilized sterile product, closed with a rubber stopper and sealed with an aluminum cap. Prior to administration, the GLP-2 analog peptide for injection may be dissolved in 0.5 mL of sterile Water for Injection (sWFI). The reconstituted solution may be administered subcutaneously.

Administration

In some embodiments, GLP-2 agonists, e.g., apraglutide, are administered parenterally, e.g. by injection. Formulations suitable for parenteral administration include aqueous and non-aqueous, isotonic sterile injection solutions, which can contain antioxidants, buffers, bacteriostatics, and solutes that render the formulation isotonic with the blood of the intended recipient, and aqueous and non-aqueous sterile suspensions that can include suspending agents, solubilizers, thickening agents, stabilizers, and preservatives. Liquid carriers, for injectable solutions, include by way of example and without limitation water, saline, aqueous dextrose and glycols.

In some aspects, the apraglutide is delivered via a two chamber syringe or dual cartridge injector. One example of such a syringe is described in PCT/EP2012/000787, the contents of which are incorporated herein by reference.

Dosing

Amounts that constitute an effective dose may depend on various factors such as the disease and clinical status of the patient (e.g. weight) and the route of administration. Doses may be administered, e.g., twice daily, once daily, twice a week, weekly, biweekly, once or twice monthly, etc. Doses generally range from about 1 mg to about 10 mg per week for a period of about 1 week to about 100 weeks. In some embodiments, the weekly dose is between about 1 mg and 10 mg. In some embodiments, subjects are dosed from between about 1 weeks to about 100 weeks, about 1 weeks to about 80 weeks, about 1 weeks to about 60 weeks, about 1 weeks to about 48 weeks, about 2 weeks to about 24 weeks, about 2 weeks to about 20 weeks, or about 2 weeks to about 16 weeks. In some embodiments, subjects are administered a dose about once a week. In some embodiments, subjects are administered a dose about once every two weeks or about twice a month. About once every two weeks or about twice a month.

Apraglutide increases citrulline levels in a dose dependent manner. Citrulline is a marker of small bowel enterocyte mass. Dosing of apraglutide at 1 mg, 5 mg and 10 mg induces long-lasting increases in citrulline concentration in patients.

In some embodiments, apraglutide is administered parenterally (e.g., subcutaneously, intravenously, intramuscularly, or orally). In some embodiments, apraglutide is administered intravenously. In some embodiments, apraglutide is administered subcutaneously.

Due to the non-linear increase of exposures (AUC and $C_{max}$) as body weight decreases, it is desired to dose patients with body weight below 50 kg with 2.5 mg to prevent high exposures. Patients of 50 kg or higher may receive 5 mg or higher doses.

Indications

In some embodiments, a subject who has been administered an effective dose of a GLP-2 agonist needs less nutritional support relative to a control. For example, in some embodiments, a subject who has been administered an effective dose of GLP-2 agonist needs at least 10%, at least 20%, at least 30%, at least 40%, at least 50%, at least 60%, at least 70%, at least 80%, or at least 90% less nutritional support relative to a control. In one embodiment, a subject who has been administered an effective dose of GLP-2 agonist needs 100% less nutritional support relative to a control (i.e., enteral autonomy).

In some embodiments, a subject who has been administered an effective dose of a GLP-2 agonist needs total parenteral support for fewer days relative to a control. For example, in some embodiments, administration of an effective dose of a GLP-2 agonist may reduce the length of time during which total parenteral support is needed by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% relative to a control. In one embodiment, administration of an effective dose of GLP-2 agonist reduces the length of time during which total parenteral support is needed by 100% relative to a control (i.e., enteral autonomy). In some embodiments, a subject who has been administered an effective dose of a GLP-2 agonist needs total parenteral support for less than 85 days per year, less than 80 days per year, less than 75 days per year, less than 70 days per year, less than 65 days per year, less than 60 days per year, less than 55 days per year, less than 50 days per year, less than 45 days per year, less than 40 days per year, less than 35 days per year, less than 30 days per year, less than 25 days per year, less than 20 days per year, less than 15 days per year, less than 10 days per year, or less than 5 days per year.

In some embodiments, a subject who is administered an effective dose of a GLP-2 agonist does not need total parenteral nutrition following treatment.

In some embodiments the patients receiving apraglutide include male and female subjects with short bowel syndrome associated intestinal failure ("SBS-IF"), receiving parenteral support, secondary to surgical resection of the small intestine with either:

a. Colon-in-continuity ("CIC") remaining and no stoma (small intestine <200 cm from duodeno-jejunal flexure, based on available medical/surgical records) with the latest intestinal resection being at least 12 months prior to screening OR
b. Jejunostomy or ileostomy (<200 cm from duodeno-jejunal flexure, based on available medical/surgical records) with the latest intestinal resection being at least 6 months prior to screening.

In some embodiments, administration of an effective dose of a GLP-2 agonist results in reduced hospital length of stay relative to a control. For example, in some embodiments, administration of an effective dose of a GLP-2 agonist may reduce the length of a hospital stay by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% relative to a control. In some embodiments, a subject who has been administered an effective dose of a GLP-2 agonist is hospitalized for less than 50 days, less than 45 days, less than 40 days, less than 35 days, less than 30 days, less than 25 days, less than 20 days, less than 15 days, less than 10 days, or less than 5 days.

In some embodiments, administration of an effective dose of a GLP-2 agonist to a population of subjects reduces the mortality rate relative to a population of subjects who receive a standard of care treatment (e.g., surgical treatment, nutritional support, and wound care) that does not comprise administration of an effective dose of a GLP-2 agonist. For example, in some embodiments, the mortality rate is reduced to less than 15%, less than 12%, less than 10%, less than 8%, less than 5%, less than 3%, less than 2%, or less than 1%. The SC injection will typically be administered in the abdominal area or in the thigh. The injection site should be rotated such that an injection is administered at least 5 cm away from where the last injection was administered.

It is believed that apraglutide can demonstrate clinical efficacy (reduction in PS volume) in SBS-IF subjects with either CIC or stoma after 24 weeks of once a week dosing. Accordingly, in one embodiment a single 2.5 mg dose (for subjects with body weight less than 50 kg at most recent trial visit) or 5 mg dose (for subjects with body weight 50 kg or more at most recent trial visit) of apraglutide or matching placebo will be administered by subcutaneous ("SC") injection once weekly during a treatment period of 24 weeks (stoma) or 48 weeks (CIC).

Apraglutide has demonstrated superior effects on energy absorption with less frequent dosing (i.e., once weekly) compared to other GLP-2 analogs. When dosed at 5 mg once weekly, apraglutide caused a 140.1% (±15.8) change from baseline increase in urinary input, a change in baseline in wet weight absorption of 760.4 g/day (±236.1), and a change in baseline in energy absorption of 1,074 kj/day (±377).

Apraglutide promoted the increase of absolute urine volume output by an adjusted mean of 711 mL/day (95% CI 132 to 1,289; P=0.021) compared to placebo, corresponding to a daily increase of 48% (95% CI 12 to 84; P=0.014), as shown in Table 9. Apraglutide promoted the increase of absolute urine volume output by an adjusted mean of 714 mL/day (95% CI 490 to 939; P=0.002), corresponding to a daily increase of 49% (95% CI 4 to 94; P=0.041), as shown in Table 10. Treatment with 10 mg apraglutide promoted the increase of absolute urine volume output by an adjusted mean of 795 mL (95% CI 195 to 1,394; P=0.014) compared to placebo. The corresponding change in relative urine production was 34% (95% CI−4 to 71; P=0.072).

Apraglutide increased urine sodium excretion compared to placebo by an adjusted mean of 56 mmol/day (95% CI−10 to 123; P=0.087), as shown in Table 9. 5 mg apraglutide increased urine sodium excretion compared to placebo by an adjusted mean of 66 mmol/day (95% CI−69 to 201; P=0.171), as shown in Table 10. In the 10 mg dose group, absolute urine sodium excretion was increased by an adjusted mean of 88 mmol/day (95% CI 20 to 156; P=0.017) compared to placebo, as shown in Table 9.

Apraglutide increased intestinal absorption of energy by 1,095 kJ/day (95% CI 196 to 1,994; P=0.024), as shown in Table 19.

By contrast, teduglutide, dosed once daily, caused a 139.3% change from baseline increase in urinary input, a change in baseline in wet weight absorption of 743 g/day (±119.25), and a change in baseline in energy absorption of 792 kj/day (±570), as reported in Jeppesen, Gut, 54, pp. 1224-1231 (2005).

Similarly, by contrast, glepaglutide, dosed once daily, caused a 111% (0.1 mg dose), 140% (1.0 mg dose) or 132% (10 mg dose) change from baseline increase in urinary output, a change in baseline in wet weight absorption of −211 g/day (0.1 mg dose), 650 g/day (1.0 mg dose) or 786 g/day (10 mg dose), and a change in baseline in energy absorption of −377 kj/day (0.1 mg dose), 435 kj/day (1.0 mg dose) or 588 kj/day (10 m g dose), as reported in Maimi, Lancet Gastroenterol Hepatol, 4, pp. 354-363 (2019).

Any use of growth hormone, glutamine or growth factors such as native GLP-2, GLP-1 or GLP-2, GLP-1 analogues other than the IMP under investigation should be discontinued for 12 month (CIC subjects) and 6 months (stoma subjects) before administration of the apraglutide.

In some embodiments, administration of an effective dose of a GLP-2 agonist to a population of subjects reduces the morbidity rate relative to a population of subjects who receive a standard of care treatment (e.g., surgical treatment, nutritional support, and wound care) that does not comprise administration of an effective dose of a GLP-2 agonist. For example, in some embodiments, the morbidity rate is reduced to less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10%.

In some embodiments, apraglutide is used for post-surgical enteral autonomy recovery or for treatment of enterocutaneous fistulas. In some embodiments, apraglutide is used for treatment of anastomotic leaks, functional intestinal failure, intestinal insufficiency, necrotizing enterocolitis, graft versus host disease, Crohn's disease or celiac disease.

The present disclosure provides a method of treating short bowel syndrome in a subject, the method comprising administering at least one therapeutically effective amount of a GLP-2 analog peptide composition of the present disclosure.

The present disclosure provides a GLP-2 analog peptide composition of the present disclosure for use in the treatment of short bowel syndrome in a subject, wherein the GLP-2 analog peptide composition of the present disclosure is for administration to the subject in at least one therapeutically effective amount.

The present disclosure provides a GLP-2 analog peptide composition of the present disclosure for the manufacture of a medicament for treating of short bowel syndrome in a subject, wherein the GLP-2 analog peptide composition of the present disclosure is for administration to the subject in at least one therapeutically effective amount.

The present disclosure provides a method for increasing the intestinal absorption of wet weight in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing the intestinal absorption of wet weight in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing the intestinal absorption of wet weight in a subject with short bowel syndrome, wherein the GLP-2 analog peptide composition of the present disclosure is for administration to the subject in at least one therapeutically effective amount.

In some aspects, the increase in intestinal absorption of wet weight can be at least about 100 g/day, or at least about 200 g/day, or at least about 300 g/day, or at least about 400 g/day, or at least about 500 g/day, or at least about 600 g/day, or at least about 700 g/day, or at least about 800 g/day, or at least about 900 g/day, or at least about 1000 g/day.

The present disclosure provides a method for decreasing fecal output in a subject with short bowel syndrome, the method comprising administering to the subject at least one therapeutically effective amount of a GLP-2 analog peptide composition of the present disclosure. The present disclosure provides a method for decreasing stoma output in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of decreasing the fecal output in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for decreasing the fecal output in a subject with short bowel syndrome, wherein the GLP-2 analog peptide composition of the present disclosure is for administration to the subject in at least one therapeutically effective amount.

In some aspects, the decrease in fecal output can be at least about 100 g/day, or at least about 200 g/day, or at least about 300 g/day, or at least about 400 g/day, or at least about 500 g/day, or at least about 600 g/day, or at least about 700 g/day, or at least about 800 g/day, or at least about 900 g/day, or a least about 1000 g/day.

The present disclosure provides a method for increasing urine production in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing the urine production in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing the urine production in a subject with short bowel syndrome, wherein the GLP-2 analog peptide composition of the present disclosure is for administration to the subject in at least one therapeutically effective amount.

In some aspects, the increase in urine production can be at least about 100 g/day, or at least about 200 g/day, or at least about 300 g/day, or at least about 400 g/day, or at least about 500 g/day, or at least about 600 g/day, or at least about 700 g/day, or at least about 800 g/day, or at least about 900 g/day, or a least about 1000 g/day.

The present disclosure provides a method for increasing absorption of sodium and/or potassium in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing the absorption of sodium and/or potassium in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing the absorption of sodium and/or potassium in a subject with short bowel syndrome, wherein the GLP-2 analog peptide composition of the present disclosure is for administration to the subject in at least one therapeutically effective amount.

In some aspects, the increase in absorption of sodium and/or potassium can be at least about 5 mmol/day, or at least about 10 mmol/day, or at least about 15 mmol/day, or at least about 20 mmol/day, or at least about 25 mmol/day, or at least about 30 mmol/day, or at least about 35 mmol/day, or at least about 40 mmol/day, or at least about 45 mmol/day, or at least about 50 mmol/day.

The present disclosure provides a method for increasing urine sodium and/or potassium excretion in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing the urine sodium and/or potassium excretion in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing the urine sodium and/or potassium excretion in a subject with short bowel syndrome, wherein the GLP-2 analog peptide composition of the present disclosure is for administration to the subject in at least one therapeutically effective amount.

In some aspects, the increase urine sodium and/or potassium excretion can be at least about 5 mmol/day, or at least about 10 mmol/day, or at least about 15 mmol/day, or at least about 20 mmol/day, or at least about 25 mmol/day, or at least about 30 mmol/day, or at least about 35 mmol/day, or at least about 40 mmol/day, or at least about 45 mmol/day, or at least about 50 mmol/day.

The present disclosure provides a method for increasing intestinal absorption of energy in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing the intestinal absorption of energy in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing the intestinal absorption of energy in a subject with short bowel syndrome, wherein the GLP-2 analog peptide composition of the present disclosure is for administration to the subject in at least one therapeutically effective amount.

In some aspects, the increase intestinal absorption of energy can be at least about 500 kJ/day, or at least about 600 kJ/day, or at least about 700 kJ/day, or at least about 800 kJ/day, or at least about 900 kJ/day, or at least about 1000 kJ/day, or at least about 1100 kJ/day or at least about 1200 kJ/day.

The present disclosure provides a method for decreasing the energy content of fecal output in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of decreasing the energy content of fecal output in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for decreasing the energy content of fecal output in a subject with short bowel syndrome, wherein the GLP-2 analog peptide composition of the present disclosure is for administration to the subject in at least one therapeutically effective amount.

In some aspects, the decrease in the energy content of the fecal output can be at least about 500 kJ/day, or at least about 600 kJ/day, or at least about 700 kJ/day, or at least about 800 kJ/day, or at least about 900 kJ/day, or at least about 1000 kJ/day, or at least about 1100 kJ/day or at least about 1200 kJ/day.

The present disclosure provides a method for increasing carbohydrate and/or lipid absorption in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing carbohydrate and/or lipid absorption in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing carbohydrate and/or lipid absorption in a subject with short bowel syndrome, wherein the GLP-2 analog peptide composition of the present disclosure is for administration to the subject in at least one therapeutically effective amount.

In some aspects, the increase in carbohydrate and/or lipid absorption can be at least about 100 kJ/day, or at least about 200 kJ/day, or at least about 300 kJ/day, or at least about 400 kJ/day, or at least about 500 kJ/day, or at least about 600 kJ/day, or at least about 700 kJ/day, or at least about 800 kJ/day, or at least about 900 kJ/day, or at least about 1000 kJ/day, or at least about 1100 kJ/day or at least about 1200 kJ/day.

The present disclosure provides a method for increasing protein absorption in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing protein absorption in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing protein absorption in a subject with short bowel syndrome, wherein the GLP-2 analog peptide composition of the present disclosure is for administration to the subject in at least one therapeutically effective amount.

In some aspects, the increase in protein absorption can be at least about 100 kJ/day, or at least about 200 kJ/day, or at least about 300 kJ/day, or at least about 400 kJ/day, or at least about 500 kJ/day, or at least about 600 kJ/day, or at least about 700 kJ/day, or at least about 800 kJ/day, or at least about 900 kJ/day, or at least about 1000 kJ/day, or at least about 1100 kJ/day or at least about 1200 kJ/day.

The present disclosure provides a method for increasing body weight in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing body weight in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing body weight in a subject with short bowel syndrome, wherein the GLP-2 analog peptide composition of the present disclosure is for administration to the subject in at least one therapeutically effective amount.

In some aspects, the increase in body weight can be at least about 0.5 kg, or at least about 1.0 kg, or at least about 1.5 kg, or at least about 2.0 kg, or at least about 2.5 kg, or at least about 3.0 kg, or at least about 3.5 kg, or at least about 4.0 kg, or at least about 4.5 kg, or at least about 5.0 kg.

The present disclosure provides a method for increasing lean body mass in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing lean body mass in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing lean body mass in a subject with short bowel syndrome, wherein the GLP-2 analog peptide composition of the present disclosure is for administration to the subject in at least one therapeutically effective amount.

In some aspects, the increase in lean body mass can be at least about 0.5 kg, or at least about 1.0 kg, or at least about 1.5 kg, or at least about 2.0 kg, or at least about 2.5 kg, or at least about 3.0 kg, or at least about 3.5 kg, or at least about 4.0 kg, or at least about 4.5 kg, or at least about 5.0 kg.

The present disclosure provides a method for decreasing fat mass in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of decreasing fat mass in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for decreasing fat mass in a subject with short bowel syndrome, wherein the GLP-2 analog peptide composition of the present disclosure is for administration to the subject in at least one therapeutically effective amount.

In some aspects, the decrease in fat mass can be at least about 0.5 kg, or at least about 1.0 kg, or at least about 1.5 kg, or at least about 2.0 kg, or at least about 2.5 kg, or at least about 3.0 kg, or at least about 3.5 kg, or at least about 4.0 kg, or at least about 4.5 kg, or at least about 5.0 kg.

The present disclosure provides a method for increasing the concentration of L-citrulline in plasma in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing the concentration of L-citrulline in plasma in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing the concentration of L-citrulline in plasma in a subject with short bowel syndrome, wherein the GLP-2 analog peptide composition of the present disclosure is for administration to the subject in at least one therapeutically effective amount.

In some aspects, the increase in concentration in L-citrulline in plasma can be at least about 5 μmol/L, or at least about 10 μmol/L, or at least about 15 μmol/L, or at least about 20 μmol/L.

The present disclosure provides a method for increasing urine volume output in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of increasing urine volume output in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for increasing urine volume output in a subject with short bowel syndrome, wherein the GLP-2 analog peptide composition of the present disclosure is for administration to the subject in at least one therapeutically effective amount.

In some aspects, the increase in urine volume output can be at least about 400 mL/day, or at least about 500 mL/day, or at least about 600 mL/day, or at least about 700 mL/day, or at least about 800 mL/day, or at least about 900 mL/day, or at least about 1000 mL/day.

The present disclosure provides a method for decreasing oral fluid intake in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of decreasing oral fluid intake in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for decreasing oral fluid intake in a subject with short bowel syndrome, wherein the GLP-2 analog peptide composition of the present disclosure is for administration to the subject in at least one therapeutically effective amount.

In some aspects, the decrease in oral fluid intake can be at least about 400 mL/day, or at least about 500 mL/day, or at least about 600 mL/day, or at least about 700 mL/day, or at least about 800 mL/day, or at least about 900 mL/day, or at least about 1000 mL/day.

The present disclosure provides a method for decreasing parenteral support volume in a subject with short bowel syndrome, the method comprising administering to the subject at least one therapeutically effective amount of a GLP-2 analog peptide composition of the present disclosure. The present disclosure provides a GLP-2 analog peptide composition of the present disclosure for use in a method of decreasing parenteral support volume in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for decreasing parenteral support volume in a subject with short bowel syndrome, wherein the GLP-2 analog peptide composition of the present disclosure is for administration to the subject in at least one therapeutically effective amount.

In some aspects, the decrease in parenteral support volume can be at least about 400 mL/day, or at least about 500 mL/day, or at least about 600 mL/day, or at least about 700 mL/day, or at least about 800 mL/day, or at least about 900 mL/day, or at least about 1000 mL/day.

The present disclosure provides a method for decreasing plasma aldosterone concentration in a subject with short bowel syndrome, the method comprising administering to the subject at least one therapeutically effective amount of a GLP-2 analog peptide composition of the present disclosure.

The present disclosure provides a GLP-2 analog peptide composition of the present disclosure for use in a method of decreasing plasma aldosterone concentration in a subject with short bowel syndrome, wherein the GLP-2 analog peptide composition of the present disclosure is for administration to the subject in at least one therapeutically effective amount. The present disclosure provides a GLP-2 analog peptide composition of the present disclosure for use in the manufacture of a medicament for decreasing plasma aldosterone concentration in a subject with short bowel syndrome, wherein the GLP-2 analog peptide composition of the present disclosure is for administration to the subject in at least one therapeutically effective amount.

In some aspects, the decrease in plasma aldosterone concentration can be at least about 500 μmol/L, or at least about 750 μmol/L, or at least about 1000 μmol/L, or at least about 1250 μmol/L, or at least about 1500 μmol/L, or at least about 1750 μmol/L, or at least about 2000 μmol/L, or at least about 2250 μmol/L, or at least about 2500 μmol/L, or at least about 2750 μmol/L, or at least about 3000 μmol/L.

In some aspects of the preceding methods, an increase can be an increase of at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 99% as compared to a control level. In some aspects, the control level is the amount prior to administration of the GLP-2 analog peptide composition of the present disclosure.

In some aspects of the preceding methods, a decrease can be a decrease of at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 99% as compared to a control level. In some aspects, the control level is the amount prior to administration of the GLP-2 analog peptide composition of the present disclosure.

In some aspects, the increase or decreases recited by the preceding methods are after at least about four weeks of treatment with the GLP-2 analog peptide composition of the present disclosure.

In some aspects, the short bowel syndrome can be short bowel syndrome intestinal insufficiency (SBS-II). In some aspects, the short bowel syndrome can be short bowel syndrome intestinal failure.

All publications, patent applications, patents, and other references mentioned herein are incorporated by reference in their entirety.

Exemplary Embodiments

Embodiment 1. A composition comprising a sodium salt of apraglutide, wherein the sodium salt of apraglutide has a purity of no less than 95%, wherein apraglutide has the following structure:

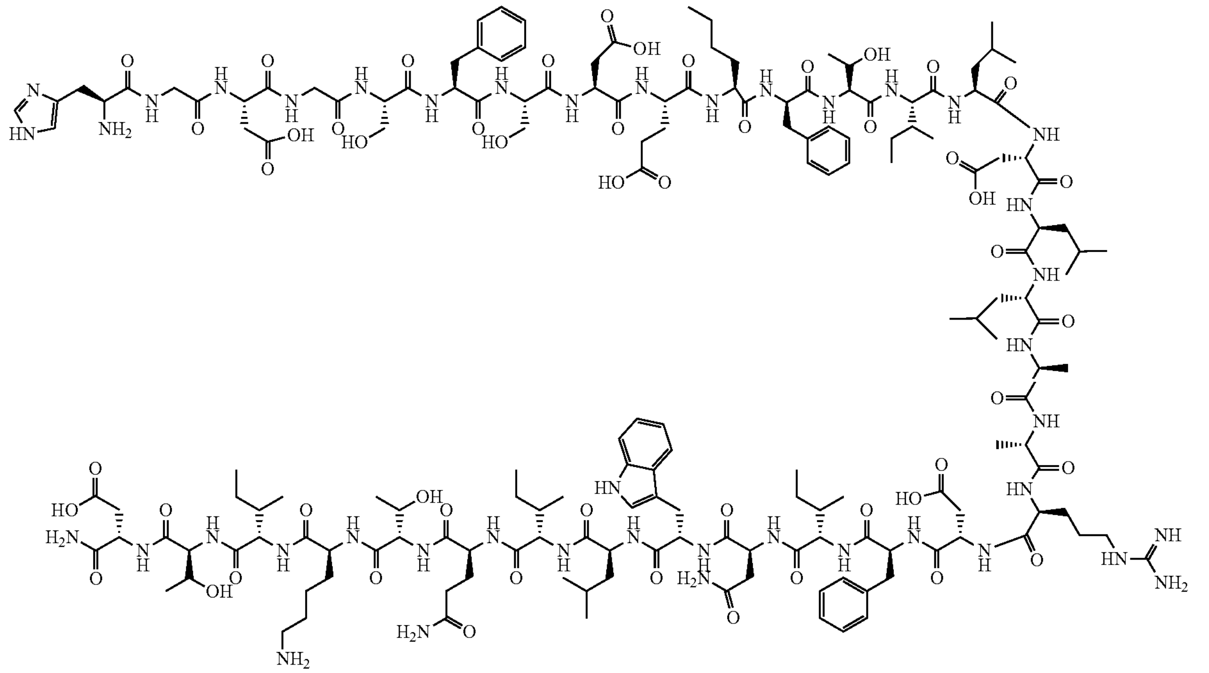

Embodiment 2. The composition of embodiment 1, wherein the sodium salt of apraglutide has a purity of no less than 97%.

Embodiment 3. The composition of any one of the preceding embodiments, wherein the composition comprises no more than 3% of a Des-$Gly^4$ apraglutide impurity.

Embodiment 4. The composition of any one of the preceding embodiments, wherein the sum of $Aspartimide^3$ apraglutide, $Asp^{33}$-OH apraglutide and Des-$Ser^7$ apraglutide impurities in the composition is no more than 2%.

Embodiment 5. The composition of any one of the preceding embodiments, wherein the composition comprises no more than 2% of a [$Trp^{25}$, 2-(2,4,6-trimethoxyphenyl)] apraglutide impurity.

Embodiment 6. The composition of any one of the preceding embodiments, wherein the composition comprises no more than 1.5% of a β-$Asp^3$ apraglutide impurity.

Embodiment 7. The composition of any one of the preceding embodiments, wherein the composition comprises no more than 1% of a β-$Asp^3$ apraglutide impurity.

Embodiment 8. The composition of any one of the preceding embodiments, wherein the composition comprises no more than 1% of a D-His apraglutide impurity.

Embodiment 9. The composition of any one of the preceding embodiments, wherein the composition comprises:

no more than 1% of a $Asp^{33}$-OH apraglutide impurity, no more than 1% of a Des-$Ser^7$ apraglutide impurity, no more than 1% of a D-$Aspartimide^3$ apraglutide impurity, no more than 1% of a [$Trp^{21}$, 2-(2,4,6-trimethoxyphenyl)] apraglutide impurity, and wherein the sum of Des-$Gly^4$ apraglutide and $Aspartimide^3$ apraglutide impurities in the composition is no more than 1%.

Embodiment 10. The composition of any of the preceding embodiments, wherein the sodium salt of apraglutide is provided as a lyophilized powder.

Embodiment 11. A pharmaceutical composition comprising the composition of any one of the preceding embodiments.

Embodiment 12. The pharmaceutical composition of embodiment 11, further comprising at least one of glycine, L-histidine and mannitol.

Embodiment 13. A pharmaceutical composition of embodiment 10, wherein the pharmaceutical composition comprises:

about 12.5 mg of apraglutide (sodium salt);

about 1.88 mg of glycine;

about 3.88 mg of L-histidine;

about 57.5 mg of mannitol.

Embodiment 14. The pharmaceutical composition of embodiment 12, wherein the pharmaceutical composition is provided as a lyophilized powder.

Embodiment 15. A two-chamber powder syringe comprising the composition of any one of embodiments 1-10 or the pharmaceutical composition of any one of embodiments 11-14.

Embodiment 16. A method of making a GLP-2 analog peptide comprising:

a) performing solid phase peptide synthesis (SPPS) to synthesize the GLP-2 analog peptide on an Fmoc-Rink-amid-MethylBenzHydril Amine(MBHA)-resin;

b) cleaving the synthesized GLP-2 analog peptide off the resin and deprotecting the side chains of the synthesized GLP-2 analog peptide by treating the resin with a solution comprising trifluoroacetic acid (TFA), water, and anisole;

c) purifying the synthesized GLP-2 analog peptide from step (b) by performing a first preparative reversed-phase high performance liquid chromatography (RP-HPLC) purification using TFA-based mobile phases, thereby producing a solution comprising the GLP-2 analog peptide with a purity of no less than 90%;

d) purifying the product of step (c) by performing a second RP-HPLC purification, using $NaHCO_3$-based mobile phases, thereby producing solution comprising the GLP-2 analog peptide with a purity of no less than 97%.

Embodiment 17. The method of embodiment 16, further comprising:

e) further purifying the product from step (d) by performing a third RP-HPLC purification using NaOAc-based mobile phases, thereby producing a solution comprising the sodium salt of the GLP-2 analog peptide with a purity of no less than 97%.

Embodiment 18. The method of embodiment 17, further comprising:

f) adjusting the pH solution comprising the sodium salt of the GLP-2 analog peptide to about pH 7.9 using 0.1% AcOH in water;

g) passing the product of step (f) through a filter with a pore size of 0.2 μm;

h) lyophilizing the product of step (g), thereby producing lyophilized sodium salt of the GLP-2 analog peptide with a purity of no less than 97%.

Embodiment 19. The method of embodiment 16, further comprising:

c)(i) performing a decarboxylation of the synthesized GLP-2 analog peptide by solubilizing the peptide in a solution comprising water and acetonitrile in ammonia buffer.

Embodiment 20. The method of embodiment 19, wherein the pH of the solution comprising water and acetonitrile in ammonia buffer is adjusted to about pH 8.0.

Embodiment 21. The method of any one of embodiments 16-20, wherein step (a) comprises:

i) preparing a MBHA-resin on which the SPPS will be performed ii) performing an initial Fmoc deprotection reaction followed by a coupling reaction to add a first Fmoc-protected amino acid to the resin, thereby forming a protected peptide on the resin;

iii) performing an Fmoc deprotection reaction followed by a coupling reaction to append at least one Fmoc-protected amino acid to the protected peptide;

iv) repeating step iii until the GLP-2 analog peptide is synthesized on the resin to produce a Fmoc-protected and side-chain protected GLP-2 analog peptide linked to the resin;

v) performing an Fmoc deprotection reaction to produce a side-chain protected GLP-2 analog peptide linked to the resin; and vi) drying the side-chain protected GLP-2 analog peptide linked to the resin.

Embodiment 22. The method of embodiment 21, wherein step (a)(i) comprises:

(a1) washing the resin with a solution comprising dimethylformamide (DMF) and N,N-Diisopropylethylamine (DIEA) at 5 mL of solution per gram of resin under an $N_2$ atmosphere;

(b1) coupling a Rink amide linker to the resin in a solution comprising 2-(1H-benzotriazol-1-yl)-1,1,3,3-tetramethyluronium hexafluorophosphate, Hexafluorophosphate Benzotriazole Tetramethyl Uronium (HBTU), DIEA and Hydroxybenzotriazole (HOBt) in DMF;

(c1) washing the product formed in step (b1) with DMF (d1) performing a reduction reaction by contacting the resin with a solution comprising acetic anhydride ($Ac_2O$) and DIEA in DMF; and (e1) washing the product formed in step (d1) with DMF.

Embodiment 23. The method of embodiment 21 or embodiment 22 wherein performing an Fmoc deprotection reaction followed by a coupling reaction comprises:

(a2) treating the resin with a solution comprising piperidine in DMF;

(b2) washing the resin with DMF;

(c2) washing the resin with a solution comprising DMF and oxyma;

(d2) contacting the resin with at least one Fmoc-protected amino acid and a first amount of a solution comprising diisopropylcarbodiimide (DIC) and ethyl cyanohydroxyiminoacetate (oxyma);

(e2) contacting the resin with a second amount of a solution comprising DIC and oxyma; and (f2) washing the product formed in step (e2) with DMF.

Embodiment 24. The method of embodiment 23, wherein the resin is contacted with the second amount of a solution comprising DIC and oxyma about 30 minutes after contacting the resin with the first amount of a solution comprising DIC and oxyma.

Embodiment 25. The method of embodiment 21 or embodiment 22 wherein performing an Fmoc deprotection reaction followed by a coupling reaction comprises:

(a2) treating the resin with a solution comprising piperidine and oxyma in DMF;

(b2) washing the resin with DMF;

(c2) washing the resin with a solution comprising DMF and oxyma;

(d2) contacting the resin with at least one Fmoc-protected amino acid and a first amount of a solution comprising diisopropylcarbodiimide (DIC) and ethyl cyanohydroxyiminoacetate (oxyma);

(e2) contacting the resin with a second amount of a solution comprising DIC and oxyma; and (f2) washing the product formed in step (e2) with DMF.

Embodiment 26. The method of embodiment 25, wherein the resin is contacted with a first amount of a solution comprising piperidine and oxyma in DMF for 15 minutes followed by contacting the resin with a second amount of a solution comprising piperidine and oxyma in DMF for 30 minutes.

Embodiment 27. The method of any one of embodiments 23 to 26, wherein the at least one Fmoc-protected amino acid is Fmoc-Gln(Trt)-Thr($\psi^{Me,Me}$pro)-OH.

Embodiment 28. The method of any one of embodiments 23 to 26, wherein the at least one Fmoc-protected amino acid is Fmoc-Gly(Tmb)-OH.

Embodiment 29. The method of any one of embodiments 23 to 26, wherein the at least one protected amino acid is Boc-His(Trt)-Gly-OH.

Embodiment 30. The method of any one of embodiments 23-29, wherein the method further comprises, between steps (e2) and (f2), performing a coupling test, wherein the coupling test is a Kaiser test.

Embodiment 31. The methods of any of embodiments 16-30, wherein the GLP-2 analog peptide is apraglutide.

Embodiment 32. A composition comprising the GLP-2 analog peptide produced using the method of any of embodiments 16-31.

Embodiment 33. A method of treating short bowel syndrome associated intestinal failure (SBS-IF) or short bowel syndrome associated intestinal insufficiency (SBS-II) in a subject comprising administering apraglutide, or pharmaceutically acceptable salt thereof, to the subject, wherein the apraglutide or pharmaceutically acceptable salt thereof is administered at a dose of about 2.5 mg/week when the subject has a body weight of less than 50 kg, or wherein the apraglutide or pharmaceutically acceptable salt thereof is administered at a dose of about 5 mg/week when the subject has a body weight greater than or equal to 50 kg.

Embodiment 34. The method of embodiment 33, wherein the apraglutide, or pharmaceutically acceptable salt thereof, is administered by subcutaneous injection.

Embodiment 35. The method of embodiment 33 or embodiment 34, wherein the subject has colon-in-continuity, and wherein the apraglutide, or pharmaceutically acceptable salt thereof is administered for about 48 weeks.

Embodiment 36. The method of embodiment 35, wherein the subject has greater than 50% colon-in-continuity.

Embodiment 37. The method of embodiment 33 or embodiment 34, wherein the subject has at least one stoma, and wherein the apraglutide is administered for about 24 weeks.

Embodiment 38. The method of embodiment 33, wherein the administration of apraglutide or a pharmaceutically acceptable salt thereof increases the intestinal absorption of dietary intake wet weight in a subject relative to an untreated or placebo treated subject.

Embodiment 39. The method of embodiment 33, wherein the administration of apraglutide or a pharmaceutically acceptable salt thereof decreases fecal output in a subject relative to an untreated or placebo treated subject.

Embodiment 40. The method of embodiment 33, wherein the administration of apraglutide or a pharmaceutically acceptable salt thereof increases absolute urine volume output in a subject relative to an untreated or placebo treated subject.

Embodiment 41. The method of embodiment 33, wherein the administration of apraglutide or a pharmaceutically acceptable salt thereof increases intestinal absorption of sodium and potassium in a subject relative to an untreated or placebo treated subject.

Embodiment 42. The method of embodiment 33, wherein the administration of apraglutide or a pharmaceutically acceptable salt thereof increases sodium and potassium urine excretion in a subject relative to an untreated or placebo treated subject.

Embodiment 43. The method of embodiment 33, wherein the administration of apraglutide or a pharmaceutically acceptable salt thereof increases intestinal absorption of energy in a subject relative to an untreated or placebo treated subject.

Embodiment 44. The method of embodiment 33, wherein the administration of apraglutide or a pharmaceutically acceptable salt thereof decreases the energy content of fecal output in a subject relative to an untreated or placebo treated subject.

Embodiment 45. The method of embodiment 33, wherein the administration of apraglutide or a pharmaceutically acceptable salt thereof increases intestinal absorption of carbohydrates, proteins, and lipids in a subject relative to an untreated or placebo treated subject.

Embodiment 46. The method of embodiment 33, wherein the administration of apraglutide or a pharmaceutically acceptable salt thereof increases citrulline concentration in a subject relative to an untreated or placebo treated subject.

Embodiment 47. A sodium salt of apraglutide having a purity of no less than 95%, wherein apraglutide has the following structure:

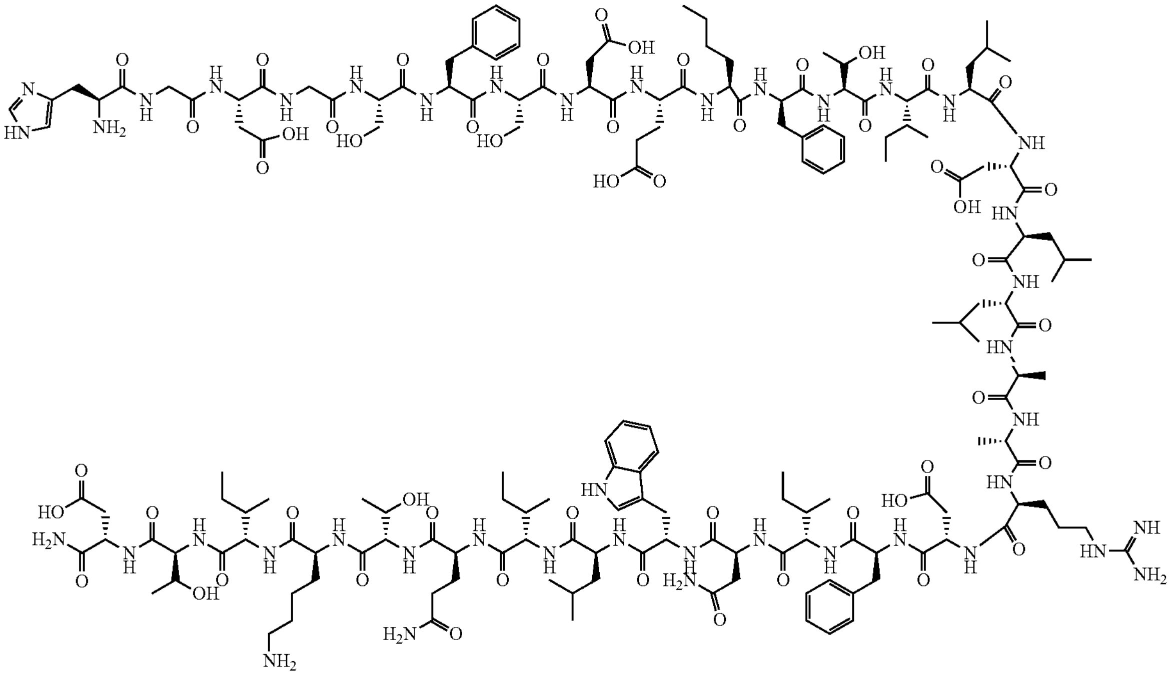

Embodiment 48. The sodium salt of apraglutide of Embodiment 47, wherein the sodium salt of apraglutide has a purity of no less than 97%.

Embodiment 49. The sodium salt of apraglutide of any one of the preceding embodiments, wherein the sodium salt of apraglutide comprises no more than 3% of a Des-Gly$^4$ apraglutide impurity.

Embodiment 50. The sodium salt of apraglutide of any one of the preceding embodiments, wherein the sum of Aspartimide$^3$ apraglutide, Asp$^{33}$-OH apraglutide and Des-Ser$^7$ apraglutide impurities in the sodium salt of apraglutide is no more than 2%.

Embodiment 51. The sodium salt of apraglutide of any one of the preceding embodiments, wherein the composition sodium salt of apraglutide no more than 2% of a [Trp$^{25}$, 2-(2,4,6-trimethoxyphenyl)] apraglutide impurity.

Embodiment 52. The sodium salt of apraglutide of any one of the preceding embodiments, wherein the sodium salt of apraglutide comprises no more than 1.5% of a 3-Asp$^3$ apraglutide impurity.

Embodiment 53. The sodium salt of apraglutide of any one of the preceding embodiments, wherein the sodium salt of apraglutide comprises no more than 1% of a R-Asp$^3$ apraglutide impurity.

Embodiment 54. The sodium salt of apraglutide of any one of the preceding embodiments, wherein the sodium salt of apraglutide comprises no more than 1% of a D-His apraglutide impurity.

Embodiment 55. The sodium salt of apraglutide of any one of the preceding embodiments, wherein the sodium salt of apraglutide comprises:

no more than 1% of a Asp$^{33}$-OH apraglutide impurity, no more than 1% of a Des-Ser$^7$ apraglutide impurity, no more than 1% of a D-Aspartimide$^3$ apraglutide impurity, no more than 1% of a [Trp$^{25}$, 2-(2,4,6-trimethoxyphenyl)] apraglutide impurity, and wherein the sum of Des-Gly$^4$ apraglutide and Aspartimide$^3$ apraglutide impurities in the sodium salt of apraglutide is no more than 1%.

Embodiment 56. The sodium salt of apraglutide of any one of the preceding embodiments, wherein the sodium salt of apraglutide is provided as a lyophilized powder.

Embodiment 57. A pharmaceutical composition comprising the sodium salt of apraglutide of any one of the preceding embodiments.

Embodiment 58. The pharmaceutical composition of embodiment 57, further comprising at least one of glycine, L-histidine and mannitol.

Embodiment 59. A pharmaceutical composition of embodiment 58, wherein the pharmaceutical composition comprises:

about 12.5 mg of apraglutide (sodium salt);

about 1.88 mg of glycine;

about 3.88 mg of L-histidine;

about 57.5 mg of mannitol.

Embodiment 60. The pharmaceutical composition of any one of embodiments 57-59, wherein the pharmaceutical composition is provided as a lyophilized powder.

Embodiment 61. A two-chamber powder syringe comprising the composition of any one of embodiments 47-56 or the pharmaceutical composition of any one of embodiments 57-60.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what is regarding as the invention.

Example 1: Apraglutide Manufacturing Process (I)

Solid Phase Peptide Synthesis (Step 1)

The following is an exemplary method of the present disclosure for the manufacture of apraglutide at improved levels of purity relative to previously described synthesis routes (e.g. U.S. Pat. No. 8,580,918). SPPS is the sequential synthesis of a peptide chain anchored on a solid support by repetition of a cycle encompassing the following steps:

1. Removal of the N-terminus Fmoc protecting group of the peptide resin
2. DMF washes
3. Couplings of Fmoc-AA-OH
4. Coupling test
5. DMF washes This cycle is repeated until the peptide sequence is completed.

The α-amino groups of the amino acids are protected with the base-sensitive 9-fluorenylmethyloxycarbonyl (Fmoc) group; the side chain functional groups are protected with acid-labile groups. All amino acids derivatives used in the process are commercially available.

SPPS is the sequential synthesis of a peptide chain anchored on a solid support. In the synthesis, MBHA resin may be used to assemble the peptide sequence. After swelling and washing the resin with DMF and then with DMF/DIEA under nitrogen atmosphere the Fmoc-Rink-amide linker may be coupled using HBTU/DIPEA/HOBt in DMF. After coupling, the resin may be washed with DMF and then acetylated using $Ac_2O$/DIPEA. A Kaiser test may be carried out to check completion of the coupling.

After washing the resin with DMF, the Fmoc protected amino acids are each coupled to the resin-bond peptide according to the following cycle:

1. The Fmoc-protecting group is removed with piperidine in DMF and the resin is washed thoroughly with DMF.
2. The coupling is performed in DMF with variable amino acid equivalents using DIC/oxyma for activation.
3. Coupling of amino acids is monitored by using the Ninhydrin assay, which is performed during each synthesis cycle.

At the end of the assembly, after the last amino acid has been coupled and deprotected, the resin is washed with DMF and isopropanol, and dried under vacuum.

Cleavage of the Peptide from the Resin and Deprotection (Step 2)

The protected peptide may be simultaneously cleaved from the resin and deprotected by treatment with a mixture TFA/water/anisole. MTBE is subsequently added to the peptide/TFA slurry to precipitate the crude peptide in the presence of cleaved resin. The obtained crude peptide is filtered, washed with MTBE and dried under vacuum to constant weight.

Decarboxylation Reaction (Step 3a)

The crude peptide is solubilized in a mixture of $H_2O$/ACN (80:20 ratio) in ammonia buffer. The solution is adjusted to target pH≥7 using 25% $NH_4OH$ in $H_2O$. The decarboxylation reaction is maintained at Room Temperature° for 24 hours. The crude peptide is washed with a solution of $H_2O$/ACN (80:20 ratio) in ammonia buffer at about pH 10 and stored at Room Temperature°.

Purification by Preparative RP-HPLC (Step 3b)

The crude peptide is dissolved in a mixture of water/acetonitrile/NH4OH. This solution is diluted with acetic acid and then filtered.

The primary purification is conducted on preparative RP-HPLC with $NaHCO_3/H_2O/CH_3CN$ as eluent. The elution from the column is monitored by UV and the fractions obtained are analyzed by RP-HPLC. Fractions meeting the monitoring criteria are mixed in the combined pool. Fractions not meeting the monitoring criteria may be recycled by repeating the purification step. The purity of the pool is controlled by analytical RP-HPLC.

Sodium Salt Conversion by Preparative RP-HPLC (Step 4)

This step may be conducted to exchange the counter ion of the peptide from a TFA anion to a sodium cation through a pH change and to further purify the peptide. The combined pool from Step 3 is diluted in water and re-purified by preparative RP-HPLC using NaOAc eluent.

The purified peptide solution is subsequently subject to evaporation under vacuum to reduce acetonitrile in the solution. The purified peptide solution is then adjusted to target pH 7.9 using 0.1% AcOH.

The pure pool may be concentrated and freeze-dried. The purity of the pool is analyzed by RP-HPLC.

Freeze-drying and Packaging (Step 5)

Prior to lyophilization, the purified peptide in solution is filtered through a 0.2 m membrane. The lyophilization is carried out at low pressure. The resulting lyophilized final peptide is packed under argon. The lyophilized apraglutide is controlled according to the apraglutide specification.

Reprocessing

Lyophilized apraglutide that does not fulfil the criteria established in the apraglutide specification may be subjected to re-purification.

Re-purification may be carried out after reconstitution of the peptide by repeating the purification step(s) and counterion conversion step, as described above.

After re-purification, the material is lyophilized according to the procedure described above.

Lyophilized apraglutide that does not fulfil the criteria established in the apraglutide specification may be subjected to re-lyophilization.

Re-lyophilization may be carried out after reconstitution of the peptide by repeating the lyophilization step, as described above.

Impurities

In some aspects of the methods of the present disclosure, the apraglutide is substantially free from organic impurities including, but not limited to, residues of the reagents and materials (including by-products) used in the manufacturing process.

In some aspects of the methods of the present disclosure, the apraglutide is substantially free from non-peptide impurities.

In some aspects of the methods of the present disclosure, the apraglutide is substantially free from residual solvents.

The peptide impurities, including but not limited to, Des-$Gly^4$ apraglutide, $Aspartimide^3$ apraglutide, $Asp^{33}$-OH apraglutide, Des-$Ser^7$ apraglutide, and [$Trp^{25}$, 2-(2,4,6-trimethoxyphenyl)] apraglutide may be observed in the apraglutide composition. Apraglutide for injection may be a lyophilized powder stored at the long term storage condition (5°±3° C.). The stability results provided herein (Table 5) demonstrate that no degradation has been observed at the long-term storage condition.

A test of bacterial endotoxins may be preferred to ensure the microbiological quality after manufacture, packaging, storage and distribution of the apraglutide composition, as required for a parenteral apraglutide composition. The test is performed according to Ph. Eur. 2.6.14/USP <85>.

Chemical Characteristics of Product

The compound of the present disclosure is a 33 amino acid synthetic peptide analogue of glucagon-like peptide-2

(GLP-2) that acts as a selective, full agonist of the GLP-2 receptor with potency and selectivity comparable to native GLP-2.

The peptide of the disclosure a linear peptide. The sequence of the peptide contains one D stereoisomer amino acid (D-phenylalanine), one unnatural amino acid (Norleucine) and two achiral amino acids (glycine); all other amino acids are L-configuration. The peptide of the disclosure is synthesized as a single enantiomer with all stereo-centers of defined chirality. It may be isolated in its sodium salt form with some residual water as a natural constituent.

The appearance of the disclosed peptide is a white to off-white homogenous powder. It may be isolated by reversed phase chromatography purification and subsequently lyophilized; no crystalline or polymorphic forms are known.

The solubility of the disclosed peptide in purified water is above 100 mg/mL.

The pH of a solution of the disclosed peptide in water at 100 mg/mL is 7.6 to 8.4. The calculated isoelectric point is 4.3a.

The optimum solubility and chemical stability of apraglutide was observed between pH 8.0 to 8.5.

In-Process Controls

In some embodiments, the purity of purified peptide pool as measured by RP-HPLC is greater than 95%, 97% or 99%. In some embodiments, the purity of purified peptide pool as measured by RP-HPLC is greater than 95%.

In some aspects, the in-process controls presented in Table 4 can be use in the methods of the present disclosure. In some aspects, the in-process controls presented in Table 4 can have a purity that is presented in the "Acceptance Criteria" column of Table 4:

TABLE 4

| In-Process Control Test | Steps in the Process | Analytical Principle | Acceptance Criteria |
|---|---|---|---|
| Purity of the crude peptide | Step 2: Cleavage of the peptide from the resin and side chain deprotection | RP-HPLC | Overall purity ≥ 50.0% (area) |
| Purity of purified peptide pool by RP-HPLC | Step 3: Purification by preparative RP-HPLC | RP-HPLC | Purity ≥ 95%<br>Sum of Des-Gly[4] apraglutide and Aspartimide[3] apraglutide ≤ 1.0%<br>Asp33-OH apraglutide ≤ 1.0%<br>Des-5er7 apraglutide ≤ 1.0%<br>[Trp25, 2-(2,4,6-trimethoxyphenyl)] apraglutide ≤ 2.0%<br>D-Aspartimide apraglutide ≤ 2.0% |
| Purity of peptide sodium salt | Step 4: Sodium salt conversion by preparative RP-HPLC | RP-HPLC | Purity ≥ 95%<br>Sum of Des-Gly[4] apraglutide and Aspartimide[3] apraglutide ≤ 1.0%<br>Asp33-OH apraglutide ≤ 1.0%<br>Des-5er7 apraglutide ≤ 1.0%<br>[Trp25, 2-(2,4,6-trimethoxyphenyl)] apraglutide ≤ 2.0%<br>D-Aspartimide[3] apraglutide ≤ 2.0% |

The manufacture process described in this example is herein referred to as Process A. Table 2a shows the purity of Apraglutide product produced using Process A, as well as the level of major contaminants. As shown in Table 2a and Table 2b, Process A can yield Apraglutide that has a purity of no less than 95%, and low levels of contaminants. Moreover, Process A exhibits product yields ranging from 15% to 22%.

Example 2: In Vitro Measurement of GLP-2 Agonist Activity

To determine activities of GLP-2 agonists of the present disclosure on the hGLP-2 receptor, a transcriptional reporter gene assay is used. Two constructs are transiently transfected into a human embryonic kidney cell line (HEK-293): an hGLP-2 receptor expression DNA construct and a reporter DNA construct containing intracellular cAMP-responsive promoter elements regulating expression of firefly luciferase. (See for example HimmLer et al., J. Recept. Res., (1993), 13, 79-74 for further guidance on this assay.)

Cells are exposed for 5 hours to serial dilutions of compounds diluted half-log per dose. After exposure to compounds, cells are lysed, luciferase activity is determined, and compound efficacies and EC50 values are determined by non-linear regression analysis. hGLP-2, a naturally occurring 33-amino acid peptide ligand, is used as an internal control in each experiment.

Example 3: Formulation

To generate a formulation suitable for subcutaneous injection, apraglutide is aseptically manufactured and freeze-dried into a powder together with the pharmaceutical excipients glycine, L-histidine, and mannitol. The freeze-dried powder is reconstituted with sterile water or buffer for injection.

To develop a lyophilized formulation, a screening study was conducted evaluate the optimal bulking agent and excipients to achieve the desired physical stability of apraglutide in the liquid phase. Initial testing of the bulking agents sucrose and mannitol demonstrated that both were suitable for the lyophilization process and in terms of reconstitution time, water content and visual inspection of the lyophilized products. The effect of concentrations and combination of the stabilizers with the two bulking agents, sucrose and mannitol, was investigated. Glycine and Tris were tested as buffering agents at concentrations of 20 Mm (1.50 mg/mL for Glycine and 2.4 mg/mL for Tris) and 40 mM (3.0 mg/mL for Glycine and 4.8 mg/mL for Tris), pH 8.2 to 8.5. All formulations were tested with or without the presence of L-histidine at a 20 mM (3.10 mg/mL) concentration and with either mannitol or sucrose as bulking agent. A total of eleven formulations were prepared using factorial design. The formulations were physically challenged by placement on an orbiting table and at an accelerated temperature of 40° C. for 3 days. Physical stability of the formulations was assessed by size exclusion chromatography, optical density and viscosity; chemical stability of apraglutide was assessed by reversed phase liquid chromatography and size exclusion chromatography. The chemical and physical stability of formulations containing glycine in combination with histidine were superior to formulations containing Tris-buffer. Mannitol and sucrose were both suitable as bulking agents; however, mannitol was chosen due to the better processability during lyophilization.

As the effect of glycine concentration could not be concluded from the screening study, a laboratory scale stability study was set up with two formulations containing glycine at concentrations of 20 Mm (1.50 mg/mL) and 40 Mm (3.0 mg/mL), respectively. Both formulations contained 1-histidine, mannitol, apraglutide, and pH adjusted to 8.3. The formulations were freeze-dried and followed for 3 months at −20° C., 5° C., 25° C. and 40° C. The conclusions were that at −20° C., 5° C., and 25° C., both formulations were chemically and physically stable throughout the testing period of 3 months. At 40° C., both formulations showed signs of decreased physical stability at 3 months. The formulation containing the lower concentration of 20 mM glycine had a preferred higher degree of crystallinity of the mannitol when assessed by X-ray powder diffraction. Hence, 20 mM glycine was chosen for the formulation.

Example 4: Citrulline as a Marker for Apraglutide Effect

Plasma citrulline was used as a pharmacodynamic ("PD") marker to describe the effect of apraglutide. Similar to the pharmacokinetic ("PK") model development, the PK/PD model was developed for the healthy individuals from studies GLY-101-2015 and TA799-002 only. For development of the PD model, the PD observations were fitted together with the PK observations using the final PK model with its structure, residual error-, covariates- and random effects-models. The starting model was a turnover model where plasma citrulline was constantly synthesized and degraded with the synthesis rate ksyn and the degradation rate kdeg. Plasma apraglutide stimulated citrulline synthesis via a sigmoid Emax relationship with the baseline citrulline level R0, the half-maximal effect at the concentration EC50, the maximal effect Emax, and a Hill coefficient gamma. It was assumed that citrulline turnover was in steady state such that citrulline synthesis was determined solely by citrulline baseline and degradation. The population PK/PD of plasma apraglutide was established with data from two studies in healthy volunteers and two studies with SBS patients that tested doses between 2.5 and 50 mg SC. The concentration of apraglutide followed two-compartmental and dose-nonlinear kinetics. Apraglutide clearance was estimated to 16.8 L/day, the central volume of distribution to 31.5 L for a 70-kg individual receiving a 5 mg SC dose. The half-life was estimated to 1.3 days. The volume of distribution and the clearance were body weight dependent with coefficients $\beta_{V1/F,BW}$=1.94, and $\beta_{C1/F,BW}$=1.8. These coefficients indicated a strong body weight dependence. Zero-order absorption duration was dependent on dose with a coefficient of $\beta_{Tk0,Dose}$=0.249.

The effect of plasma apraglutide on plasma citrulline was found to be sigmoidal with a citrulline saturation appearing at doses of 5 mg. This phenomenon was described with a citrulline turnover model whose synthesis was stimulated according to an $E_{max}$ model by apraglutide. Citrulline baseline was found to be 5.12 μg/mL, while the maximal effect was 0.626, and the half-maximal effective apraglutide concentration was 13.7 ng/mL.

The population PK/PD model was used to predict plasma apraglutide exposure and plasma citrulline trough concentration-time profiles with and without inter-individual variability for individuals with body weights between 40 and 120 kg receiving weekly doses of 2.5, 5, or 10 mg SC. Predictions without inter-individual variability showed that the effect of apraglutide on citrulline begins to saturate for a 40 kg individual receiving weekly 5 mg apraglutide SC, i.e. with decreasing body weight the same apraglutide dose resulted in a decreasing effect on citrulline. This saturation effect was found to be even more pronounced for individuals receiving weekly 10 mg apraglutide SC. Predictions with inter-individual variability displayed a large variability in plasma citrulline concentration-time profiles and plasma citrulline trough levels. Apraglutide exposure for body weights between 40 and 120 kg and apraglutide SC doses of 2.5, 5, or 10 mg was compared to post-hoc exposure estimates of SBS patients. Bracketing at a body weight of 50 kg between doses of 2.5 and 5 mg was simulated. This bracketing variant resulted in apraglutide exposures within the range of post-hoc AUC estimates of SBS patients receiving weekly 5 mg apraglutide SC. As clinical biomarker, urinary output was correlated to post-hoc estimates of plasma apraglutide exposure and plasma citrulline trough levels in SBS patients. It was found that apraglutide exposure and citrulline trough levels only correlated weakly with urinary output.

Plasma citrulline, a biomarker for enterocytic mass, is increased after GLP-2 analog administration in human clinical trials.

The pharmacokinetic/pharmacodynamic (PK/PD) relationship between apraglutide, a novel long-acting GLP-2 analog in development for short bowel syndrome, and citrulline was evaluated in a randomized, double-blind, parallel arm, placebo-controlled, multiple dose study. 23 healthy adult volunteers received 6 weekly subcutaneous doses of apraglutide (1, 5, or 10 mg) or placebo and were followed for a further 6 weeks after the last dose. Blood collections were controlled for diet, lifestyle, and diurnal effects. L-citrulline was quantified using a validated LC-MS method. PK data underwent non-compartmental analysis and PD data were analyzed by ANCOVA.

PK parameters indicated a half-life of 72 hours. Increases in citrulline were observed 2 days after the first apraglutide dose and maximal effect was achieved in most subjects after 4 or 7 days. Mean citrulline levels were elevated from baseline in all apraglutide arms and remained elevated during the 6-week treatment period. Citrulline increases were significantly greater with apraglutide 5 mg and 10 mg than with apraglutide 1 mg versus placebo (Table 5). There were no statistically significant differences between 5 and 10 mg apraglutide dose levels. Plasma citrulline levels remained elevated for 10 to 17 days after the final apraglutide dose. Apraglutide was safe and well-tolerated with no serious AEs.

TABLE 5

| Apraglutide dose (mg) | Difference in citrulline (μg/mL) vs placebo | P-value |
|---|---|---|
| 1 | 0.31 [95% CI: −0.4371; 1.0663] | 0.3910 |
| 5 | 1.26 [95% CI: 0.5037; 2.0112] | 0.0025 |
| 10 | 1.63 [95% CI: 0.8809; 2.3878] | 0.0002 |

Apraglutide was safe and well tolerated, and displayed a PD response longer than plasma exposure. These PK and PD data confirm the potential for once-weekly subcutaneous dosing of apraglutide.

Example 5: Phase II Human Clinical Trial Results of Administration of Apraglutide Compositions of the Present Disclosure The following non-limiting example describes results from a Phase 2 clinical trial in which subjects with SBS-IF were treated with the apraglutide formulations of the present disclosure. This Phase 2 trial investigated the safety and efficacy of 5 and 10 mg apraglutide in patients with SBS-IF.

Without wishing to be bound by theory, the beneficial effects of GLP-2 analogues in SBS patients may include dynamic changes in body fluid homeostasis, which may be considered when evaluating treatment outcomes. Improved intestinal absorption results in decreased fecal output. Since large amounts of the intestinally absorbed water and sodium is excreted by the kidneys though the systemic circulation, an increased absorption in SBS patients can lead to an increase in urine volume production and sodium excretion. Therefore, in general, the hydration state of the SBS patient can be monitored by measuring urine volume and urine sodium.

Eight adult patients with SBS-IF were treated with apraglutide compositions of the present disclosure according to Table 6. Briefly, patients with SBS-IF were administered 5 mg apraglutide of the present disclosure or placebo once a week for four weeks. The patients were then administered 10 mg apraglutide of the present disclosure once a week for four weeks. Additionally, there was a washout period of 6-10 weeks between treatments.

TABLE 6

| Part A: Treatment period 1 (4 weeks) Randomized | Washout 1 (6-10 weeks after last dose) | Part A: Treatment period 2 (4 weeks) Randomized | Washout 2 (6-10 weeks after last dose) | Part B: Treatment period 3 (4 weeks) Open-label |
|---|---|---|---|---|
| Placebo or 5 mg apraglutide subcutaneously once weekly | | Placebo or 5 mg apraglutide subcutaneously once weekly | | 10 mg apraglutide subcutaneously once weekly |

Results

As part of the trial, a total of 12 patients were screened, and out of them, 8 were randomized for treatment. All 8 patients continued in the additional treatment period in an open-label regimen with 10 mg apraglutide (Part B). One patient discontinued the trial after first drug administration in the Part B treatment period due to exhaustion from trial procedures and a perceived lack of effect. The patient provided data for the immediate measurements but not post-treatment. Eight patients comprised the safety analysis set and the full analysis set. Demographics and baseline characteristics of the patients are summarized in Table 7. Data in Table 7 are mean (SD) or N (%) and parenteral support (PS) was scheduled PS at trial entry based on a weekly average.

Three patients had previously been treated with a GLP-2 analogue in a clinical trial (≥6 months ago). Individual patient plots illustrated that all effects reverted to baseline after the washout period; thus, no carryover effect was observed.

TABLE 7

| | |
|---|---|
| Age (years) | 59.1 (13.8) |
| Sex | |
| Female | 4 (50%) |
| Male | 4 (50%) |
| Weight at baseline | 75.6 (15.5) |
| Body-mass index (kg/m2) | 24.8 (3.9) |
| Race, white | 8 (100%) |
| Parenteral support volume (mL/day) | 3,309 (1,903) |
| Parenteral support energy (kJ/day) | 4,665 (3,852) |
| Urine volume output (mL/day) | 2,031 (1,112) |
| Oral fluid intake (mL/day) | 2,799 (1,289) |
| Urine sodium excretion | 73 (94) |
| Plasma citrulline levels (μmol/L) | 33 (30) |
| Cause of resection | |
| Crohn's disease | 2 (25%) |
| Mesenteric vascular disease | 3 (37.5%) |
| Surgical complications to ulcerative colitis | 1 (12.5%) |
| Surgical complications | 2 (25%) |
| Disease characteristics | |
| Small bowel length (cm) | 109 (127) |
| End-jejunostomy | 6 (75%) |
| Ileostomy | 2 (25%) |
| Colon in continuity | 0 |
| Concomitant medication | |
| Proton-pump inhibitor | 7 (87.5%) |
| Opioids or opioid agonists | 4 (50%) |
| Loperamide | 3 (37.5%) |

Total (N = 8)

Safety Results

Common related adverse events are reported in Table 8 (data are N or N (%)). Adverse events that occurred in >2 patients and included polyuria (n=7), stoma complications (n=6), gastrointestinal stoma complication (n=5), gastrointestinal stoma output decreased (n=6), gastrointestinal stoma output abnormal (n=5), decreased thirst (n=5), edema (n=4), increased weight (n=3) and decreased appetite (n=3). Three patients experienced injection site reactions. All injection site reactions occurred with active treatment; one patient had an injection site reaction in the 5 mg dose group, and three patients had an injection site reaction in the 10 mg dose group. A total of 8 cases of serious adverse events were reported by 5 patients. None of these were considered related to the trial drug. Two serious adverse events involved mechanical complications related to the tunneled central venous catheter used by the patients for PS administration, and both required hospitalization for catheter replacement. Six serious adverse events were catheter related blood stream infections (CRBSIs). One patient had four recurrent events of CRBSI. Serious adverse events were distributed equally between placebo and treatment periods. Most patients had at least one treatment related adverse event, all of which were mild to moderate with no obvious difference between the active dose levels.

TABLE 8

| | Placebo (N = 8) | 5 mg (N = 8) | 10 mg (N = 8) | Total (N = 8) |
|---|---|---|---|---|
| Any related adverse events | 8 | 8 | 8 | 8 (100%) |
| Polyuria | 1 | 4 | 6 | 7 (88%) |
| Gastrointestinal stoma output decreased | 0 | 3 | 6 | 6 (75%) |
| Stoma complication | 0 | 6 | 6 | 6 (75%) |
| Gastrointestinal stoma complication | 0 | 5 | 5 | 5 (63%) |
| Gastrointestinal stoma output abnormal | 0 | 4 | 4 | 5 (63%) |
| Thirst decreased | 0 | 3 | 4 | 5 (63%) |
| Edema | 0 | 2 | 2 | 4 (50%) |
| Increased weight | 0 | 1 | 2 | 3 (38%) |
| Decreased appetite | 0 | 1 | 2 | 3 (38%) |

There were no trial discontinuations or reductions due to related adverse events. One patient omitted the third dose of apraglutide during the placebo period due to peripheral edema. No safety concerns were raised from vital signs, blood samples, ECG, dipstick urinalysis or body weight. There were no deaths.

Three patients developed anti-apraglutide antibodies during the trial. Two patients tested positive for anti-apraglutide antibodies at the end of the 5 mg treatment period, and one at the end of the 10 mg treatment period. One patient who had positive antibodies at the end of the 5 mg treatment period, also had positive antibodies in the end of the 10 mg treatment period. For the two patients who developed positive antibodies during the 5 mg treatment period, they were negative after a 6-10 week washout period. For the two patients with positive antibodies at the end of the 10 mg treatment, both were still positive after a 4-6 weeks washout period, but the titres were lower than at the end of the 10 mg treatment period. No effects of anti-apraglutide antibodies were detected on the PK profile, the pharmacodynamic response to apraglutide, or on the number or duration of adverse events.

Urine Volume Output and Urine Sodium Excretion: Changes from Baseline to End of Treatment (Day 27-29)

The individual changes from baseline to end of each treatment in absolute urine volume output are plotted in FIG. 5, including the mean change for each treatment. The mean change differed from the adjusted mean calculated in the statistical analyses, which compares treatments to placebo. For the statistical analysis of Part A+B, 5 mg apraglutide promoted the increase of absolute urine volume output by an adjusted mean of 711 mL/day (95% CI 132 to 1,289; P=0.021) compared to placebo, corresponding to a daily increase of 48% (95% CI 12 to 84; P=0.014), as shown in Table 9. For the statistical analysis of Part A, 5 mg apraglutide promoted the increase of absolute urine volume output by an adjusted mean of 714 mL/day (95% CI 490 to 939; P=0.002), corresponding to a daily increase of 49% (95% CI 4 to 94; P=0.041), as shown in Table 10. Treatment with 10 mg apraglutide promoted the increase of absolute urine volume output by an adjusted mean of 795 mL (95% CI 195 to 1,394; P=0.014) compared to placebo. The corresponding change in relative urine production was 34% (95% CI−4 to 71; P=0.072). No difference was seen between the 5 mg and 10 mg dose groups, as shown in Table 9. In Table 9, the data are shown as an adjusted mean (95% CI), calculations are based on changes from baseline to end of treatment or near end of treatment of individual dose groups, and N denotes the number of patients in the full analysis set. The results from the statistical analysis of Part A+B are presented graphically in FIG. 6.

TABLE 9

| | Analysis Part A + B | | |
|---|---|---|---|
| | 5 mg vs placebo (N = 8) | 10 mg vs placebo (N = 8) | 5 mg vs 10 mg (N = 8) |
| Absolute urine output (mL/day) | 711 (132 to 1,289); P = .021 | 795 (195 to 1,394); P = .014 | 84 (−514 to 682); P = .761 |
| Relative urine output (%) | 48(12 to 84); P = .014 | 34 (−4 to 71); P = .072 | −14 (−51 to 23); P = .420 |
| Urine sodium excretion (mmol/day) | 56 (−10 to 123); P = .087 | 88 (20 to 156); P = .017 | 32 (−37 to 101); P = .325 |
| Urine sodium excretion (%) | 166 (−342 to 675); P = .478 | 432 ( −87 to 951); P = .092 | 266 (−266 to 798); P = .287 |
| PS volume (mL/day) | −89 (−543 to 366); P = .676 | −469 (−941 to 4); P = .052 | −380 (−851 to 91); P = .103 |
| Relative PS volume (%) | −13 (−36 to 9); P = .225 | −28 (−51 to −4); P = .025 | −15 (−38 to 9); P = .195 |
| Oral fluid intake (mL/day) | −244 (−512 to 23); P = .070 | −363 (−641 to −86); P = .015 | −119 (−396 to 157); P = .362 |
| Relative oral fluid intake (%) | −9 (−18 to 1); P = .072 | −15 (−25 to −5); P = .006 | −7 (−17 to 3); P = .169 |

The individual changes from baseline to end of each treatment in absolute urine sodium excretion are plotted in FIG. 7. For the statistical analysis of Part A+B, 5 mg apraglutide increased urine sodium excretion compared to placebo by an adjusted mean of 56 mmol/day (95% CI−10 to 123; P=0.087), as shown in Table 9. For the statistical analysis of Part A, 5 mg apraglutide increased urine sodium excretion compared to placebo by an adjusted mean of 66 mmol/day (95% CI−69 to 201; P=0.171), as shown in Table 10. In Table 10, the data are shown as an adjusted mean (95% CI), calculations are based on changes from baseline to end of treatment of individual dose groups, and N denotes the number of patients in the full analysis set. In the 10 mg dose group, absolute urine sodium excretion was increased by an adjusted mean of 88 mmol/day (95% CI 20 to 156; P=0.17) compared to placebo, as shown in Table 9. As shown in Tables 9 and 10, relative urine sodium excretion was not changed following apraglutide treatment. As further shown in Table 9, no difference was found between the 5 mg and 10 mg dose groups.

TABLE 10

| | Analysis Part A 5 mg vs placebo (N = 8) |
|---|---|
| Absolute urine output (mL/day) | 714 (490 to 939); P = .002 |
| Relative urine output (%) | 49 (4 to 94); P = .041 |
| Urine sodium excretion (mmol/day) | 66 (−69 to 201); P = .171 |
| Urine sodium excretion (%) | 189 (−350 to 729); P = .270 |
| PS volume (mL/day) | −94 (−344 to 156); P = .356 |
| Relative PS volume (%) | −13 (−41 to 15); P = .276 |
| Oral fluid intake (mL/day) | −242 (−560 to 76); P = .103 |
| Relative Oral fluid intake (%) | −9 (−18 to 1); P = .068 |

Urine Volume Output and Urine Sodium Excretion: Changes from Baseline to Immediately after First Treatment Injection (Day 1-3)

The individual changes from baseline to immediately after first treatment injection in absolute urine output and urine sodium excretion are shown plotted in FIGS. 8 and 9, respectively. No immediate changes were observed for the 5 mg or 10 mg dose group compared to placebo, and there were no differences between the active dose groups, as shown in Table 11. In Table 11, the data are shown as an adjusted mean (95% CI) and calculations are based on changes from baseline to immediately after first treatment injection of individual dose groups, and N denotes the number of patients in the full analysis set.

TABLE 11

| | Analysis Part A + B | | | Analysis Part A |
|---|---|---|---|---|
| | 5 mg vs placebo (N = 8) | 10 mg vs placebo (N = 8) | 5 mg vs 10 mg (N = 8) | 5 mg vs placebo (N = 8) |
| Absolute urine output (mL/day) | −38 (−456 to 381); P = .845 | −64 (−500 to 372); P = .751 | −26 (−462 to 409); P = .896 | −48 (−696 to 601); P = .831 |
| Relative urine output (%) | 6 (−24 to 35); P = .678 | −6 (−37 to 24); P = .655 | −12 (−43 to 19); P = .402 | 5 (−38 to 48); P = .729 |
| Urine sodium excretion (mmol/day) | 3 (−17 to 23); P = .705 | 3 (−17 to 22); P = .768 | −1 (−22 to 20); P = .930 | 3 (−146 to 152); P = .823 |
| Urine sodium excretion (%) | 65 ( −36 to 166); P = .176 | 22 ( −75 to 119); P = .617 | −43(−149 to 63); P = .375 | 64 (−306 to 433); P = .272 |

Oral Fluid Intake: Changes from Baseline to Near End of Treatment (Day 20-22)

At days 20-22, treatment with 10 mg apraglutide decreased absolute and relative oral fluid intake by an adjusted mean of 363 mL/day (95% CI−641 to −86; P=0.015) and −15% (95% CI−25 to −5; P=0.006) respectively. For the analysis of Part A+B, a similar trend was seen for the 5 mg dose group with an adjusted mean reduction of 244 mL/day (95% CI−512 to 23; P=0.070), as shown in Table 9, and for the analysis of Part A with a mean reduction of 242 mL/day (95% CI−560 to 76; P=0.103), as shown in Table 10. Further, as shown in Table 9, no difference was found between the active dose groups.

PS Volume: Changes from Baseline to Near End of Treatment (Day 20-22)

At days 20-22, 10 mg apraglutide decreased relative daily PS volume by −28% (−51 to −4; P=0.025) compared to placebo. A similar trend was seen for the absolute change in daily PS volume which decreased by 469 mL/day (−941 to 4; P=0.052), as shown in Table 9. No changes in PS volume were observed for the 5 mg dose group, as shown in Tables 9 and 10, and no difference was seen between the 5 mg and 10 mg dose groups, as shown in Table 9.

Fluid Composite Effect: Changes from Baseline to Near End of Treatment (Day 20-22)

A post-hoc analysis for Part A+B was performed to calculate the fluid composite effect, defined as the sum of increase urine production (day 27-29), reduction in PS volume and reduction in spontaneous oral fluid intake (day 20-22). Spontaneous oral fluid intake and PS volume reduction were assessed near the end of treatment period, since they were kept unchanged during urine collections. Administration of 5 mg and 10 mg apraglutide increased the fluid composite effect compared to placebo by 1,036 mL/day (95% CI 262 to 1,810; P=0.014) and 1,630 mL/day (95% CI 827 to 2,433; P=0.001), respectively. There was no difference between the two doses; the estimated difference was 594 (95% CI−207 to 1,396; P=0.129). Individual plots of the fluid composite effect together with urine volume output at end of treatment are shown in FIGS. 10A-C.

Hydration Status Parameters

In a post-hoc analysis of Part A+B apraglutide, 5 mg and 10 mg reduced plasma aldosterone by 2,894 μmol/L (95% CI−6247 to 458; P=0.083) and 3,045 μmol/L (95% CI−6,460 to 370; P=0.075), respectively. Apraglutide did not change other hydration parameters including creatinine, urea, hematocrit, albumin, protein and $CO_2$ total, as shown in Table 12. In Table 12, the data are shown as an adjusted mean (95% CI), calculations are based on changes from baseline to end of treatment of individual dose groups, and N denotes the number of patients in the full analysis set.

TABLE 12

| | Analysis Part A + B | | |
|---|---|---|---|
| | 5 mg vs placebo (N = 8) | 10 mg vs placebo (N = 8) | 5 mg vs 10 mg (N = 8) |
| Aldosterone (pmol/L) | −2,894 (−6,247 to 458); P = .083 | −3,045 (−6,460 to 370), P = .075 | −151 (−3,570 to 3,268); P = .924 |
| Creatinine (umol/L) | −9.7(−25.8 to 6.4); P = .214 | −5.1 (−22.1 to 11.9); P = .525 | 4.6 (−12.3 to 21.5); P = .567 |
| Urea (mmol/L) | −0.9 (−2.4 to 0.6); P = .217 | −0.6 (−2.2 to 1.0); P = .425 | 0.3 (−1.3 to 1.9); P = .691 |
| Hematocrit (vol/fr) | 0.6 (−0.2 to1.4); P = .151 | 0.2 (−0.7 to 1.0); P = .675 | −0.4 (−1.2 to 0.4); P = .326 |
| Albumin (g/L) | −0.0 (−1.8 to 1.8); P = .996 | 1.0 (−0.9 to 2.9); P = .260 | 1.0 (−0.8 to 2.9); P = .248 |
| Protein (g/L) | −0.4 (−4.2 to 3.4); P = .824 | −0.7 (−4.7 to 3.3); P = .704 | −0.3 (−4.5 to 3.9); P = .874 |
| CO2 total (mmol/L) | 0.3 (−2.0 to 2.6); P = .788 | 1.3 (−1.1 to 3.7); P = .272 | 1.0 (−1.4 to 3.4); P = .393 |

Plasma L-Citrulline

In the statistical analysis of Part A+B, 5 mg apraglutide increased absolute plasma L-citrulline by an adjusted mean of 17.6 μmol/L (95% CI 2.0 to 33.2; P=0.031) corresponding to increases of 65% (95% CI 15 to 115; P=0.015). In the statistical analysis of Part A, 5 mg apraglutide increased absolute plasma L-citrulline by an adjusted mean of 17.7 μmol/L (95% CI−6.3 to 41.7; P=0.100) corresponding to a relative increase of 66% (95% CI−13 to 145; P=0.077). The differences in change from baseline for the 10 mg dose vs placebo were smaller as shown in Table 13. In Table 13, the data are shown as an adjusted mean (95% CI), calculations are based on changes from baseline to end of treatment of individual dose groups, and N denotes the number of patients in the full analysis set. The individual changes from baseline in absolute concentration of plasma L-citrulline are plotted in FIG. 11. Mean change and individual patient plasma L-citrulline changes from baseline are plotted in FIG. 27. Dose-dependent increases in plasma citrulline levels were observed with apraglutide, starting 2 days after the first dose. As shown in FIG. 28, following three weekly doses of apraglutide compared with placebo, citrulline levels increased significantly.

TABLE 13

| | Analysis Part A + B | | | Analysis Part A |
|---|---|---|---|---|
| | 5 mg vs placebo (N = 8) | 10 mg vs placebo (N = 8) | 5 mg vs 10 mg (N = 8) | 5 mg vs placebo (N = 8) |
| Plasma L-citrulline (μmol/L) | 17.6 (2.0 to 33.2); P = .031 | 14.0 (−2.3 to 30.3); P = .084 | −3.6 (−19.8 to 12.6); P = .632 | 17.7 (−6.3 to 41.7); P = .100 |
| Relative plasma L-citrulline (%) | 65 (15 to 115); P = .015 | 42 (−10 to 94); P = .100 | −23 (−74 to 29); P = .344 | 66 (−13 to 145); P = .077 |

Body Weight and Body Composition

For the analysis of Part A+B, 5 mg apraglutide significantly increased absolute and relative fat mass by 1.77 kg (95% CI 0.29 to 3.24; P=0.024) and 10% (95% 1 to 18; P=0.035), respectively. Corresponding to the increase in fat mass, 5 mg apraglutide increased body weight by 1.9 kg (95% CI 0.1 to 3.7; P=0.043). No changes were found in lean body mass or bone mineral content for any of the dose groups compared to placebo. In the statistical analysis of Part A, a trend in increased fat mass and body weight was observed for 5 mg apraglutide, as shown in Table 14. In Table 14, the data are shown as an adjusted mean (95% CI), calculations are based on changes from baseline to end of treatment of individual dose groups, and N denotes the number of patients in the full analysis set.

TABLE 14

| | 5 mg vs placebo (N = 8) | Analysis Part A + B 10 mg vs placebo (N = 8) | 5 mg vs 10 mg (N = 8) | Analysis Part A 5 mg vs placebo (N = 8) |
|---|---|---|---|---|
| Body weight (kg) | 1.9 (0.1 to 3.7); P = .043 | 1.3 (−0.6 to 3.2); P = .151 | −0.6 (−2.4 to 1.3); P = .517 | 1.9 (−0.8 to 4.5); P = .128 |
| Relative body weight (%) | 3 (0 to 6); P = .042 | 2 (−1 to 5); P = .159 | −1 (−4 to 2); P = .487 | 3 (−1 to 7); P = .117 |
| Lean body mass (kg) | 0.64 (−2.49 to 3.77); P = .656 | 0.76 (−2.47 to 3.99); P = .608 | 0.12 (−3.00 to 3.24); P = .932 | 0.49 (−4.65 to 5.64); P = .721 |
| Relative lean body mass (%) | 2 (−5 to 9); P = .521 | 2 (−6 to 9); P = .613 | −0 (−8 to 7); P = .900 | 2 (−11 to 15); P = .547 |
| Fat body mass (kg) | 1.77 (0.29 to 3.24); P = .024 | 0.33 (−1.20 to 1.85); P = .641 | −1.44 (−2.92 to 0.04); P = .055 | 1.74 (−0.36 to 3.83); P = .071 |
| Relative fat body mass (%) | 10 (1 to 18); P = .035 | 2 (−7 to 11); P = .608 | −7 (−16 to 1); P = .086 | 9 (−5 to 24); P = .110 |
| Bone mineral content (g) | −4 (−73 to 66); P = .905 | 8 (−64 to 81); P = .799 | 12 (−57 to 82); P = .700 | −4 (−132 to 123); P = .896 |
| Relative bone mineral content (%) | 0 (−3 to 3); P = .916 | 0 (−3 to 3); P = .891 | 0 (−3 to 3); P = .967 | 0 (−6 to 6); P = .927 |

Pharmacokinetics

The plasma concentration of apraglutide increased after dosing, with the maximum mean concentration measured 72 hours after dosing. The mean plasma concentration of apraglutide before the second dose ($C_{trough}$) was 4.5 ng/mL and 8.9 ng/mL in the 5 mg and 10 mg treatment periods, respectively.

Summary of Example 5

The results described in Example 5 demonstrate that the administration of apraglutide compositions of the present disclosure to subjects was safe, well tolerated and induced beneficial changes in intestinal fluid absorption, including, but not limited to, increases in urine volume.

Treatment related adverse events were mild to moderate and corresponded to the physiological effect of GLP-2. There was no dose-dependency for adverse events. Injection site reactions were few, reflecting the just once weekly dosing regimen. There were no events of treatment related abdominal pain or distension.

Treatments with once weekly 5 and 10 mg apraglutide doses increased urine volume output when compared against placebo. 10 mg apraglutide significantly increased urine sodium excretion at end of treatment and reduced oral fluid intake as well as PS volume (assessed near end of treatment). Similar trends were seen for the 5 mg dose for urine sodium excretion and oral fluid intake.

Collectively, these increases in urine volume reflect increased intestinal fluid and sodium absorption. Without wishing to be bound by theory, this is an important effect for patients with SBS, who are at high risk of dehydration, sodium depletion and renal impairment. Fluid and electrolyte abnormalities may also be a cause of morbidity and hospitalizations.

Due to the relatively short treatment period of 4 weeks, reductions in PS volume were made if there were clinical signs of fluid retention. It is envisioned that during long-term apraglutide treatment, increases in urine output may enable further reductions in PS volume as also evidenced by the larger fluid composite effect. Treatment with 5 mg apraglutide increased relative urine volume output in 6 out of 8 patients compared to placebo and exceeded the 10% increase which would have triggered a reduction in PS volume.

Plasma concentration of L-citrulline increased during both active treatment periods. Without wishing to be bound by theory, this indicates an increased enterocyte mass and is consistent with the intestinotrophic effects of apraglutide on the intestinal epithelium. In two patients who had clinically significant increases in urine output (assessed day 27-29) in the 5 mg treatment period, a diminished effect of 10 mg was observed. However, these patients had concomitant reductions in PS volume and oral fluid intake (assessed day 20-22) during the 10 mg treatment period, leading to a positive fluid composite effect, defined as the sum of beneficial effects including increase in urine production, reduction in the need for PS volume and reduction in oral fluid intake.

As would be appreciated by the skilled artisan, patients with SBS may suffer from secondary hyperaldosteronism due to excessive fecal sodium losses and chronic sodium depletion. In the trial described in Example 5, it was found that administration of apraglutide tended to decrease aldosterone levels in both dose groups compared to placebo. Without wishing to be bound by theory, this indicates that apraglutide alleviates secondary hyperaldosteronism due to improved fluid and sodium absorption.

Treatment with 5 mg apraglutide was associated with an increased fat mass and body weight This is the first time an increase in fat mass was observed in a subject after treatment with a GLP-2 or GLP-2 analogue t. Increases in body weight correlate well to corresponding changes in fat mass and/or lean mass.

The statistical analysis described in Example 5 was carried out in two versions, Part A compared 5 mg to placebo, whereas Part A+B included placebo, 5 mg and 10 mg to estimate the contrasts between the three treatments. The results of the Part A and Part A+B analysis were generally the same.

In summary, the results described in Example 5 demonstrate that 5 and 10 mg of once weekly apraglutide dosing for four weeks was well tolerated and safe. The results also demonstrated clinical effects of a GLP-2 analogue with weekly dosing. Once weekly treatment with apraglutide increased urine volume output and improved other markers of intestinal rehabilitation in patients with SBS at both tested doses (5 and 10 mg) although no differences in response were observed. It is envisioned that apraglutide compositions of the present disclosure may contribute to patient care and compliance by enabling once weekly, as opposed to daily, administration, which in turn may improve quality of life. The reduced injection frequency may increase patient acceptability and decrease the risk of injection site reactions. These results indicate that apraglutide treatment leads to increased intestinal absorption through promoting intestinal adaptation. Without wishing to be bound by theory, these results indicate that the treatment with apraglutide in vivo can improve intestinal wet weight absorption in a patient with SBS-IF, and therefore can be implemented in a therapeutic setting.

Methods

Trial Design and Participants

The trial described in Example 5 was a double-blind, crossover, randomized, placebo-controlled, phase 2 trial followed by an additional treatment period in an open-label regimen. Eight adult patients (aged ≥18 to ≤80 years) with SBS-IF were enrolled in the trial. Patient eligibility was assessed during a screening visit. The main inclusion criteria were: Patients with SBS secondary to surgical resection of the small bowel with a jejuno- or ileostomy, at least 6 months since last bowel resection, a fecal output of at least 1500 g/day as recorded within the last 18 months, and PS-infusions ≥3 times per week for ≥12 months according to the patient's medical record. Patients were excluded, if they had clinical signs of activity in inflammatory bowel disease, a history of cancer within ≤5 years or an inadequate hepatic, kidney, or heart function. Patients were also excluded, if they had received native GLP-2 or a GLP-2 analogue within the last 3 months.

As shown in FIG. 4, the trial was organized into two parts: Part A and B. Part A was the double-blind, crossover, randomized, placebo-controlled trial. In Part A, patients were treated with 5 mg apraglutide or placebo once weekly for 4 weeks. After a washout period of 6-10 weeks, the alternate treatment was given. Part A was followed by a second washout period of 6-10 weeks before patients entered Part B. Part B was an open-label dosing regimen with 10 mg apraglutide given once weekly for 4 weeks. The additional open-label treatment period (Part B) was included to investigate the safety and tolerability of 10 mg dosing. The procedures during each treatment period were consistent. The trial drug was provided as a freeze-dried powder for reconstitution and was administered as subcutaneous injections in the abdominal area.

Procedures

Safety assessments were performed for each treatment period and included observation for injection site reactions, vital signs, blood samples, electrocardiogram (ECG), dipstick urinalysis, body weight and liver enzymes. They were performed at baseline, during each injection of the trial drug (pre-dose and at sequential time points), four days after first treatment injection, at the end of each treatment period, and 4-6 weeks after the last dosing at the end of the trial, as shown in Table 15. Additionally, liver enzymes were measured prior to each drug administration.

TABLE 15

| | Local tolerability | Vital signs | Blood samples | ECG | Dipstick urinalysis | Body weight |
|---|---|---|---|---|---|---|
| Baseline visit | | X | X | X | X | X |
| 1st administration of apraglutide | | | | | | |
| Pre-dose | | X | X | X | X | X |
| 0.5 h after administration | X | | | | | |
| 1 h after administration | X | X | | X | | |
| 2 h after administration | | X | X | | X | |
| 3 h after administration | X | | | | | |
| 4 h after administration | | X | | | | |
| 6 h after administration | | X | X | X | X | |
| 4 days after 1st administration of apraglutide | | X | X | X | X | X |
| 2nd administration of apraglutide | | | | | | |
| Pre-dose | | X | X | X | X | X |
| 0.5 h after administration | X | | | | | |
| 1 h after administration | X | | | | | |
| 3 h after administration | X | | | | | |
| 4 h after administration | | X | X | X | X | |
| End of treatment | | X | X | X | X | X |
| Safety follow up (4-6 weeks after last treatment at the end of the trial) | | X | X | X | X | X |

Efficacy assessments were performed for each treatment period of 29 days. Patients received a paper diary for recording PS volume administration, urine collections and oral fluid intakes at specific time points. Patients performed home 48-hour urine collections at baseline (day −2 to 1), immediately after first treatment injection (day 1 to 3), and at the end of the treatment period (day 27-29, 5 days after the fourth administration of the trial drug). Urine was collected by the patient in a urine container with volume markings and 48-hour urine volumes were reported in the diary. After completing the 48-hour collection, patients transferred approximately 100 mL of urine from the container to a sample which was delivered at the next patient visit. The amount of sodium excreted per 48 hours was then calculated as the concentration of sodium in the sample multiplied by the total volume of urine collected. During each urine collection, weekly PS volume and content and daily oral fluid intake were kept constant. Since they were kept constant, increases in urine volume were a sign of increased fluid absorption. Patients were informed to create a 24-hour drinking menu based on their habitual oral fluid intake at the baseline visit (day −3). Patients were to adhere to their drinking menu during each urine collection and the concomitant 48-hour oral fluid intake was reported in the diary during each urine collection.

On day 20-22, patients were informed to record their spontaneous oral fluid intake during 48 hours. This measurement was included to investigate whether increased intestinal absorption was associated with a decrease in their spontaneous oral fluid intake.

Between day 4 and 24, PS volume reductions were allowed if deemed clinically necessary by the investigator. Due to the relatively short treatment period of 4 weeks, PS volume was only reduced if patients had clinical signs of fluid retention (such as edema and excessive unintended weight gain). PS volume reductions were assessed during day 20-22. Patients returned to their baseline PS volume and content during the end of the treatment urine collection (day 27-29). Concomitant medications including proton-pump inhibitors, loperamide, and opiates were kept unchanged and stable throughout the trial. If necessary, adjustments could be made in the drinking menu and prescribed PS volume and content between treatment periods based on discussions between the patient and the investigator.

Body weight was measured using a levelled platform scale. Body composition was measured by dual-energy x-ray absorptiometry (Norland XR-36 DXA densitometer, Ford Atkinson, WI, USA) at baseline and at end of treatment.

Blood samples for analysis of plasma concentration of apraglutide and fasting plasma L-citrulline, a marker of enterocyte mass, were collected at baseline, during first and second treatment injection, four days after first treatment injection and at the end of treatment. A blood sample for fasting plasma L-citrulline was also collected 4-6 weeks after last dosing at the end of the trial. A blood sample for anti-apraglutide antibodies was collected at baseline, at the end of treatment and 4-6 weeks after last dosing at the end of the trial.

Analysis of Urine Sodium Concentration

Urine sodium was measured with COBAS 8000 modular analyzer series using an ion-specific electrode system (Roche Diagnostics, Indianapolis, IN) with the lower limit of quantification 10 mmol/liter. If urine sodium was below the lower limit of quantification, samples were analyzed by flame photometry.

Analysis of Apraglutide Plasma Concentration and L-Citrulline

Apraglutide and L-citrulline were quantified using a validated LC-MS-based method. For apraglutide, the analytical method used solid-phase extraction purification of the intact apraglutide molecule and its internal standard. The compounds were identified and quantified using reversed-phase HPLC with MS/MS detection using an AB Sciex API 5000 quadrupole mass spectrometer. For samples below the limit of quantification of 5.00 ng/mL, compounds were identified and quantified using reversed-phase UHPLC with MS/MS detection using an AB Sciex API 5500 quadrupole mass spectrometer. For L-citrulline, the analytical method used protein precipitation extraction of L-Citrulline and its internal standard. The compounds were identified and quantified using Hilic HPLC with MS/MS detection using an AB Sciex API 5000 quadrupole mass spectrometer.

Analysis of Anti-Apraglutide Antibodies

A fully validated ELISA method was used for the detection of anti-apraglutide antibodies in serum, following a three-tiered assay approach. In the first tier, anti-apraglutide antibodies present in samples and controls bonded to apraglutide immobilized on a microtiter plate. The bound anti-apraglutide antibodies were then detected with protein A/G and protein L. A sample with a signal above the validated screening cut-point was considered potentially positive and was then tested in the second tier, the confirmatory assay. For this, samples were pre-treated with an excess of apraglutide prior to testing them in the assay described above. An inhibition of the signal equal to or greater than the validated confirmatory cut-point confirmed the presence of antibodies. Samples were then reported as anti-apraglutide antibody positive. Titers were then determined by serial dilution of all confirmed positive samples.

Statistical Analysis

A crossover design was applied, where each patient served as their own control to eliminate between-subject variability and reduce the influence of confounding covariates.

Safety was assessed in all patients who had received at least one dose of trial drug (active or placebo). Efficacy was assessed following a modified intention-to-treat principle including all randomized patients with at least one valid post-baseline efficacy measurement (full analysis set).

Two different statistical analyses were performed: Part A only version and Part A+B total version. The Part A version was based on a 2×2 crossover design, whereas the Part A+B version assumed no period effect in order to estimate the contrasts between the three different treatments (placebo, 5 mg, and 10 mg). Both the Part A and Part A+B version of the statistical analysis were included in the results. The analysis of Part A was randomized and blinded. The analysis of Part A+B was included to make the comparison between placebo, 5 mg, and 10 mg. An analysis of covariance was used to assess the effects of apraglutide. The period-specific baseline measurement of the outcome variable, oral fluid intake, and PS volume were included in the analysis. All statistical tests were done using a two-sided test at a 5% significance level. Estimates were presented with approximate 95% confidence intervals and p-values. SAS version 9.4 was used for the analysis.

Example 6: Phase 2 Metabolic Balance Trial

The following non-limiting example describes results from a Phase 2 clinical trial in which subjects with short bowel syndrome intestinal failure and short bowel syndrome intestinal failure were treated with using the apraglutide formulations of the present disclosure. This Phase 2 trial investigated the safety and efficacy of the apraglutide formulations of the present disclosure.

Treatment with glucagon-like peptide-2 (GLP-2) analogs promotes intestinal adaptation in patients with short bowel syndrome (SBS). Apraglutide is a novel long-acting GLP-2 analog designed to enable once weekly dosing. This Phase 2 trial investigated the safety and efficacy of once weekly 5 mg apraglutide in patients with SBS intestinal failure (SBS-IF) and SBS intestinal insufficiency (SBS-II). In this open-label trial, 8 adult patients with SBS-IF (n=4) or SBS-II (n=4) and a fecal wet weight of ≥1500 g/day were treated with once weekly subcutaneous 5 mg apraglutide for 4 weeks. Safety was the primary endpoint. As secondary endpoints changes were examined from baseline in intestinal absorption of wet weight, energy (measured by bomb calorimetry) and electrolytes as well as fecal wet weight and urine production using 72-hour metabolic balance studies. Common treatment-related adverse events were consistent with the physiological effect of GLP-2 and included reduced stoma output (n=6), stoma complication (n=6), nausea (n=5), flatulence (n=4), polyuria (n=3) and abdominal pain (n=3). Once weekly apraglutide significantly increased energy, wet weight and electrolyte absorption, reduced fecal wet weight and increased urine production (Table 16).

TABLE 16

| | Estimated absolute mean change from baseline (95% CI and p-value, paired t-test) |
|---|---|
| Wet weight absorption (g/day) | 741 (194 to 1287; $p < 0.05$) |
| Energy absorption (kJ/day) | 1095 (196 to 1994; $p < 0.05$) |
| Fecal wet weight (g/day) | −680 (−1200 to −159; $p < 0.05$) |
| Urine production (g/day) | 560 (72 to 1048; $p < 0.05$) |
| Sodium absorption (mmol/day) | 38 (3 to 74; $p < 0.05$) |
| Potassium absorption (mmol/day) | 18 (4 to 32; $p < 0.05$) |

Results

Nine patients were screened. One patient did not fulfil the inclusion criteria of a fecal output ≥1,500 g/day and a urine volume <2,000 mL/day (assessed during the baseline metabolic balance study). Eight patients were dosed in the trial. All eight patients completed the trial and constituted the safety and full analysis set, as shown in FIG. 13. Demographics and baseline characteristics of the patients are summarized in Table 17. Data in Table 17 are mean (SD) or N (%) and parenteral support (PS) was scheduled PS at trial entry based on a weekly average.

TABLE 17

| | SBS-II (N = 4) | SBS-IF (N = 4) | Total (N = 8) |
|---|---|---|---|
| Age (years) | 64.5 (3.4) | 57.5 (20.0) | 61.0 (13.8) |
| Sex | | | |
| Female | 2 (50%) | 3 (75%) | 5 (62.5%) |
| Male | 2 (50%) | 1 (25%) | 3 (37.5%) |
| Weight at baseline | 83.2 (18.5) | 62.5 (11.2) | 72.8 (18.0) |
| Body-mass index (kg/m2) | 28.6 (5.1) | 22.7 (4.2) | 25.6 (5.4) |
| Race, white | 4 (100%) | 4 (100%) | 8 (100%) |
| Parenteral support volume (mL/day) | | 2,230 (889) | |
| Parenteral support energy (kJ/day) | | 2,823 (3,579) | |
| Urine production (g/day) | 1,423 (212) | 1,370 (284) | 1,397 (234) |
| Dietary intake (g/day) | 5,710 (1,519) | 3,255 (1,006) | 4,482 (1,773) |
| Fecal output (g/day) | 3,419 (2,015) | 3,243 (1,339) | 3,331 (1,587) |
| Cause of resection | | | |
| Crohn's disease | 3 (75%) | 0 | 3 (37.5%) |
| Mesenteric vascular disease | 1 (25%) | 1 (25%) | 2 (25%) |
| Surgical complications to ulcerative colitis | 0 | 3 (75%) | 3 (37.5%) |
| Disease characteristics | | | |
| Small bowel length (cm) | 180 (42) | 155 (125) | 168 (87) |
| End-jejunostomy | 2 (50%) | 2 (50%) | 4 (50%) |
| Ileostomy | 2 (50%) | 2 (50%) | 4 (50%) |
| Colon in continuity | 0 | 0 | 0 |
| Concomitant medication | | | |
| Proton-pump inhibitor | 4 (100%) | 3 (75%) | 7 (87.5%) |
| Opioids or opioid agonists | 3 (75%) | 3 (75%) | 6 (75%) |
| Loperamide | 2 (50%) | 1 (25%) | 3 (37.5%) |

Safety Results

All patients experienced at least one treatment related adverse event. The adverse events were mild to moderate. Common adverse events are summarized in Table 18 (data are N or N (%)). Adverse events that occurred in >2 patients and included decreased gastrointestinal stoma output (n=6), stoma complication (n=6), gastrointestinal stoma complication (n=5), nausea (n=5), abnormal gastrointestinal stoma output (n=4), flatulence (n=4), polyuria (n=3) and abdominal pain (n=3). One patient experienced transient injection site reactions (local erythema and pruritus) after one injection which was unrelated to the presence of anti-apraglutide antibodies. Three patients had previously received native GLP-2 or another GLP-2 analogue in a clinical trial (minimum of 16 months prior to trial inclusion). A total of three serious adverse events (SAE) occurred in two patients. One SAE, an event of abdominal pain requiring hospital admission, was assessed as related to the trial drug. The abdominal pain was conservatively treated, and the patient was discharged within less than 24 hours. A temporary discontinuation and re-challenge at a reduced dose allowed the patient to complete the trial. The remaining two SAEs were not considered related to apraglutide. They included one event of acute kidney injury due to dehydration in a patient with SBS-II and one event of a CRBSI in a patient with SBS-IF. Two additional patients required a dose reduction in order to complete the trial. One patient with SBS-II had signs of fluid retention after the first drug administration, and therefore the second and third administrations were given at reduced dose. The fourth/last administration was given at full dose (5 mg) without further complications. One patient experienced constipation after the first drug administration, and consequently, the second administration was given at reduced dose. The full dose was reintroduced for the third and fourth/last administration without further complications.

TABLE 18

| | SBS-II (N = 4) | SBS-IF (N = 4) | Total (N = 8) |
|---|---|---|---|
| Any adverse event | 4 | 4 | 8 (100%) |
| Gastrointestinal stoma output decreased | 3 | 3 | 6 (75%) |
| Stoma complication | 3 | 3 | 6 (75%) |
| Gastrointestinal stoma complication | 3 | 2 | 5 (62.5%) |
| Nausea | 1 | 4 | 5 (62.5%) |
| Gastrointestinal stoma output abnormal | 3 | 1 | 4 (50%) |
| Flatulence | 3 | 1 | 4 (50%) |
| Polyuria | 2 | 1 | 3 (37.5%) |

TABLE 18-continued

| | SBS-II (N = 4) | SBS-IF (N = 4) | Total (N = 8) |
|---|---|---|---|
| Abdominal pain | 1 | 2 | 3 (37.5%) |
| Weight increased | 2 | 0 | 2 (25%) |
| Fluid retention | 1 | 1 | 2 (25%) |

No safety concerns were raised from vital signs, blood samples, ECG, dipstick urinalysis or body weight. One patient with SBS-IF developed anti-apraglutide antibodies during the trial. The antibodies were negative after a 4-6 week washout. The patient had previously been treated with a GLP-2 analogue in a clinical trial setting in 2016. No effects of anti-apraglutide antibodies were detected on the pharmacokinetic profile, the pharmacodynamic response to apraglutide or on the number or duration of adverse events. None of the patients discontinued the trial due to adverse events and no deaths occurred.

Efficacy Endpoints

Wet Weight

The individual changes from baseline following treatment with apraglutide in the wet weight of the dietary intake, fecal output, urine and absorption are shown in FIG. 14. Apraglutide did not change the wet weight of dietary intake, as shown in Table 19. In Table 19, the data are shown as an adjusted mean (95% CI) and calculations are based on changes from baseline to end of treatment. Apraglutide s increased intestinal absorption of wet weight by 741 g/day (95% CI 194 to 1287; P=0.015), as shown in Table 19. Apraglutide significantly decreased fecal output by 680 g/day (95% CI−1200 to −159; P=0.018) and increased urine production by 560 g/day (95% CI 72 to 1048; P=0.030), as shown in Table 19.

Energy and Macronutrients

FIG. 16 shows the individual changes from baseline in the energy content of dietary intake, fecal output and absorption. Apraglutide did not change total dietary energy intake or any individual macronutrient, as shown in Table 19. Compared to baseline, apraglutide increased intestinal absorption of energy by 1,095 kJ/day (95% CI 196 to 1,994; P=0.024), as shown in Table 19. With a suggestion of improvements in energy absorption, the energy content of fecal output decreased by 941 kJ/day (95% CI−2,438 to 556 P=0.181), as shown in Table 19. Carbohydrate and lipid absorption significantly increased by 518 kJ/day (95% CI 112 to 924; P=0.019) and 376 kJ/day (95% CI 61 to 691; P=0.026) respectively, as shown in Table 19. Protein absorption increased by 104 kJ/day (95% CI−205 to 412; P=0.453), as shown in Table 19. The individual changes in macronutrient absorption are plotted in FIG. 17.

Body Weight and Body Composition

Body weight increased by 1.8 kg (95% CI 0.4 to 3.1; P=0.016) after four weeks of apraglutide treatment. Lean body mass significantly increased by 1.7 kg (95% CI 0.8 to 2.6; P=0.003) and fat mass decreased by 1.1 kg (95% CI−2.1 to −0.0; P=0.044). There was no significant change in bone mineral content which changed by −20 g (95% CI−58 to 19; P=0.268).

Citrulline

Compared to baseline, apraglutide increased absolute and relative plasma concentration of L-citrulline by 15.2 mol/L (95% CI 3.3 to 27.1; P=0.019) and 66% (95% CI 3 to 128; P=0.043), respectively.

Pharmacokinetics

The plasma concentration of apraglutide increased rapidly after dosing, with maximum mean concentration of 118.0 ng/mL reached after a mean of 29.5 hours. The mean elimination half-life was 27.0 hours and mean clearance was 0.9 L/h. W

TABLE 19

| | Dietary intake | Fecal output | Urine | Absorption |
|---|---|---|---|---|
| Wet weight (g/day) | 61 (−84.0 to 207); P = .352 | −680 (−1,200 to −159); P = .018 | 560 (72 to 1,048); P = .030 | 741 (194 to 1,287); P = .015 |
| Energy (kJ/day) | 154 (−1,006 to 1,314); P = .763 | −941 (−2,438 to 556); P = .181 | — | 1,095 (196 to 1,994); P = .024 |
| Carbohydrate (kJ/day) | 154 (−268 to 575); P = .418 | −365 (−772 to 43); P = .072 | — | 518 (112 to 924); P = .019 |
| Lipid (kJ/day) | 67 (−638 to 771); P = .830 | −309 (−969 to 351) P = .304 | — | 376 (61 to 691); P = .026 |
| Protein (kJ/day) | −41 (−274 to 191); P = .688 | −145 (−497 to 207); P = .362 | — | 104 (−205 to 412); P = .453 |
| Sodium (mmol/day) | −5 (−30 to 21); P = .680 | −43 (−92 to 6); P = .077 | 27 (5 to 49); P = .024 | 38 (3 to 74); P = .039 |
| Potassium (mmol/day) | 4 (−5 to 12); P = .337 | −15 (−32 to 3); P = .086 | 13 (6 to 20); P = .003 | 18 (4 to 32); P = .020 |
| Magnesium (mmol/day) | 1 (−2 to 3); P = .561 | 0 (−9 to 9); P = .961 | 1 (−1 to 2), P = .411 | 0 (−9 to 9); P = .930 |
| Calcium (mmol/day) | −2 (−5 to 2); P = .367 | −13 (−36 to 11); P = .255 | 0 (−1 to 1) P = .419 | 11 (−13 to 35); P = .313 |

Electrolytes

Apraglutide increased absorption of sodium and potassium by 38 mmol/day (95% CI 3 to 74; P=0.039) and 18 mmol/day (95% CI 4 to 32; P=0.020) respectively, as shown in Table 19. Urine sodium and potassium excretion increased by 27 mmol/day (5 to 49; P=0.024) and 13 mmol/day (95% CI 6 to 20; P=0.003) respectively, as shown in Table 19. There was no change in the absorption or urine excretion of magnesium and calcium, as shown in Table 19. The electrolyte content of dietary intake and fecal output did not change, as shown in Table 19. Individual changes from baseline in electrolyte absorption are shown in FIG. 15.

Summary of Example 6

The results described in Example 6 demonstrate that 5 mg apraglutide administered once weekly was safe and well tolerated in patients with SBS-II and SBS-IF after four weeks of treatment and showed positive effects on intestinal absorption, which in a clinical setting, would eliminate or reduce the need for PS.

Adverse events were consistent with the known physiological effects of GLP-2. Frequently reported related adverse events were of gastrointestinal origin, but they were generally mild and transient.

Apraglutide significantly increased intestinal absorption of wet weight, energy and electrolytes (sodium and potassium). The improvements in absorption were accompanied by a significant decrease in fecal wet weight and increase in urine production and urine electrolyte excretion (sodium and potassium). The changes in urine production found in this trial are considered clinically relevant as they could enable PS reductions or help regain enteral autonomy in patients with SBS-IF. It is envisioned that these improvements could eventually also reduce the risk of developing intermittent or chronic IF in patients with SBS-II and alleviate the symptom burden of malabsorption.

The pharmacokinetic profile of apraglutide supported a once weekly dosing regimen.

Apraglutide is the first GLP-2 analogue to improve absorption of energy across the whole patient spectrum in the SBS population when measured by bomb calorimetry, which is regarded as the gold standard laboratory method for quantifying intestinal energy absorption. For individual macronutrients, apraglutide increased absorption of carbohydrates and lipids, whereas protein absorption remained unchanged. As would be appreciated by the skilled artisan, in later stages of clinical development, weaning off PS with decreasing energy requirements is considered evidence of an improved energy absorption.

The PK profile of apraglutide allowed for consistent exposure which might explain the improved effects on energy absorption.

Apraglutide significantly increased body weight and lean body mass and reduced fat mass, which, as would be appreciated by the skilled artisan, indicates possible improvements in hydration status.

Apraglutide did not change the wet weight or energy content of dietary intake. Although oral fluid intake was fixed, the dietary intake of solids was unrestricted. GLP-2 did not significantly affect appetite or postprandial feeling of satiety in healthy humans. A reduced dietary intake could be an undesired side-effect in patients with SBS who depend on hyperphagia to compensate for the intestinal losses. Long-term GLP-2 treatment allowed patients to reduce their dietary intake while maintaining the same degree of absorption. Thus, it is envisioned that administration of apraglutide might alleviate the need for severe hyperphagia which is a predominant symptom in especially patients with severe SBS-II.

Apraglutide significantly increased plasma L-citrulline, a marker of enterocyte mass, providing support for its expected pro-adaptive effects. GLP-2 also inhibited gastrointestinal motility and reduced gastric acid secretion and thereby could increase exposure of the enterocyte to the luminal content. Mesenteric blood flow can also be stimulated by GLP-2, which could increase nutrient absorption. GLP-2 may also upregulate transport proteins as shown in animal studies.

The results described in Example 6 indicate that 5 mg apraglutide treatment administered weekly for four weeks is safe and well tolerated in patients with SBS-IF and SBS-II. These results demonstrate for the first time, a once weekly GLP-2 analog significantly improved absorption of wet weight, energy, electrolytes and increased urine production. Apraglutide only requires weekly injections which may reduce the injection burden and contribute to patient care and compliance. The reduced injection frequency may also increase patient acceptability and decrease the risk of injection site reactions.

Once weekly treatment with apraglutide increased intestinal absorption of fluid, electrolytes and energy. Without wishing to be bound by theory, these results indicate that the treatment of patients with the apraglutide compositions of the present disclosure can improve intestinal wet weight absorption and energy in a patient with SBS-IF, and therefore can be implemented in a therapeutic setting.

Methods

Trial Design and Participants

A total of nine adult patients (aged ≥18 to ≤80 years) with SBS were screened, eight of whom enrolled in the trial: four patients had SBS-II and four patients had SBS-IF. Both subgroups of patients were included to investigate the safety and efficacy of apraglutide across the disease spectrum. Patient eligibility was assessed during a screening visit. Main inclusion criteria were SBS secondary to surgical resection of the small intestine with or without colon; at least six months since last surgical bowel resection; and a severe degree of malabsorption, defined as a fecal wet weight output ≥1,500 g/day and a urine volume production <2000 mL/day. Fecal output and urine volume production were confirmed during baseline examinations. Patients were excluded if they had clinical signs of active inflammatory bowel disease, a history of cancer within five years or an inadequate hepatic-, kidney- or heart function. Patients were also excluded if they were pregnant or breastfeeding, had a positive HIV, hepatitis B or C test, had been hospitalized within one month before the screening visit or had received native GLP-2 or GLP-2 analogue within the last three months.

Procedures

Patients were treated with once weekly 5 mg apraglutide for four weeks. Apraglutide was provided as a freeze-dried powder for reconstitution in sterile water prior to injection, and treatments were administered as subcutaneous injections in the abdominal area. A 72-hour metabolic balance study was performed at baseline and at the end of the treatment period (starting one day after the fourth and last apraglutide injection). Each 72-hour metabolic balance study was performed during a five-day hospital admission. On the day of admission, patients were instructed to create a 24-hour drinking menu based on their habitual oral fluid intake. The drinking menu was to be followed during each balance study. On the second day of admission, just after the patients had urinated and emptied their stoma bags or defecated, the balance study was initiated. Patients were instructed to collect their fecal output, urine and a precise duplicate of their dietary intake (fluids and solids separated) in respective buckets which were replaced after 24 hours. Patients had free access to food but daily PS (volume and content) and oral fluid intake were kept constant during the baseline and post-treatment metabolic balance study periods. Daily PS and oral fluid intake were kept constant to ensure that the baseline and post-treatment measurements were comparable with regards to measuring the treatment effect. Daily PS and compliance to the predefined drinking menu was documented during admissions. Concomitant medications including proton pump inhibitors, loperamide and opiates remained unchanged throughout the trial.

The contents of the buckets were weighed, processed intro dry matter, and analyzed as previously described: energy by bomb calorimetry, nitrogen by Kjeldahl's method, lipid by a modified Van de Kamer titration technique, carbohydrate by Englyst's method, sodium and potassium by flame photometry and calcium and magnesium by atomic absorption spectrometry. A 24-hour average was calculated based on the three 24-hour periods. Absolute changes were calculated as the difference between the baseline and the post-treatment value. Relative changes were calculated as absolute changes divided by baseline values multiplied by 100.

Body weight was measured using a levelled platform scale. Body composition was measured by dual-energy x-ray absorptiometry (Norland XR-36 DXA densitometer, Norland, Ford Atkinson, WI, USA) at baseline and post-treatment.

First, second and fourth apraglutide injections were performed at the hospital. Safety assessments included observation for injection site reactions, vital signs, blood samples, electrocardiogram (ECG), urinalysis and body weight. They were performed at baseline, during each injection of the trial drug, four days after first injection, at the end of treatment and 4-6 weeks after last dosing at the end of the trial, as shown in Table 20. Liver enzymes were measured prior to each drug administration.

TABLE 20

| | Local tolerability | Vital signs | Blood samples | ECG | Dipstick urinalysis | Body weight |
|---|---|---|---|---|---|---|
| Baseline visit | | | X | X | X | X |
| 1st administration of apraglutide | | | | | | |
| Pre-dose | | X | X | X | X | X |
| 0.5 h after administration | X | | | | | |
| 1 h after administration | X | X | | X | | |
| 2 h after administration | | | X | | X | |
| 3 h after administration | X | | | | | |
| 4 h after administration | | X | | | | |
| 6 h after administration | | | X | X | X | |
| 4 days after 1st administration of apraglutide | | | | X | X | X |
| 2nd administration of apraglutide | | | | | | |
| Pre-dose | | | X | X | X | X |
| 0.5 h after administration | X | | | | | |
| 1 h after administration | X | | | | | |
| 2 h after administration | X | | | | | |
| 3 h after administration | | X | X | X | X | |
| 4 h after administration | | | | | | |
| 4th administration of apraglutide | | | | | | |
| Pre-dose | | X | | X | | X |
| 0.5 h after administration | X | | | | | |
| 1 h after administration | X | | | | | |
| 3 h after administration | X | | | | | |
| End of treatment | | | X | | X | X |
| Safety follow up (4-6 weeks after last treatment at the end of the trial) | | | X | X | X | X |

Blood samples for analysis of the plasma concentration of apraglutide and plasma concentration of fasting L-citrulline, a marker of enterocyte mass, were collected at baseline, during first and second injection (pre-dose and at sequential timepoints), four days after first injection and at the end of treatment. Blood sampling for apraglutide pharmacokinetics was also performed after the fourth and last injection covering 96 hours. A blood sample for fasting plasma L-citrulline was also collected 4-6 weeks after last dosing at the end of the trial. Blood samples for anti-apraglutide antibodies were collected at baseline, at the end of treatment and at the 4-6 weeks follow-up visit. All eight patients tested negative for anti-apraglutide antibodies at baseline.

Outcomes

The primary endpoint of this trial was safety. Secondary endpoints were absolute and relative changes from baseline in dietary intake, fecal excretion and absorption of wet weight, energy, macronutrients and electrolytes, urine production, urine electrolyte excretion, body weight, body composition, bone mineral content, plasma L-citrulline as well as pharmacokinetic profiles. Only absolute changes were presented in the scope of this disclosure with the exception of changes from baseline in plasma L-citrulline.

Analysis of Plasma Concentration of Apraglutide and L-Citrulline

Apraglutide and L-citrulline were quantified using a validated LC-MS-based method. For a apraglutide, the analytical method used solid-phase extraction purification of the intact apraglutide molecule and its internal standard. The compounds were identified and quantified using reversed-phase HPLC with MS/MS detection using an AB Sciex API 5000 quadrupole mass spectrometer. For samples below the limit of quantification of 5.00 ng/mL, compounds were identified and quantified using reversed-phase UHPLC with MS/MS detection using an AB Sciex API 5500 quadrupole mass spectrometer. For L-citrulline, the analytical method used protein precipitation extraction of L-citrulline and its internal standard. The compounds were identified and quantified using Hilic HPLC with MS/MS detection using an AB Sciex API 5000 quadrupole mass spectrometer.

Analysis of Anti-Apraglutide Antibodies

A fully validated ELISA method was used for the detection of anti-apraglutide antibodies in serum, following a three-tiered assay approach. In the first tier, anti-apraglutide antibodies present in samples and controls bonded to apraglutide immobilized on a microtiter plate. The bound anti-apraglutide antibodies were then detected with protein A/G and protein L. A sample with a signal above the validated screening cut-point was considered potentially positive and was then tested in the second tier, the confirmatory assay. For this, samples were pre-treated with an excess of apraglutide prior to testing them in the assay described above. An inhibition of the signal equal to or greater than the validated confirmatory cut-point confirmed the presence of antibodies. Samples were then reported as anti-apraglutide antibody positive. Titers were then determined by serial dilution of all confirmed positive samples.

Statistical Analysis

A statistical test of adjusted mean change from baseline to end of treatment was analyzed using a paired t-test. All statistical tests were done using a two-sided test at a 5% significance level. Estimates were presented with approximate 95% confidence intervals and p-values. SAS version 9.4 was used for the analysis.

Example 7: Pharmacokinetic/Pharmacodynamic Evaluation

Demographics and Other Baseline Characteristics 11 females and 13 males were included in the study. The demographic and baseline data are summarized in Table 21. No relevant medical history was reported. The most frequent reported prior concomitant medication was regarding birth control. Following first dosing, the most frequent reported concomitant medication was paracetamol. No relevant differences in concomitant medications were noted between the treatment groups.

TABLE 21

| | 1 mg apraglutide (N = 6) | 5 mg apraglutide (N = 6) | 10 mg apraglutide (N = 6) | Placebo (N = 6) | Total (N = 24) |
|---|---|---|---|---|---|
| Number of female/ male subjects | 3/3 | 3/3 | 2/4 | 3/3 | 11/13 |
| Age in years (mean ± SD) | 26.7 ± 6.3 | 24.5 ± 4.0 | 27.7 ± 7.8 | 29.2 ± 7.5 | 27.0 ± 6.4 |
| Height in cm (mean ± SD) | 178.02 ± 8.11 | 178.52 ± 11.39 | 175.48 ± 8.29 | 175.67 ± 11.19 | 176.92 ± 9.31 |
| Weight in kg (mean ± SD) | 75.683 ± 12.544 | 67.550 ± 11.070 | 72.150 ± 14.237 | 71.233 ± 12.382 | 71.654 ± 12.123 |
| BMI in kg/$m^2$ (mean ± SD) | 23.72 ± 2.02 | 21.13 ± 2.41 | 23.22 ± 2.22 | 22.98 ± 2.30 | 22.76 ± 2.32 |
| Number of American Indian or Alaska Native/ Asian/Mixed / White subjects | 0/0/1/5 | 1/1/0/4 | 0/1/0/5 | 0/0/0/6 | 1/2/1/20 |

BMI = body mass index;
SD = standard deviation. Measurements of Treatment Compliance Measurements of Treatment Compliance Treatments were subcutaneously (SC) administered to the subjects by members of clinical staff, there was full treatment compliance.

Pharmacodynamic and Efficacy Results

The plasma citrulline concentrations against time after first dose of apraglutide per dose level are presented in FIG. 18. The corresponding least square (LS) mean plot for change from baseline is provided in FIG. 19. Summary pharmacokinetic parameters of citrulline are provided in Table 22.

The endogenous marker citrulline was selected to assess the pharmacodynamic effect of apraglutide. Citrulline was detected in all baseline and post-dose samples. Three baseline citrulline samples were obtained during two baseline visits between screening and the first dosing day and before dosing on the first dosing day. Thirteen out of 24 subjects had a difference of <0.5 μg/mL over the three baseline samples with the smallest difference being 0.061 μg/mL observed for a 10 mg dosed subject. Another five and four subjects had a difference between 0.5-1 and 1-2 μg/mL across baseline assessments, respectively. The remaining two subjects had a difference >2 μg/mL with the largest difference being 2.762 μg/mL observed for a 1 mg dosed subject. At baseline, the mean citrulline range was 5.3825-5.6207 μg/mL for placebo, 5.3900-6.2028 μg/mL for 1 mg apraglutide, 4.8983-5.3023 μg/mL for 5 mg apraglutide and 5.0730-5.4690 μg/mL for 10 mg apraglutide. In the placebo group, the mean citrulline concentration remained relatively stable over the trial, ranging from 4.9735 to 5.8253 μg/mL.

Following the first weekly SC dose of apraglutide, citrulline was increased dose-dependently with the highest citrulline levels measured after four or seven days, with the exception of one subject in the 1 mg group whose maximum citrulline concentration was reached after two days. The highest mean citrulline value was 6.3920 μg/mL (after four days), 7.1933 g/mL (after four days) and 7.8487 μg/mL (after 7 days), for 1, 5 and 10 mg, respectively, while for placebo it was 5.8325 μg/mL (after one day).

The concentration at the end of each dosing interval, $R_{pre\text{-}dose}$, was assessed for each dose and showed that in general, citrulline levels were similar over the whole treatment period (Table 22).

Following the sixth and last weekly SC dose of apraglutide, an increase was observed at all dose levels and, in particular, for the highest doses. The mean $R_{max}$ was 7.1702, 8.1577 and 8.7254 μg/mL reached at 2.0, 3.9 and 3.9 days following the last dose of 1, 5 and 10 mg, respectively (Table 22). The corresponding placebo level was 6.3707 μg/mL at 16.9 days following the last dose. These $R_{max}$ values were only slightly lower than the mean $R_{max}$ assessed over the whole trial, with differences ranging from 0.0362, 0.0973 and 0.1016 μg/mL for 10, 5 and 1 mg, respectively. For placebo, the difference was 0.2586 μg/mL. The mean $R_{max}$ occurred around the same time for all apraglutide groups, ranging from 35.9 to 38.9 days following the first dose of 1 and 5 mg, respectively, while placebo peaked at 50.4 days following the first dose.

The mean citrulline increase observed following the last dose appeared to decline more rapidly for the lowest doses compared to 10 mg. Citrulline was assessed up to day 77. The lowest mean citrulline level following the last dose was reached 17 days later for both 1 and 10 mg. For 5 mg the lowest mean citrulline level was reached after an additional week. $Rt_{1/2}$ was assessed for two subjects, both dosed with 10 mg, and was 6.5 and 11.0 days (Table 22).

TABLE 22

| Last dose | Placebo | Apraglutide dose level 1 mg | 5 mg | 10 mg |
|---|---|---|---|---|
| | Arithmetic mean ± standard deviation | | | |
| 1 $R_{pre-dose}$ (μg/mL) | 5.2028 ± 1.1888 | 5.8075 ± 1.3328 | 6.7695 ± 1.5288 | 7.8487 ± 2.7273 |
| 2 $R_{pre-dose}$ (μg/mL) | 5.1740 ± 1.0442 | 6.2605 ± 1.2331 | 7.0082 ± 1.1330 | 7.6058 ± 2.3210 |
| 3 $R_{pre-dose}$ (μg/mL) | 4.9735 ± 1.3734 | 6.4913 ± 1.8297 | 6.6155 ± 1.2790 | 7.5180 ± 2.1369 |
| 4 $R_{pre-dose}$ (μg/mL) | 5.4545 ± 0.8906 | 6.0050 ± 1.5790 | 6.6227 ± 1.2247 | 7.2060 ± 2.5488* |
| 5 $R_{pre-dose}$ (μg/mL) | 5.4278 ± 1.3130 | 6.4128 ± 1.8032 | 6.8307 ± 1.2369 | 7.1994 ± 2.5111* |
| 6 $R_{max}$ (μg/mL) | 6.3707 ± 1.6653 | 7.1702 ± 1.6611 | 8.1577 ± 1.7108 | 8.7254 ± 3.0145* |
| $R_{pre-dose}$ (μg/mL) | 5.2883 ± 1.5281 | 6.3120 ± 1.6694 | 7.2498 ± 1.2461 | 8.0714 ± 3.0514* |
| NA $R_{max}$ (μg/mL) | 6.6293 ± 1.4010 | 7.2718 ± 1.6959 | 8.2550 ± 1.7807 | 8.7616 ± 2.9900* |
| | Median (minimum, maximum) | | | |
| 6 $Rt_{max}$ (d) | 16.9 (0.9, 41.9) | 2.0 (0.0, 34.9) | 3.9 (0.0, 6.9) | 3.9 (1.9, 7.0)* |
| $Rt_{1/2}$(d) | ND | ND | ND | 8.8 (6.5, 11.0)** |
| NA $Rt_{max}$ (d) | 50.4 (0.9, 77.0) | 35.9 (0.0, 70.0) | 38.9 (4.0, 41.9) | 36.9 (7.0, 39.0)* |
| | Geometric mean (geometric coefficient of variation %) | | | |
| 1 $R_{pre-dose}$ (μg/mL) | 5.0803 (24.9) | 5.6723 (24.6) | 6.5967 (26.7) | 7.4048 (40.7) |
| 2 $R_{pre-dose}$ (μg/mL) | 5.0802 (21.7) | 6.1526 (21.0) | 6.9208 (18.1) | 7.2438 (37.6) |
| 3 $R_{pre-dose}$ (μg/mL) | 4.8114 (29.1) | 6.2752 (29.2) | 6.5109 (19.9) | 7.2331 (32.4) |
| 4 $R_{pre-dose}$ (μg/mL) | 5.3963 (16.0) | 5.8213 (28.4) | 6.5313 (18.3) | 6.8103 (40.3)* |
| 5 $R_{pre-dose}$ (μg/mL) | 5.2867 (26.1) | 6.2097 (28.2) | 6.7248 (20.3) | 6.7908 (41.8)* |
| 6 $R_{max}$ (μg/mL) | 6.1904 (26.7) | 7.0069 (24.0) | 8.0024 (22.0) | 8.2533 (40.4)* |
| $R_{pre-dose}$ (μg/mL) | 5.0890 (31.9) | 6.1166 (28.5) | 7.1475 (19.3) | 7.5618 (44.0)* |
| NA $R_{max}$ (μg/mL) | 6.5079 (21.3) | 7.1036 (24.2) | 8.0870 (22.9) | 8.2953 (40.1)* |

NA = not applicable, assessed over the whole trial period;
ND = no data available;
$R_{max}$ = maximum response
$R_{Pre-dose}$ = response immediately prior to dosing;
$Rt_{max}$ = time to reach maximum response;
Rt½ = response half-life. Number of subjects (N) was 6 unless indicated otherwise.
*1 subject missing (N = 5) and**4 subjects missing (N = 2).

The variability across $R_{pre-dose}$ and $R_{max}$ (both following the last dose and throughout the trial) expressed as coefficient of variation (% CV) ranged for placebo from 16.0 to 31.9% (Table 22). This was in line with the % CV range observed for 1 and 5 mg of 18.1 to 29.2%. The % CV for 10 mg was slightly higher, 32.4 to 44.0%.

A statistical steady-state analysis per dose level was performed using Helmert's approach. In short, the first contrast tested compared the mean $R_{pre-dose}$ at the first time point (week 1) to the pooled mean $R_{pre-dose}$ over all remaining time points (week 2 to 6). The second contrast compared the mean at week 2 to the pooled mean over week 3 to 6, etc. Testing continued until the contrast was not statistically significant. The mean $R_{pre-dose}$ at week 6 for 10 mg against mean $R_{pre-dose}$ over week 5 (0.8720, 95% CI: 0.1590; 1.5850 and p=0.0172) was statistically significant. Visual inspection of the data suggests that steady state concentrations were reached following the first dosing at all investigated dose levels.

The citrulline data were analyzed using a mixed model analysis of variance. A summary of the analysis results is provided in Table 23. The statistical analysis clearly showed a significant overall treatment effect of apraglutide on citrulline (p=0.0007). All dose groups showed an increase compared to placebo, although the difference between placebo and 1 mg was not statistically significant. The increase compared to placebo became more pronounced and significant with increasing dose, namely an increase of 1.2574 μg/mL for the 5 mg dose (p=0.0025) and 1.6343 μg/mL for 10 mg (p=0.0002) (Table 23). In addition, when comparing the dose levels to each other, the 5 and 10 mg doses induced significantly higher citrulline levels compared to the 1 mg dose (0.9429 μg/mL higher [p=0.0186] and 1.3198 μg/mL higher [p=0.0018], respectively). The difference between the 5 and 10 mg doses was not statistically significant, although the effect following 10 mg appeared to be slightly higher than after 5 mg.

TABLE 23

| Parameter | Treatment p-value | Placebo-1 mg | Placebo-5 mg | Placebo-10 mg | 1 mg-5 mg | 1 mg-10 mg | 5 mg-10 mg |
|---|---|---|---|---|---|---|---|
| Citrulline (μg/mL) | 0.0007 | 0.3146 (−0.4371, 1.0663) P = 0.3910 | 1.2574 (0.5037, 2.0112) P = 0.0025 | 1.6343 (0.8809, 2.3878) P = 0.0002 | 0.9429 (0.1768, 1.7089) P = 0.0186 | 1.3198 (0.5586, 2.0810) P = 0.0018 | 0.3769 (−0.3766, 1.1304) P = 0.3078 |

TABLE 23-continued

| Parameter | Treatment p-value | Placebo-1 mg | Placebo-5 mg | Placebo-10 mg | 1 mg-5 mg | 1 mg-10 mg | 5 mg-10 mg |
|---|---|---|---|---|---|---|---|
| Bristol stool scale | 0.0189 | −0.9 (−1.6, −.3) P = 0.0092 | −1.0 (−1.7, −.4) P = 0.0046 | −0.6 (−1.3, 0.1) P = 0.0961 | −0.1 (−0.8, 0.6) P = 0.7531 | 0.3 (−0.3, 1.0) P = 0.3020 | 0.5 (−0.2, 1.1) P = 0.1928 |
| Bristol stool scale with zeroes set to missing | 0.3031 | −0.6 (−1.3, 0.1) P = 0.0808 | −0.4 (−1.1, 0.3) P = 0.2018 | −0.5 (−1.2, 0.2) P = 0.1648 | 0.2 (−0.5, 0.9) P = 0.6208 | 0.1 (−0.6, 0.8) P = 0.7282 | −0.0 (−0.8, 0.7) P = 0.8876 |
| Weight (kg) | 0.7104 | −0.750 (−2.497, 0.997) P = 0.3800 | −0.865 (−2.598, 0.868) P = 0.3092 | −0.331 (−2.065, 1.402) P = 0.6941 | −0.115 (−1.896, 1.666) P = 0.8939 | 0.419 (−1.324, 2.162) P = 0.6210 | 0.534 (−1.215, 2.283) P = 0.5309 |

The overall treatment p-value (all dose groups compared to placebo) and subsequent treatment group comparisons are shown. Estimates of the difference with 95% confidence intervals and p-values are shown per comparison.

Besides citrulline, the Bristol stool scale and body weight were assessed as pharmacodynamic endpoints. In contrast to citrulline and weight, the Bristol stool scale is a discrete variable. Subjects assessed their stool in the past 24 hours using the Bristol stool scale ranging from constipation (type 1) to diarrhea (type 7). No stool in the past 24 hours was recorded as zero. As two subjects (assigned to either 1 or 5 mg) reported no stool preceding the first dose, the screening Bristol stool scale score was also taken into account when determining the baseline Bristol stool scale score.

A significant overall treatment effect of apraglutide on the Bristol stool scale was observed, with a p-value of 0.0189 (Table 23). The specific placebo versus dose level contrasts showed a significant decrease in the 1 and 5 mg groups compared to placebo (−0.9, p=0.0092 and −1.0, p=0.0046); the decrease in the 10 mg group compared to placebo was not statistically significant. This pattern appeared to be driven by a few subjects who occasionally reported no stool. Following the first dose, assessment of the Bristol stool scale was scheduled at 11 visits and at trial discharge. Of these visits, no stool in the past 24 hours was reported 6 times (2 subjects), 13 times (4 subjects) and 1 time (1 subject) in the 1 mg, 5 mg, 10 mg group, respectively. In the placebo group, all subjects reported stool in the past 24 hours at each visit. No stool was reported 9 times during the 6 dosing weeks and 11 times in the subsequent 6 weeks, indicating no association with dosing.

Considering the potential impact of scoring no stool as 0 when a subject may not have normally defecated every 24 hours (supported by the observation that 2 out of 24 subjects reported 0 prior to the first dose), the analysis was repeated as a sensitivity analysis with no stool set to missing. With this adjusted analysis, no significant treatment effect was found either overall or for any of the specific treatment contrasts (Table 23).

Body weight appeared to be rather constant over the whole trial period, with no statistically significant treatment effect of apraglutide on body weight overall or for any of the specific treatment contrasts (Table 23). When considering individual body weight values, placebo subject 1007 showed a weight increase from 92.90 kg at screening to 99.30 kg at trial discharge visit.

Citrulline, BSS and weight data are analyzed with a mixed model analysis of variance with fixed factors treatment, time and treatment by time, random factor subject, and the average prevalue as covariate. The average pre-value was calculated from all pre-values after screening and before dosing, except for BSS, where the screening value was also used to calculate the average baseline.

MCP-MOD Analysis

The MCP-MOD procedure was applied. This statistical methodology consisted of 2 steps: the multiple comparisons step and the modelling step. The first step of the procedure (MCP) is used to test for a significant dose response by assessing pre-specified candidate models. Once a dose response has been established, the second step (MOD) is used to estimate a dose-response curve and estimation of target doses of interest. Five candidate models were specified:

- Linear model with maximum effect for the 10 mg dose
- Log-linear model with maximum effect for the 10 mg dose
- Dose that induces maximum effect ($E_{max}$) model with $ED_{50}$ of 5 mg
- Sigmoidal $E_{max}$ model with $ED_{50}$ of 1 mg and hill coefficient (HILL) of 2
- Sigmoidal $E_{max}$ model with $ED_{50}$ of 5 mg and HILL of 5

The results of the MCP step showed that all 5 candidate dose response models generated significant contrasts with a p-value of <0.0001 (Table 24). The estimates of the differences were slightly distinctive and resulted in a set of models with a better fit and a set with slightly worse fit. The candidate dose response models yielding the largest estimate of the difference were the 1) $E_{max}$ model with $ED_{50}$=5 mg, 2) log-linear model and 3) sigmoidal $E_{max}$ model with $ED_{50}$ of 1 mg and HILL of 2 (Table 24). As these estimates of the difference were very similar, all 3 models were taken into the MOD part. The models are referred to as 1) $E_{max}$, 2) LogLin and 3) Sigmoid $E_{max}$ model, respectively.

TABLE 24

| Candidate dose response model | Test statistic | p-value | Estimate of the difference | 95% CI Lower | 95% CI Upper |
|---|---|---|---|---|---|
| Linear | 5.704 | <0.0001 | 2.0781 | 1.3127 | 2.8435 |
| Log-linear | 6.168 | <0.0001 | 2.2125 | 1.4588 | 2.9661 |
| $E_{max}$ with $ED_{50}$ = 5 mg | 6.172 | <0.0001 | 2.2150 | 1.4610 | 2.9689 |
| Sigmoid $E_{max}$ with $ED_{50}$ = 1 mg and H = 2 | 6.144 | <0.0001 | 2.1663 | 1.4256 | 2.9071 |
| Sigmoid $E_{max}$ with $ED_{50}$ = 5 mg and H = 5 | 5.687 | <0.0001 | 2.0713 | 1.3061 | 2.8365 |

CI = confidence interval;
$ED_{50}$ = dose that induces 50% of maximum effect;
$E_{max}$ = maximum effect;
H = hill coefficient;
MCP-MOD = multiple comparison procedure-modelling. Doses comprised of 0 (placebo), 1, 5 and 10 mg apraglutide. Citrulline response data comprised the average baseline value and day 35 to 42 (= week 6) data. Per the candidate dose response model, the analysis result is characterized by test statistic, p-value of the contrast and estimate of the difference with 95% CI.

A subset of the citrulline data was made with the average pre-value and day 35 to 42=week 6 data. The coefficients were implemented in the mixed model analysis of variance with fixed factors treatment, time and treatment by time, random factor subject, and the average prevalue as covariate. The average pre-value was calculated from all pre-values after screening and before dosing.

The following contrasts are calculated within the model:

Linear with coefficients −0.508−0.381 0.127 0.762

LinLog with coefficients −0.654−0.283 0.306 0.631

Emax with coefficients −0.632−0.316 0.316 0.632

Sigmoid Emax Hill=2 ED50=1 with coefficients −0.759−0.140 0.432 0.467

Sigmoid Emax Hill=5 ED50=5 with coefficients −0.456−0.455 0.164 0.747

The MOD step showed that the predicted citrulline change from placebo for a dose of 1, 5 and 10 mg were rather similar for all 3 models (Table 25). With a dose of 1 mg, the predicted placebo and baseline corrected change in citrulline across the 3 models ranged from 0.7125 to 0.8712 μg/mL with significant results for the $E_{max}$ (p=0.0184) and Log-linear (p=0.0238) models. For the Sigmoid $E_{max}$ model, the p-value was 0.0645. When increasing the dose to 5 mg, the predicted change from placebo increased to a range of 2.1652 to 2.3327 μg/mL. For a dose of 10 mg, the predicted change from placebo was slightly higher and ranged from 2.6946 to 2.8604 μg/mL. The predicted response versus placebo for both 5 and 10 mg was statistically significant for all models, with a p-value of <0.0001.

The apraglutide dose levels required for a baseline and placebo corrected citrulline increase of 1, 2 and 3 μg/mL were predicted (Table 25). The $E_{max}$ of the Sigmoid $E_{max}$ model was <3 μg/mL, so for this model a change of 2.5 μg/mL was chosen as largest response. The predicted apraglutide dose for a citrulline increase of 1 μg/mL was 1.2333 mg, 1.2249 mg and 1.3606 mg, for the $E_{max}$, LogLin and Sigmoid $E_{max}$ model, respectively. To evoke a citrulline increase of 2 μg/mL, the predicted apraglutide doses were 3.8471 mg, 4.2011 mg and 3.4042 mg for the $E_{max}$, LogLin and Sigmoid $E_{max}$ model, respectively. Finally, the predicted apraglutide doses for change from placebo of 2.5 or 3 μg/mL were 13.1053 mg, 11.4325 mg and 6.4619 mg using the $E_{max}$, LogLin and Sigmoid $E_{max}$ model, respectively. It should be noted that the uncertainty in the predicted apraglutide doses is rather large, especially to achieve an effect of 2.5 or 3 μg/mL.

TABLE 25

| Prediction | $E_{max}$ | Log-linear | Sigmoid $E_{max}$ |
|---|---|---|---|
| Predicted change from placebo effect for dose of 1 mg | 0.8535 (0.11584, 1.5486) p = 0.0184 | 0.8712 (0.1273, 1.6151) p = 0.0238 | 0.7125 (−0.0466, 11.4716) p = 0.0645 |
| Predicted change from placebo effect for dose of 5 mg | 2.2442 (1.4239, 3.0644) p = <0.0001 | 2.1652 (1.3805, 2.9499) p = <0.0001 | 2.3327 (1.5737, 3.0916) p = <0.0001 |
| Predicted change from placebo effect for dose of 10 mg | 2.8182 (1.9820, 3.6544) p = <0.0001 | 2.8604 (2.0011, 3.7197) p = <0.0001 | 2.6946 (1.8761, 3.5131) p = <0.0001 |
| Predicted dose for change from placebo of 1 μg/mL | 1.2333 (−0.04246, 2.5091) p = 0.0574 | 1.2249 (−0.2169, 2.6667) p = 0.0920 | 1.3606 (0.2680, 2.4532) p = 0.0170 |
| Predicted dose for change from placebo of 2 μg/mL | 3.8471 (0.3534, 7.3409) p = 0.0324 | 4.2011 (0.6406, 7.7617) p = 0.0229 | 3.4042 (−0.1290, 6.9374) p = 0.0582 |
| Predicted dose for change from placebo of 2.5 μg/mL* | ND | ND | 6.4619 (−0.5521, 13.4759) p = 0.0692 |
| Predicted dose for change from placebo of 3 μg/mL* | 13.1053 (−6.3068, 32.5173) p = 0.1754 | 11.4325 (1.5808, 21.2843) p = 0.0249 | ND |

CI = confidence interval;
$E_{max}$ = maximum effect;
ND = not determined.
*The Emax of the Sigmoid Emax model was <3 μg/mL, therefore the largest response was set at 2.5 μg/mL. Predictions were made based on doses of 0 (placebo), 1, 5 and 10 mg apraglutide and citrulline response data comprised of the average baseline value and day 35 to 42 (=week 6) data. Estimated change/dose with 95% CIs and p-values are shown per prediction.

Adjustments for Covariates

For all pharmacodynamic endpoints (citrulline, Bristol stool scale and weight), the pre-value has been used as covariate. The average pre-value was calculated from all pre-values after screening and before dosing, except for the Bristol stool scale, where the screening value was also used to calculate the average baseline. The average pre-value of citrulline was also used as covariate in the MCP-MOD, except in the Sigmoid $E_{max}$ model. This was addressed by subtracting the pre-value times the slope of the linear model of the MCP part from the values of week 6.

Drug Dose, Drug Concentration, and Relationships to Response

The plasma apraglutide concentration against time after the first dose of apraglutide by dose level is presented in FIG. 20A-FIG. 20B. Summary pharmacokinetic parameters of apraglutide are provided in Table 26.

The mean apparent total clearance (CL/F) appeared to be constant across the 3 dose levels and ranged from 16.480 (5 mg) to 20.747 L/d (10 mg) (Table 26). The mean apparent volume of distribution during the terminal elimination phase ($V_z$/F) after the last dosing appeared to be dose dependent with values of 55.426 and 105.021 L for 5 and 10 mg, respectively. Insufficient data points were available to determine $V_z$/F for the 1 mg dose group (an insufficient number of samples were above the lower limit of quantification during the sampling period following the last dosing).

Following the first weekly SC dose of apraglutide, plasma apraglutide concentrations increased with no apparent lag time in all subjects (except for subject 1002 on 1 mg who had no detectable concentrations up to the next dose). The $C_{max}$ was reached at day 1 by four, four and one subject on 1 mg, 5 mg and 10 mg apraglutide, respectively (FIG. 20). The remaining subjects reached $C_{max}$ at day 2. Subjects on 1 mg declined below the limit of quantification (LOQ) at day 4 or 7 while subjects on 5 and 10 mg remained above the LOQ up to the next dose. The exposure following the first dose was dose-dependent with a mean $C_{max}$ of 13.918±11.2, 94.088±50.5 and 136.855±55.0 ng/mL for the 1, 5 and 10 mg dose groups, respectively, and $AUC_{tau}$ values of 35.214, 300.269 and 476.937 d*ng/mL, respectively (Table 26). The half life (h) measured following dose #6 in the 5 mg dose group was measured as 72.7±23.0 and the half life measured following dose #6 in the 10 mg dose group was measured as 76.3±27.6.

At $C_{trough}$ of the next 5 doses, 5 subjects (all dosed with 1 mg) had one or multiple samples that were undetectable for apraglutide. All other subjects showed measurable apraglutide concentrations. The mean $C_{trough}$ over the 6 doses ranged from 0.000 (week 1) to 0.873 ng/mL (week 4) for 1 mg apraglutide, from 7.605 (week 5) to 10.163 ng/mL (week 4) for 5 mg apraglutide and from 13.710 (week 6) to 18.460 ng/mL (week 2) for 10 mg apraglutide (Table 26).

Following the sixth and last weekly SC dose of apraglutide, all subjects (subject 3004 was excluded because of dosing discontinuation) showed increased apraglutide concentrations with no apparent lag time. Subjects reached $C_{max}$ 1 day following the last dose, except for 2 and 3 subjects on 5 and 10 mg, respectively, who reached $C_{max}$ after 2 days. Pharmacokinetic parameters were assessed up to 2 weeks following the last dose. All subjects on 1 mg and 1 subject on 5 mg had unquantifiable concentrations in the last 2 or 3 samples. The remaining subjects, including all subjects on 10 mg, had still quantifiable concentrations up to 4.46 ng/mL in the last pharmacokinetic sample.

TABLE 26

| | Parameter | | | | | |
|---|---|---|---|---|---|---|
| | 1 mg apraglutide | | 5 mg apraglutide | | 10 mg apraglutide | |
| Last dose | #1-5 | #6 | #1-5 | #6 | #1-5 | #6 |
| Arithmetic mean ± standard deviation | | | | | | |
| $C_{max}$ (ng/mL) | 13.918 ± 11.236 | 24.238 ± 9.225 | 94.088 ± 50.467 | 124.818 ± 72.126 | 136.855 ± 55.403 | 182.374 ± 97.626 |
| $1^{st}/6^{th}$ $C_{trough}$ (ng/ML) | 0.000 ± 0.000 | 0.678 ± 0.799 | 7.912 ± 3.548 | 7.623 ± 3.367 | 14.543 ± 5.476 | 13.710 ± 4.806 |
| $AUC_{tau}$ (d*ng/mL) | 35.214 ± ±7.387 | 59.437 ± 14.060 | 300.269 ± 121.212 | 357.651 ± 153.604 | 476.937 ± 208.314 | 582.409 ± 284.359 |
| $AUC_{tau}$/dose (d*ng/mL/μg) | 0.03426 ± 0.02069 | 0.05944 ± 0.01406 | 0.05860 ± 0.02505 | 0.07153 ± 0.03072 | 0.04679 ± 0.02177 | 0.05824 ± 0.02844 |
| $C_{max}$/dose (ng/mL/μg) | 0.01351 ± 0.01087 | 0.02424 ± 0.00922 | 0.01842 ± 0.01033 | 0.02496 ± 0.01443 | 0.01340 ± 0.00580 | 0.01824 ± 0.00976 |
| $2^{nd}$ $C_{trough}$ (ng/mL) | 0.655 ± 0.742 | — | 9.845 ± 4.818 | — | 18.460 ± 8.728 | — |
| $3^{rd}$ $C_{trough}$ (ng/mL) | 0.440 ± 0.685 | — | 8.737 ± 6.674 | — | 16.307 ± 8.960 | — |
| $4^{th}$ $C_{trough}$ (ng/mL) | 0.873 ± 0.683 | — | 10.163 ± 6.318 | — | 14.764 ± 8.343 | — |
| $5^{th}$ $C_{trough}$ (ng/mL) | 0.542 ± 0.867 | — | 7.605 ± 3.944 | — | 13.872 ± 6.968 | — |
| $AUC_{last}$ (d*ng/mL) | — | 56.534 ± 15.945 | — | 382.086 ± 155.201 | — | 623.231 ± 282.722 |
| $t_{1/2}$ (d) | — | *** | — | 3.04 ± 0.94 | — | 3.18 ± 1.15 |
| Lambda_Z (1/d) | — | *** | — | 0.25078 ± 0.09871** | — | 0.24632 ± 0.09975 |
| CL/F (L/d) | — | 17.565 ± 3.818 | — | 16.480 ± 7.341** | — | 20.747 ± 9.540 |
| $V_z$/F (L) | — | *** | — | 55.426 ± 23.760** | — | 105.021 ± 76.365 |
| Median (minimum, maximum) | | | | | | |
| $t_{max}$ (d) | 1 (0.9, 1.9)* | 0.9 (0.9, 1.0) | 1 (0.9, 2.0) | 1 (0.9, 2.0) | 1.9 (1.0, 2.0) | 1.9 (0.9, 2.0) |
| Geometric mean (geometric coefficient of variation %) | | | | | | |
| $C_{max}$ (ng/mL) | 12.314 ± 145.5 | 22.8 02 ± 39.9 | 84.086 ± 55.1 | 108.238 ± 64.6 | 128.474 ± 39.9 | 161.910. ± 59.4* |
| Arithmetic mean ± standard deviation | | | | | | |
| $1^{st}/6^{th}$ $C_{trough}$ (ng/mL) | — | 1.308 ± 33.2 | 7.232 ± 51.1 | 6.831 ± 60.0 | 13.612 ± 42.7 | 13.024 ± 37.5* |
| $AUC_{tau}$ (d*ng/mL) | 31.555 ± 145.3 | 58.135 ± 23.1 | 279.057 ± 45.0 | 329.729 ± 47.2 | 442.982 ± 43.3 | 528.826 ± 52.4* |
| $AUC_{tau}$/dose (d*ng/mL/μg) | 0.03037 ± 152.1 | 0.05813 ± 23.1 | 0.05407 ± 47.1 | 0.06595 ± 47.2 | 0.04291 ± 47.6 | 0.05288 ± 52.4* |
| $C_{max}$/dose (ng/mL/μm) | 0.01185 ± 151.5 | 0.02280 ± 39.9 | 0.01629 ± 57.8 | 0.02165 ± 64.6 | 0.01245 ± 43.8 | 0.01619 ± 59.4* |
| $2^{nd}$ $C_{trough}$ (ng/mL) | 1.289 ± 22.11 | — | 8.960 ± 50.4 | — | 16.775 ± 51.6 | — |
| $3^{rd}$ $C_{trough}$ (ng/mL) | 1.315 ± 11.9 | — | 6.595 ± 103.8 | — | 13.993 ± 71.8 | — |

TABLE 26-continued

| | Parameter | | | | | |
|---|---|---|---|---|---|---|
| | 1 mg apraglutide | | 5 mg apraglutide | | 10 mg apraglutide | |
| Last dose | #1-5 | #6 | #1-5 | #6 | #1-5 | #6 |
| $4^{th}$ $C_{trough}$ (ng/mL) | 1.306 ± 9.2 | — | 8.531 ± 75.1 | — | 12.461 ± 80.8* | — |
| $5^{th}$ $C_{trough}$ (ng/mL) | 1.588 ± 31.2 | — | 6.601 ± 69.1 | — | 11.886 ± 79.3* | — |
| $AUC_{last}$ (d*ng/mL) | — | 54.708 ± 28.7 | — | 353.984 ± 46.4 | — | 574.308 ± 47.5* |
| $t_{1/2}$ (d) | — | *** | — | 2.91 ± 36.6** | — | 3.00 ± 41.3* |
| Lambda_Z (1/d) | — | *** | — | 0.23840 ± 36.6** | — | 0.23103 ± 41.3* |
| CL/F (Lid) | — | 17.201 ± 23.1 | — | 15.164 ± 47.2 | — | 18.910 ± 52.4* |
| $V_z$/F(L) | — | *** | — | 50.202 ± 61.0** | — | 81.852 ± 98.6* |

$AUC_{last}$ = area under the plasma concentration-time curve from time zero to the last measurable concentration;
$AUC_{tau}$ = area under the plasma concentration-time curve to the end of the treatment period of the corresponding dosing;
CL/F = apparent total clearance;
$C_{max}$ = maximum concentration;
$C_{trough}$ = plasma concentration immediately prior to next dosing; lambda
z = terminal elimination rate constant;
PK = pharmacokinetic;
$t_{1/2}$ = terminal elimination half-life;
$t_{max}$ = time to reach maximum plasma concentration;
$V_z$/F = apparent volume of distribution during the terminal elimination phase.
*1 subject missing (N = 5); 2 subjects missing (N = 4) and *3 subjects missing (N = 3, PK parameter not calculated).
Values below the limit of quantification (<1 ng/mL) were set to 0. Number of subjects is 6 unless indicated otherwise.

The concentration profile observed following the sixth dose appeared to be comparable to the first dose, although the exposure was slightly higher (FIG. 20). Exposure indicated dose proportionality with a mean $C_{max}$/dose of 0.02424, 0.02496 and 0.01824 ng/mL/μg and $AUC_{tau}$/dose of 0.05944, 0.07153 and 0.05824 d*ng/mL/μg, for the 1, 5 and 10 mg dose groups, respectively (Table 26).

In 3 out of 6 subjects dosed with 1 mg, insufficient data points were available to determine the terminal elimination rate constant (an insufficient number of samples were above the lower limit of quantification during the sampling period following the last dosing). Subsequently, the mean half-life was determined only for the 5 and 10 mg dose groups and was comparable between the two groups (3.04 and 3.18 days, respectively).

The variability in $C_{max}$ and $AUC_{tau}$ was noticeable following the first dose of 1 mg with a % CV of 145.5 and 145.3%, respectively (Table 26). Following the last dose of 1 mg and both the first and last dose of the 5 and 10 mg dose levels the variability was lower; the % CV for $C_{max}$ ranged from 39.9 to 64.6% and the corresponding range for % CV for $AUC_{tau}$ was 23.1 to 52.4%.

Visual inspection of the dose-normalized pharmacokinetic parameters $C_{max}$ and $AUC_{tau}$ values suggested that over the 1 to 10 mg dose range, apraglutide follows linear kinetics. This is in line with the accompanying constant CL/F.

As with citrulline, a statistical steady-state analysis per dose level was performed for apraglutide using Helmert's approach. This steady-state analysis revealed that none of the contrasts were statistically significant, except for the mean $C_{trough}$ over week 3 to 6 for 10 mg against mean $C_{trough}$ at week 2 (−3.616, 95% CI: −5.893; −1.399 and p=0.0023). Visual inspection of the data suggests that steady state was reached following the first dosing at all investigated dose levels.

Graphical analysis was performed to assess the apraglutide concentration-citrulline effect relationship. Several individual citrulline parameters ($R_{max}$ and $R_{pre\text{-}dose}$) were plotted against apraglutide pharmacokinetic parameters ($C_{max}$, $C_{trough}$ and $AUC_{tau}$). For the parameters assessed at dose 6, a regression line was generated. The p-value of the slope almost reached significance for $C_{max}$ against $R_{max}$ with a value of 0.0608 (FIG. 21). $AUC_{tau}$ appeared to be positively correlated with $R_{max}$ with a p-value of 0.0377 (FIG. 22). According to the regression line, for each 100 d*ng/mL increase in $AUC_{tau}$ in week 6, the corresponding maximum citrulline response increased by 0.39 μg/mL. The R squared value showed that 26% of the variability in $R_{max}$ was explained by $AUC_{tau}$. As shown in FIGS. 23, 24, and 25, the correlation plots of all apraglutide and citrulline concentrations assessed in week 6 by dose level revealed counter-clockwise hysteresis as there was a time delay between the measured apraglutide concentration and the citrulline effect.

Pharmacokinetics

The mean CL/F was constant across the 3 dose levels and ranged from 16.480 (5 mg) to 20.747 L/d (10 mg). The mean $V_z$/F was determined only for the 5 and 10 mg dose groups and was dose dependent with values of 55.426 and 105.021 L for 5 and 10 mg, respectively. The mean t½ could be determined only for the 5 and 10 mg apraglutide dose groups and was comparable for these groups (3.04 and 3.18 days, respectively).

The exposure following the first weekly SC dose of apraglutide indicated dose proportionality with a mean $C_{max}$ of 13.918, 94.088 and 136.855 ng/mL for the 1, 5 and 10 mg dose groups, respectively, and $AUC_{tau}$ values of 35.214, 300.269 and 476.937 d*ng/mL, respectively. The concentration profile observed following the sixth dose was comparable to the first dose, although the exposure was numerically higher. Exposure indicated dose proportionality with a mean $C_{max}$/dose of 0.02424, 0.02496 and 0.01824 ng/mL/μg and $AUC_{tau}$/dose of 0.05944, 0.07153 and 0.05824 d*ng/ mL/μg, for the 1, 5 and 10 mg dose groups, respectively. At dose 1 and 6, $t_{max}$ was approximately 1 day for the 1 mg and 5 mg apraglutide doses and 2 days for the 10 mg dose.

Visual inspection of the dose-normalized pharmacokinetic parameters $C_{max}$ and $AUC_{tau}$ values suggests that over the 1 to 10 mg dose range, apraglutide follows linear kinetics. Visual inspection of the data suggests that steady state was reached following the first dosing at all investigated dose levels.

Pharmacodynamics

Following the first and last dosing with apraglutide, citrulline concentrations dose-dependently increased. The mean citrulline increase observed following the last dose appeared to decline more rapidly for the 1 mg and 5 mg doses compared to the 10 mg dose. Rt1/2 could only be assessed for 2 subjects, both dosed with 10 mg, and was found to be 6.5 and 11.0 days.

At dose 6, the mean $R_{max}$ was 7.1702, 8.1577 and 8.7254 μg/mL following the last dose of 1, 5 and 10 mg, respectively, and was reached at 2.0, 3.9 and 3.9 days. The corresponding placebo value was 6.3707 μg/mL at 16.9 days following the last dose. These $R_{max}$ values were comparable with the mean $R_{max}$ over the whole trial period. Visual inspection of the data suggests that steady state was reached following the first dosing at all investigated dose levels.

A significant treatment effect of apraglutide was observed for citrulline (p=0.0007). Apraglutide induced an increase in citrulline. This response was statistically significant with an increase of 1.2574 μg/mL for 5 mg apraglutide (95% CI: 0.5037; 2.0112; p=0.0025) and 1.6343 μg/mL for 10 mg apraglutide (95% CI: 0.8809; 2.3878; p=0.0002) compared to placebo; for 1 mg apraglutide the increase compared to placebo was not statistically significant (0.3146 μg/mL, 95% CI: −0.4371; 1.0663; p=0.3910)). The contrast between dose groups indicated that the 5 and 10 mg doses induced significantly higher citrulline levels compared to the 1 mg dose (0.9429 μg/mL, 95% CI: 0.1768; 1.7089; p=0.0186 and 1.3198 μg/mL, 95% CI: 0.5586; 2.0810; p=0.0018, respectively). Importantly, the difference between 5 and 10 mg apraglutide was not statistically significant, although the effect following 10 mg appeared to be slightly higher than following 5 mg.

A significant treatment effect of apraglutide on the Bristol stool scale was observed with a p-value of 0.0189 (all dose groups compared to placebo). This effect was not dose-dependent as only a significant decrease compared to placebo was observed for the 1 and 5 mg dose groups (−0.9, 95% CI: −1.6; −0.3; p=0.0092, and −1.0, 95% CI−1.7; −0.4; p=0.0046, respectively).

Exploratory graphical analysis revealed that the slope of the regression line for $C_{max}$ against $R_{max}$ at dose 6 almost reached significance with a p-value of 0.0608. $AUC_{tau}$ appeared to be positively correlated with $R_{max}$ with a p-value of 0.0377. According to the regression line, for each 100 d*ng/mL increase in $AUC_{tau}$ in week 6, the corresponding maximum citrulline response increased by 0.39 μg/mL. The R squared value showed that 26% of the variability in $R_{max}$ was explained by $AUC_{tau}$. The correlation plot of all apraglutide and citrulline concentrations assessed in week 6 revealed counter-clockwise hysteresis.

The MCP-MOD procedure showed that 3 candidate pre-specified models yielded similar results for best fitting the dose response in the MCP part; the 1) $E_{max}$, 2) LogLin and 3) Sigmoid $E_{max}$ model. These 3 models were all applied in the MOD part and predicted similar citrulline changes from placebo for a dose of 1, 5 and 10 mg apraglutide. With a dose of 1 mg, the predicted placebo and baseline corrected change in citrulline across the 3 models ranged from 0.7125 to 0.8712 μg/mL with significant results for the $E_{max}$ (p=0.0184) and LogLin (p=0.0238) models. For the Sigmoid $E_{max}$ model, the p-value was 0.0645. For a dose of 5 mg, the response ranged from 2.1652 to 2.3327 μg/mL. A slightly stronger response was obtained for the 10 mg dose, ranging from 2.6946 to 2.8604 μg/mL. The predicted response versus placebo for both 5 and 10 mg was statistically significant for all models, with a p-value of <0.0001.

The apraglutide dose levels required for a baseline and placebo corrected citrulline increase of 1, 2 and 3 μg/mL were predicted. The $E_{max}$ of the Sigmoid $E_{max}$ model was <3 g/mL, so for this model a change of 2.5 μg/mL was set as the largest response. The predicted apraglutide dose for a citrulline increase of 1 μg/mL was 1.2333 mg (95% CI: −0.04246; 2.5091), 1.2249 mg (95% CI: −0.2169; 2.6667) and 1.3606 mg (95% CI: 0.2680; 2.4532), for the $E_{max}$, LogLin and Sigmoid $E_{max}$ model, respectively. To evoke a citrulline increase of 2 μg/mL, the predicted apraglutide doses were 3.8471 mg (95% CI: 0.3534; 7.3409), 4.2011 mg (95% CI: 0.6406; 7.7617) and 3.4042 mg (95% CI: −0.1290; 6.9374) for the $E_{max}$, LogLin and Sigmoid $E_{max}$ model, respectively. The predicted apraglutide doses for change from placebo of 2.5 or 3 μg/mL were 13.1053 mg (95% CI: −6.3068; 32.5173), 11.4325 mg (95% CI: 1.5808; 21.2843) and 6.4619 mg (95% CI: −0.5521; 13.4759) using the $E_{max}$, LogLin and Sigmoid $E_{max}$ model, respectively.

PD/PK Model

Clinical pharmacokinetic observations were best matched by a model with correlation between V1/F and C1/F and a dose covariate on absorption duration as well as body weight covariates on V1/F and C1/F. Pharmacodynamic observations were then added to this model to create the PK/PD model. Plasma citrulline was described by a turnover model and maximal PD effect model.

The population PK/PD model estimated that a 70-kg individual who received apraglutide 5 mg subcutaneous injection would achieve a volume of distribution of 31.3 L and peak plasma concentration ($C_{max}$) at 1.39 days. Simulated apraglutide and citrulline plasma concentration profiles with weekly subcutaneous injection of apraglutide 2.5, 5, or 10 mg are shown in FIG. 26.

The PK/PD model did not indicate any accumulation of apraglutide over time. Although accumulation of citrulline was apparent during the first three weeks of treatment, a steady state concentration was subsequently reached. Simulated apraglutide concentration-time profiles by body weight indicated a lower area-under-the curve (AUC) and $C_{max}$ at steady state with increasing body weight.

Example 8: Apraglutide Manufacturing Process—(II)

The following is an exemplary method of the present disclosure for the manufacture of apraglutide at improved levels of purity relative to previously described synthesis routes (e.g. U.S. Pat. No. 8,580,918).

Solid Phase Peptide Synthesis (Step 1)

SPPS is the sequential synthesis of a peptide chain anchored on a solid support by repetition of a cycle encompassing the following steps:

1. Removal of the N-terminus Fmoc protecting group of the peptide resin
   1a. In some aspects, the Fmoc deprotection reaction of residue $Asp^3$ comprises treating the resin with a solution of 10% piperidine and 2% Oxyma in DMF.

The deprotection reaction is performed in two cycles, the first one for 15 minutes and the second one for 30 minutes.
2. DMF washes
3. Couplings of Fmoc-AA-OH
4. Coupling test
5. DMF washes This cycle is repeated until the peptide sequence is completed.

The α-amino groups of the amino acids are protected with the base-sensitive 9-fluorenylmethyloxycarbonyl (Fmoc) group; the side chain functional groups are protected with acid-labile groups. All amino acids derivatives used in the process are commercially available.

SPPS is the sequential synthesis of a peptide chain anchored on a solid support. In the synthesis, MBHA resin may be used to assemble the peptide sequence. After swelling and washing the resin with DMF and then with DMF/DIEA under nitrogen atmosphere the Fmoc-Rink-amide linker may be coupled using HBTU/DIPEA/HOBt in DMF. After coupling, the resin may be washed with DMF and then acetylated using $Ac_2O$/DIPEA. A Kaiser test may be carried out to check completion of the coupling.

After washing the resin with DMF, the Fmoc protected amino acids are each coupled to the resin-bond peptide according to the following cycle:

1. The Fmoc-protecting group is removed with piperidine in DMF and the resin is washed thoroughly with DMF.
2. The coupling is performed in DMF with variable amino acid equivalents using DIC/oxyma for activation.
   2a. In some aspects, the di-peptide Boc-His(Trt)-Gly-OH is coupled to the resin instead of sequential assembly of Gly and His amino acids. The dipeptide is preactivated for 1 hour at 20° C.±2° C. using Boc-His (Trt)-Gly-OH/Oxyma/DIC (2.5 mmol/2.5 mmol/2.5 mmol) in 7 mL DMF, before addition to the coupling reaction. A Kaiser test may be carried out to check completion of the coupling.
3. Coupling of amino acids is monitored by using the Ninhydrin assay, which is performed during each synthesis cycle.

At the end of the assembly, after the last amino acid has been coupled and deprotected, the resin is washed with DMF and isopropanol, and dried under vacuum.

Cleavage of the Peptide from the Resin and Deprotection (Step 2)

The protected peptide may be simultaneously cleaved from the resin and deprotected by treatment with a mixture TFA/water/anisole. MTBE is subsequently added to the peptide/TFA slurry to precipitate the crude peptide in the presence of cleaved resin. The obtained crude peptide is filtered, washed with MTBE and dried under vacuum to constant weight.

Decarboxylation Reaction (Step 3a)

The crude peptide is solubilized in a mixture of $H_2O$/ACN (70:30 ratio) in ammonia buffer. The solution is adjusted to target pH 8.0±0.1 using 25% acetic acid or 25% $NH_4OH$ in $H_2O$. The decarboxylation reaction is maintained at 50° C. for 65 minutes. The crude peptide is washed with a solution of $H_2O$/ACN (70:30 ratio) in ammonia buffer at pH 8.0±0.1 and stored at 5°±3° C.

Purification by Preparative RP-HPLC (Step 3b)

The crude peptide is dissolved in a mixture of water/acetonitrile/NH4OH. This solution is diluted with acetic acid and then filtered.

The primary purification is conducted on preparative RP-HPLC with $NaHCO_3/H_2O/CH_3CN$ as eluent. The elution from the column is monitored by UV and the fractions obtained are analyzed by RP-HPLC. Fractions meeting the monitoring criteria are mixed in the combined pool. Fractions not meeting the monitoring criteria may be recycled by repeating the purification step. The purity of the pool is controlled by analytical RP-HPLC.

Sodium Salt Conversion by Preparative RP-HPLC (Step 4)

This step may be conducted to exchange the counter ion of the peptide from a TFA anion to a sodium cation through a pH change and to further purify the peptide. The combined pool from Step 3 is diluted in water and re-purified by preparative RP-HPLC using NaOAc eluent.

The purified peptide solution is subsequently subject to evaporation under vacuum to reduce acetonitrile in the solution. The purified peptide solution is then adjusted to target pH 7.9 using 0.1% AcOH.

The pure pool may be concentrated and freeze-dried. The purity of the pool is analyzed by RP-HPLC.

Freeze-Drying and Packaging (Step 5)

Prior to lyophilization, the purified peptide in solution is filtered through a 0.2 μm membrane. The lyophilization is carried out at low pressure. The resulting lyophilized final peptide is packed under argon. The lyophilized apraglutide is controlled according to the apraglutide specification.

Reprocessing

Lyophilized apraglutide that does not fulfil the criteria established in the apraglutide specification may be subjected to re-purification.

Re-purification may be carried out after reconstitution of the peptide by repeating the purification step(s) and counterion conversion step, as described above.

After re-purification, the material is lyophilized according to the procedure described above.

Lyophilized apraglutide that does not fulfil the criteria established in the apraglutide specification may be subjected to re-lyophilization.

Re-lyophilization may be carried out after reconstitution of the peptide by repeating the lyophilization step, as described above.

Impurities

The apraglutide manufacturing process as described in Example 8 was performed to reduce the level of β-$Asp^3$ peptide isomer impurity in apraglutide below 1.5%. In some embodiments, the apraglutide manufacturing process as described in Example 8 reduced the level of β-$Asp^3$ peptide isomer impurity in apraglutide below 1%.

Formation of the β-$Asp^3$ impurity is favored by high pH and the presence of the sequence $Asp^3$-$Gly^4$. The Asp-Gly sequence is particularly prone to aspartimide formation, resulting from a ring-closure (attack of the nitrogen from the α-carboxy amide bond on the β-carboxy side chain). Aspartamides are susceptible to base-catalyzed epimerization and may undergo ring-opening reactions, which may lead to the formation of multiple by-products. Attack by water may produce the β-aspartyl peptide.

The formation of β-$Asp^3$ impurity during the decarboxylation/extraction step (Step 3a) upon peptide cleavage from resin can reach levels of >1% and is promoted by prolonged exposure to extreme pHs, in particular, strong base solution of ammonia in H2O/ACN 80:20, pH around 10 at room temperature. The apraglutide manufacturing process as described in Example 8 reduced the pH from 10 to 8, shortened the decarboxylation reaction time from 24 hours to 65 minutes, changed the reaction temperature from Room Temperature to 50° C., and reduced the storage temperature from Room Temperature to 5° C. These changes resulted in β-$Asp^3$ impurity at levels below 1.5%. In some embodiments, these changes resulted in β-$Asp^3$ impurity at levels below 1%.

The apraglutide manufacturing process as described in Example 8 amended the_Fmoc deprotection reaction of residue $Asp^3$ to use a solution of 10% piperidine and 2% Oxyma in DMF with two cycles of deprotection, the first one for 15 minutes and the second one for 30 minutes. These milder basic conditions allowed a complete deprotection of $Asp^3$ and decrease the aspartimide and subsequent β-$Asp^3$ by-product formation.

The formation of a D-His impurity may occur due to the racemization of the amino acid during the coupling reaction using DIC/Oxyma. A process of sequential assembly of individual Gly and His amino acids showed variability in levels of D-His impurity between 0.3%-1.2%, sometimes with incomplete coupling. Fmoc-His(Trt)-OH incorporation using the coupling reagents DIC/Oxyma may favor the racemization into the D form of His.

The apraglutide manufacturing process as described in Example 8 used the di-peptide Boc-His(Trt)-Gly-OH as starting material for this reaction instead of sequential assembly of Gly and His amino acids. This allows decreasing the racemization level in His to below 1% (0.3% in one performed batch) and incorporates the final D-His level to the specifications of the dipeptide (Boc-D-His(Trt)-Gly-OH). This also allows a reduction in the number of deprotection steps, thus minimizing the contributing impact of deprotection conditions (high pH) to the β-$Asp^3$ impurity formation, as described above.

Example 9: Phase III Human Clinical Trial of Administration of Apraglutide Compositions of the Present Disclosure The following non-limiting example describes a Phase 3 clinical trial in which subjects with SBS-IF are treated with the apraglutide formulations of the present disclosure. This Phase 2 clinical trial investigates efficacy of weekly subcutaneous apraglutide in reducing parenteral support dependency in patients with SBS-IF.

144 adult patients with SBS-IF will be treated with apraglutide compositions of the present disclosure of placebo. Patients with SBS-IF will be administered 2.5 mg apraglutide of the present disclosure when the subject has a body weight of less than 50 kg, or 5 mg apraglutide of the present disclosure when the subject has a body weight greater than or equal to 50 kg, or placebo once a week for 48 weeks.

The trial is a multicenter, double-blind, randomized, placebo-controlled, phase 3 trial. Randomization of participants includes stoma and colon-in-continuity anatomy-specific randomization.

Primary endpoint efficacy assessments will be performed at 24 weeks. The primary endpoint will evaluate the relative change from baseline in actual weekly PS volume. Secondary endpoint efficacy assessments will be performed at 24 weeks and 48 weeks. Anatomy specific secondary endpoints as well as secondary endpoints common across all patients will be evaluated.

The secondary endpoints to be evaluated, include, but are not limited to:

1. Subjects who achieve a reduction of at least 1 day per week of PS at Weeks 24/48.
2. Relative change from baseline in actual weekly PS volume at Weeks 12/24/48.
3. SBS-IF patients reaching enteral autonomy at Weeks 24/48.
4. At least 20% reduction of PS volume from baseline at Weeks 20/24.
5. Calorie reduction in the parenteral nutrition (PN) at Weeks 24.
6. Change from baseline on the Patient Global Impression of Severity (PGIS)
7. Change from baseline on the Pittsburgh Sleep Quality Inventory (PSQI)
8. Change from baseline on the Patient Global Impression of Change (PGIC)
9. Absorption rate constant (ka) of apraglutide through population PK data analysis
10. Apparent clearance (CL/F) of apraglutide through population PK data analysis
11. Apparent volume of distribution (Vz/F) of apraglutide through population PK data analysis Example 10: Phase I Human Clinical Trial of Administration of Apraglutide Compositions of the Present Disclosure The following non-limiting example describes a Phase I clinical trial in which subjects with normal and impaired kidney function are treated with the apraglutide formulations of the present disclosure. This Phase I clinical trial investigates the pharmacokinetics and safety of a single subcutaneous dose of 5 mg apraglutide in subjects with varying degrees of renal function. The renal function is calculated by the estimated glomerular filtration rate (eGFR) according to the Chronic Kidney Disease Epidemiology (CKD-EPI) Creatinine Equation.

The trial is a two-stage, open label, multi-center, non-randomized, Phase I trial. In Part 1 of the trial, 8 subjects with severe renal impairment (Cohort 1) and 6 subjects with normal renal function (Cohort 2) will be administered a single dose 5 mg apraglutide of the present disclosure. In Part 2 of the trial, 8 subjects with moderate renal impairment (Cohort 3) and 8 subjects with mild renal impairment (Cohort 4) will be administered a single dose 5 mg apraglutide of the present disclosure. Subjects will be enrolled if the geometric mean ratio (GMR) of $AUC_{inf}$ or $AUC_{last}$ for the severe renal impairment group compared to the control group is ≥2.

Patient eligibility is assessed during a screening visit. The main inclusion criteria are:

1. All Participants
   a. Age between 18 and 75 years inclusive
   b. Subjects who are willing and able to comply with the study procedures
   c. Subjects able to understand and willing to sign the informed consent
   d. Body mass index (BMI) of ≥17.5 to ≤40 kg/m2; and a total body weight of >50 kg (110 lb).
   e. Women of childbearing potential (WOCBP) on highly effective method of contraception during the trial and for 1 month after the end of trial (EOT) visit. Sterilized or infertile or postmenopausal females.
   f. Male subjects with a female partner of childbearing potential: highly effective methods of contraception and no sperm donation during the trial and for 1 month after (EOT) visit.

2. Healthy participants
    a. No clinically relevant abnormalities (medical history, vital signs, ECG, safety labs)
    b. eGFR measured by CKD-EPI≥90 mL/min/1.73 m2 at two screening visits
    c. Demographically comparable to the group of subjects with impaired renal function
3. Participants with impaired renal function
    a. Severe renal impairment: eGFR<30 mL/min/1.73 m2, but not requiring hemodialysis
    b. Moderate renal impairment: eGFR≥30 mL/min/1.73 m2 and <60 mL/min/1.73 m2
    c. Mild renal impairment: eGFR≥60 and <90 mL/min/1.73 m2

Primary endpoint efficacy assessments will be performed at 240 hours after single dose. The primary endpoint will evaluate maximum plasma ($C_{max}$), area under the concentration-time curve from 0 to infinity ($AUC_{inf}$) and area under the concentration-time curve up to last measurable concentration ($AUC_{last}$), from time 0 to 240 hours. Secondary endpoint efficacy assessments will be performed at 240 hours, 7 days, 14 days, and 28 days. Primary and secondary endpoints will be evaluated across all subjects.

The secondary endpoints to be evaluated, include, but are not limited to:

1. Area under the concentration-time curve up to the last measurable concentration from time 0 to 7 days ($AUC_{0-7\ days}$). Samples collected over 168 hours after single dose
2. Time to maximum concentration ($T_{max}$). Samples collected over 240 hours after single dose
3. Terminal elimination rate constant. Samples collected over 240 hours after single dose
4. Terminal elimination half-life. Samples collected over 240 hours after single dose
5. Apparent clearance after extravascular administration (CL/F). Samples collected over 240 hours after single dose
6. Apparent volume of distribution after extravascular administration (Vz/F). Samples collected over 240 hours after single dose
7. Number of participants with adverse events or adverse events of special interest at days 14-28
8. Clinically significant change from baseline in vital signs at days 14-28
9. Clinically significant change from baseline in recorded triplicate 12-lead ECG at days 14-28
10. Number of participants who experience a clinically significant change from baseline in clinical laboratory assessments at days 14-28

As would be appreciated by the skilled artisan, patients with renal impairment usually require drug dosing adjustments because renal impairment can adversely affect some pathways of hepatic/gut drug metabolism, and has also been associated with other changes such as changes in absorption, plasma protein binding, transport, and tissue distribution. Even if pharmacokinetic data indicated that renal excretion is not the primary route of elimination for apraglutide, other GLP-2 analogues (i.e. teduglutide) necessitate dose reduction in patients with moderate and severe renal impairment and end-stage renal disease. In the trial described in Example 10, it has been found that it is safe to dose the patients with severe CKD with apraglutide 5 mg, without the risk of overdose in this population. Without wishing to be bound by theory, this indicates that apraglutide has the potential of being administered to renal impaired patients without dose adaptation.

Pharmacokinetics

The plasma concentration of apraglutide after administration of a single subcutaneous dose of 5 mg apraglutide was monitored over a period of 240 hours in both healthy subjects (Cohort 2) and subjects with severe CKD (Cohort 1) and is presented in FIG. 29.

Summary of pharmacokinetic parameters of apraglutide are provided in Table 27. Two outliers were identified (one in each Cohort) when analyzing the individual apraglutide plasma concentration curves. The outlier in Cohort 1 had the highest bodyweight (BW) and body mass index (BMI) in the group while the outlier in Cohort 2 had the lowest BW and BMI in the group. The geometric mean rations were calculated with and without the outlier subjects.

TABLE 27

| Single dose 5 mg apraglutide | | | |
|---|---|---|---|
| Parameter | 90% CI Lower Bound | Geometric Mean Ratio | 90% CI Higher Bound |
| | Whole Cohort | | |
| $C_{max}$ (ng/mL) | 0.370 | 0.572 | 0.885 |
| $AUC_{inf}$ (h*ng/mL) | 0.388 | 0.614 | 0.972 |
| | Cohort without the two outliers | | |
| $C_{max}$ (ng/mL) | 0.556 | 0.774 | 1.077 |
| $AUC_{inf}$ (h*ng/mL) | 0.657 | 0.849 | 1.098 |

$C_{max}$ = maximum plasma;
$AUC_{inf}$ = area under the concentration-time curve from 0 to infinity For the entire subject population, the geometric mean ratio for $C_{max}$ was 0.572 with 90% CI 0.37-0.885 and for $AUC_{inf}$ was 0.614 with 90% CI 0.388-0.972. Whereas, when removing the data from the outlier subjects the geometric mean ratio for $C_{max}$ was 0.774 with 90% CI 0.556-1.077 and for $AUC_{inf}$ was 0.849 with 90% CI 0.657-1.098. As would be appreciated by the skilled artisan, patients with severe renal impairment have higher bodyweight and body mass index than healthy subjects. Without wishing to be bound by theory, this may indicate that the subjects in Cohort 1 have lower exposure to apraglutide due to lower plasma concentrations.

Example 11: Apraglutide Manufacturing Process—(III)

FIG. 2A and FIG. 2B schematically depict an exemplary method of the present disclosure for the manufacture of apraglutide at improved levels of purity relative to previously described synthesis routes (e.g. U.S. Pat. No. 8,580,918). The manufacture process described in FIG. 2A and FIG. 2B is herein referred to as Process B and incorporates primary purification by RP-HPLC (C18) chromatography in TFA-based mobile phases ($H_2O$/acetonitrile) to ≥90% purity with pH of fractions adjusted using sodium bicarbonate ($NaHCO_3$), followed by secondary purification by RP-HPLC (C18) in $NaHCO_3$ mobile phases ($H_2O$/acetonitrile) to ≥97% purity, and followed by desalting/buffer exchange by RP-HPLC (C18) in sodium acetate (NaOAc)/$H_2O$/acetonitrile mobile phases. Table 2a shows the purity of Apraglutide product produced using Process B, as well as the level of major contaminants. Table 2a shows the purity of Apraglutide product produced using Process B, as well as overall product yields for the process. As shown in Table 2a and Table 2b, Process B can yield Apraglutide that has a purity of no less than 97%, and low levels of contaminants. Moreover, Process B exhibits product yields of about 20%.

Impurities

The apraglutide manufacturing process as described in FIG. 2A and FIG. 2B can be further modified to reduce the level of β-$Asp^3$ peptide isomer impurity in apraglutide below 1.5%. In some embodiments, the apraglutide manufacturing process as described in Example 8 reduced the level of β-$Asp^3$ peptide isomer impurity in apraglutide below 1%.

Formation of the β-$Asp^3$ impurity is favored by high pH and the presence of the sequence $Asp^3$-$Gly^4$. The Asp-Gly sequence is particularly prone to aspartimide formation, resulting from a ring-closure (attack of the nitrogen from the α-carboxy amide bond on the β-carboxy side chain). Aspartamides are susceptible to base-catalyzed epimerization and may undergo ring-opening reactions, which may lead to the formation of multiple by-products. Attack by water may produce the β-aspartyl peptide.

The formation of β-$Asp^3$ impurity during the decarboxylation/extraction step (Step 3(1), FIG. 2B) upon peptide cleavage from resin can reach levels of >1% and is promoted by prolonged exposure to extreme pHs, in particular, strong base solution of ammonia in H2O/ACN 80:20, pH around 10 at room temperature. The apraglutide manufacturing process as described in FIG. 2A and FIG. 2B can be modified as to reduce the pH from 10 to 8, shorten the decarboxylation reaction time from 24 hours to 65 minutes, change the reaction temperature from room temperature to 50° C., and reduce the storage temperature from room temperature to 5° C. These changes can result in β-$Asp^3$ impurity at levels below 1.5%. In some embodiments, these changes resulted in β-$Asp^3$ impurity at levels below 1%.

The apraglutide manufacturing process as described in FIG. 2A and FIG. 2B can also be modified such that the Fmoc deprotection reaction of residue $Asp^3$ to use a solution of 10% piperidine and 2% Oxyma in DMF with two cycles of deprotection, the first one for 15 minutes and the second one for 30 minutes. These milder basic conditions allow a complete deprotection of $Asp^3$ and decrease the aspartimide and subsequent β-$Asp^3$ by-product formation.

The formation of a D-His impurity may occur due to the racemization of the amino acid during the coupling reaction using DIC/Oxyma. A process of sequential assembly of individual Gly and His amino acids showed variability in levels of D-His impurity between 0.3%-1.2%, sometimes with incomplete coupling. Fmoc-His(Trt)-OH incorporation using the coupling reagents DIC/Oxyma may favor the racemization into the D form of His.

The apraglutide manufacturing process as described in FIG. 2A and FIG. 2B can be modified to use the di-peptide Boc-His(Trt)-Gly-OH as starting material for this reaction instead of sequential assembly of Gly and His amino acids. This allows decreasing the racemization level in His to below 1% (0.3% in one performed batch) and incorporates the final D-His level to the specifications of the dipeptide (Boc-D-His(Trt)-Gly-OH). This also allows a reduction in the number of deprotection steps, thus minimizing the contributing impact of deprotection conditions (high pH) to the β-$Asp^3$ impurity formation, as described above.

The apraglutide manufacturing process as described in FIG. 2A and FIG. 2B, and modified as described above, is herein referred to as "Process C". As shown in Table 2b, Process C can yield Apraglutide that has a purity of no less than 97% and exhibits product yields of about 22%.

EQUIVALENTS

The foregoing description has been presented only for the purposes of illustration and is not intended to limit the disclosure to the precise form disclosed. The details of one or more embodiments and/or aspects of the disclosure are set forth in the accompanying description above. Any one of the embodiments and/or aspects described herein can be combined with any other embodiment and/or aspect described herein, and any number of embodiments and/or aspects can be combined. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

What is claimed is:

1. A method of treating short bowel syndrome (SBS) in a human subject, the method comprising administering an aqueous pharmaceutical composition comprising apraglutide, or a pharmaceutically acceptable salt thereof, to the human subject once weekly by subcutaneous injection, wherein the apraglutide is at a dose between 1 mg and 10 mg.

2. The method of claim 1, wherein the human subject has short bowel syndrome associated intestinal failure (SBS-IF).

3. The method of claim 1, wherein the human subject has short bowel syndrome associated intestinal insufficiency (SBS-II).

4. The method of claim 1, wherein the human subject has colon-in-continuity (CIC).

5. The method of claim 4, wherein the human subject has greater than 50% colon-in-continuity (CIC).

6. The method of claim 1, wherein the human subject has at least one stoma.

7. The method of claim 1, wherein the human subject has a jejunostomy or ileostomy.

8. The method of claim 1, wherein administering the apraglutide or pharmaceutically acceptable salt thereof increases plasma citrulline levels in the human subject for at least 10 days after a last dose of apraglutide.

9. The method of claim 1, wherein the human subject is receiving parenteral support, and wherein the method further comprises reducing the amount of parenteral support administered to the human subject following administration of the apraglutide or pharmaceutically acceptable salt thereof.

10. The method of claim 1, wherein a sodium salt of apraglutide is administered.

11. The method of claim 10, wherein the sodium salt of apraglutide has a purity of no less than 95% as determined by high-performance liquid chromatography (HPLC).

12. The method of claim 11, wherein the sodium salt of apraglutide comprises no more than 5% of an impurity comprising one or more of Des-$Gly^4$, $Aspartimide^3$, $Asp^{33}$-OH, Des-$Ser^7$, [$Trp^{25}$, 2-(2,4,6-trimethoxyphenyl)], and D-$Asp^3$.

13. The method of claim 11, wherein the sodium salt of apraglutide comprises no more than 3% of a β-$Asp^3$ apraglutide impurity.

14. The method of claim 13, wherein the sodium salt of apraglutide comprises no more than 2% of a β-$Asp^3$ apraglutide impurity.

15. The method of claim 11, wherein the sodium salt of apraglutide comprises no more than 1.5% of a D-His apraglutide impurity.

16. The method of claim 11, wherein the sodium salt of apraglutide comprises no more than 2.5% of an apraglutide impurity comprising Des-$Gly^4$.

17. The method of claim 16, wherein the sodium salt of apraglutide comprises no more than 2% of an apraglutide impurity comprising Des-$Gly^4$.

18. The method of claim 11, wherein the sodium salt of apraglutide comprises no more than 1% of an apraglutide impurity comprising Des-$Ser^7$.

19. The method of claim 11, wherein the sodium salt of apraglutide comprises:

a) no more than 2% of a β-$Asp^3$ apraglutide impurity;
b) no more than 1.5% of a D-His apraglutide impurity; and
c) no more than 1% of an apraglutide impurity comprising Des-$Ser^7$.

20. The method of claim 11, wherein the sodium salt of apraglutide comprises:

a) no more than 3% of a β-$Asp^3$ apraglutide impurity; and
b) no more than 1% of an apraglutide impurity comprising Des-$Ser^7$.

21. The method of claim 10, wherein a pharmaceutical composition comprising the sodium salt of apraglutide is administered.

22. The method of claim 21, wherein the pharmaceutical composition further comprises glycine, L-histidine, and mannitol.

23. The method of claim 10, wherein the sodium salt of apraglutide is administered via a two-chamber syringe.

24. The method of claim 21, wherein the pharmaceutical composition has a pH value of between about 8.2 and about 8.4.

25. The method of claim 24, wherein the pharmaceutical composition has a pH value of about 8.3.

26. The method of claim 24, wherein the pharmaceutical composition further comprises glycine, L-histidine, and mannitol.

27. A method of treating short bowel syndrome (SBS) in a human subject, the method comprising subcutaneously administering a once weekly dose of between 1 mg and 10 mg apraglutide to the human subject in an aqueous pharmaceutical composition.

28. The method of claim 27, wherein the human subject has short bowel syndrome associated intestinal failure (SBS-IF).

29. The method of claim 27, wherein the human subject has short bowel syndrome associated intestinal insufficiency (SBS-II).

30. The method of claim 27, wherein the human subject has colon-in-continuity (CIC).

31. The method of claim 27, wherein the apraglutide is at a dose between about 5 mg and about 10 mg.

32. The method of claim 1, wherein the apraglutide is at a dose between about 5 mg and about 10 mg.

* * * * *